(12) United States Patent
Hong et al.

(10) Patent No.: US 9,724,303 B2
(45) Date of Patent: *Aug. 8, 2017

(54) LIPOSOMES USEFUL FOR DRUG DELIVERY

(71) Applicant: Ipsen Biopharm Ltd., Wrexham (GB)

(72) Inventors: Keelung Hong, San Francisco, CA (US); Daryl C. Drummond, Lincoln, MA (US); Dmitri Kirpotin, Revere, MA (US)

(73) Assignee: IPSEN BIOPHARM LTD., Wrexham (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/965,140

(22) Filed: Dec. 10, 2015

(65) Prior Publication Data

US 2016/0095817 A1    Apr. 7, 2016

Related U.S. Application Data

(60) Continuation of application No. 14/632,422, filed on Feb. 26, 2015, which is a division of application No.
(Continued)

(51) Int. Cl.
*A61K 9/127* (2006.01)
*A61K 9/00* (2006.01)
(Continued)

(52) U.S. Cl.
CPC .......... *A61K 9/1271* (2013.01); *A61K 9/0019* (2013.01); *A61K 9/127* (2013.01);
(Continued)

(58) Field of Classification Search
None
See application file for complete search history.

(56) References Cited

U.S. PATENT DOCUMENTS 4,192,869 A    3/1980 Nicolau et al.
4,321,259 A    3/1982 Nicolau et al.
(Continued)

FOREIGN PATENT DOCUMENTS

CN    1351495    10/2004
DE    4320597    1/1995
(Continued)

OTHER PUBLICATIONS

T-H Chou, S-C Chen, I-M Chu. "Effect of Composition on the Stability of Liposomal Irinotecan Prepared by a pH Gradient Method." Journal of Bioscience and Bioengineering, vol. 95 No. 4, 2003, pp. 405-408.*

(Continued)

*Primary Examiner* — Isaac Shomer
(74) *Attorney, Agent, or Firm* — Cynthia M. Bott; Christopher C. Forbes; Honigman Miller Schwartz and Cohn LLP

(57) ABSTRACT

The present invention provides liposome compositions containing substituted ammonium and/or polyanion, and optionally with a desired therapeutic or imaging entity. The present invention also provide methods of making the liposome compositions provided by the present invention.

20 Claims, 29 Drawing Sheets

Related U.S. Application Data

14/175,365, filed on Feb. 7, 2014, now Pat. No. 8,992,970, which is a continuation of application No. 13/654,373, filed on Oct. 17, 2012, now Pat. No. 8,703,181, which is a continuation of application No. 13/416,204, filed on Mar. 9, 2012, now Pat. No. 8,329,213, which is a continuation of application No. 11/121,294, filed on May 2, 2005, now Pat. No. 8,147,867.

(60) Provisional application No. 60/567,921, filed on May 3, 2004.

(51) Int. Cl.

| | |
|---|---|
| *A61K 31/4745* | (2006.01) |
| *A61K 31/475* | (2006.01) |
| *A61K 31/704* | (2006.01) |
| *A61K 31/337* | (2006.01) |
| *A61K 31/4375* | (2006.01) |
| *A61K 47/26* | (2006.01) |
| *A61K 47/48* | (2006.01) |
| *A61K 47/10* | (2017.01) |
| *A61K 47/24* | (2006.01) |
| *A61K 47/28* | (2006.01) |
| *C07H 13/12* | (2006.01) |

(52) U.S. Cl.
CPC .......... *A61K 9/1277* (2013.01); *A61K 9/1278* (2013.01); *A61K 31/337* (2013.01); *A61K 31/4375* (2013.01); *A61K 31/475* (2013.01); *A61K 31/4745* (2013.01); *A61K 31/704* (2013.01); *A61K 47/10* (2013.01); *A61K 47/24* (2013.01); *A61K 47/26* (2013.01); *A61K 47/28* (2013.01); *A61K 47/48823* (2013.01); *C07H 13/12* (2013.01); *Y10S 977/773* (2013.01); *Y10S 977/906* (2013.01); *Y10S 977/907* (2013.01)

(56) References Cited

U.S. PATENT DOCUMENTS

| | | | |
|---|---|---|---|
| 4,397,846 A | 8/1983 | Weiner et al. | |
| 4,649,155 A | 3/1987 | Steffen et al. | |
| 4,960,790 A | 10/1990 | Stella et al. | |
| 5,013,556 A | 5/1991 | Woodle et al. | |
| 5,043,165 A | 8/1991 | Radhakrishnan | |
| 5,059,591 A | 10/1991 | Janoff et al. | |
| 5,077,056 A | 12/1991 | Bally et al. | |
| 5,192,549 A | 3/1993 | Barenolz et al. | |
| 5,281,237 A | 1/1994 | Gimpelson | |
| 5,316,771 A | 5/1994 | Barenholz et al. | |
| 5,498,420 A | 3/1996 | Mentrup Edgar et al. | |
| 5,534,241 A | 7/1996 | Torchilin et al. | |
| 5,538,954 A | 7/1996 | Koch et al. | |
| 5,736,155 A | 4/1998 | Bally et al. | |
| 5,741,516 A | 4/1998 | Webb et al. | |
| 5,783,568 A * | 7/1998 | Schlessinger .......... A61K 31/70 514/13.3 |
| 5,785,987 A | 7/1998 | Hope et al. | |
| 5,795,589 A | 8/1998 | Mayer et al. | |
| 6,022,561 A | 2/2000 | Carlsson et al. | |
| 6,063,400 A | 5/2000 | Geho et al. | |
| 6,083,923 A | 7/2000 | Hardee et al. | |
| 6,110,491 A | 8/2000 | Kirpotin | |
| 6,210,707 B1 | 4/2001 | Papahadjopoulos et al. | |
| 6,291,676 B1 | 9/2001 | Burke et al. | |
| 6,355,268 B1 | 3/2002 | Slater et al. | |
| 6,417,326 B1 | 7/2002 | Cullis et al. | |
| 6,465,008 B1 | 10/2002 | Slater et al. | |
| 6,743,917 B2 | 6/2004 | Curran et al. | |
| 7,238,367 B2 | 7/2007 | Tardi et al. | |
| 8,147,867 B2 * | 4/2012 | Hong .................. A61K 9/0019 424/450 |
| 8,329,213 B2 * | 12/2012 | Hong .................. A61K 9/0019 424/450 |
| 8,658,203 B2 * | 2/2014 | Drummond .......... A61K 9/0019 424/450 |
| 8,703,181 B2 * | 4/2014 | Hong .................. A61K 9/0019 424/450 |
| 8,992,970 B2 * | 3/2015 | Hong .................. A61K 9/0019 424/417 |
| 2001/0034363 A1 | 10/2001 | Li et al. | |
| 2001/0038851 A1 * | 11/2001 | Allen .................. A61K 9/127 424/450 |
| 2002/0028919 A1 | 3/2002 | Matulic-Adamic et al. | |
| 2002/0035091 A1 | 3/2002 | Govindarajan et al. | |
| 2002/0045756 A1 | 4/2002 | Leue et al. | |
| 2002/0049176 A1 | 4/2002 | Anderson et al. | |
| 2002/0102298 A1 | 8/2002 | Needham | |
| 2002/0146450 A1 | 10/2002 | Slater et al. | |
| 2002/0192275 A1 | 12/2002 | Zalipsky | |
| 2003/0129224 A1 | 7/2003 | Tardi et al. | |
| 2003/0138481 A1 | 7/2003 | Zadi | |
| 2003/0220284 A1 | 11/2003 | Yotnda et al. | |
| 2004/0013720 A1 | 1/2004 | Ellens et al. | |
| 2004/0071768 A1 | 4/2004 | Sarris et al. | |
| 2004/0142025 A1 | 7/2004 | MacLachlan et al. | |
| 2004/0156889 A1 | 8/2004 | Hu et al. | |
| 2004/0156891 A1 | 8/2004 | Bolotin et al. | |
| 2004/0243101 A1 | 12/2004 | Gillis | |
| 2005/0112065 A1 | 5/2005 | Drummond et al. | |
| 2006/0129126 A1 | 6/2006 | Kaplitt et al. | |
| 2006/0135945 A1 | 6/2006 | Bankiewicz et al. | |
| 2007/0110798 A1 | 5/2007 | Drummond et al. | |
| 2008/0095819 A1 | 4/2008 | Gourdie et al. | |

FOREIGN PATENT DOCUMENTS

| | | |
|---|---|---|
| EP | 1 121 102 B1 | 8/1992 |
| EP | 0 592 446 B1 | 10/1995 |
| EP | 1 121 102 B1 | 4/2003 |
| JP | 2000/516641 | 12/2000 |
| RU | 98116122 | 8/1997 |
| RU | 2125868 C1 | 2/1999 |
| RU | 2130771 C1 | 5/1999 |
| WO | 90/14074 | 11/1990 |
| WO | 96/25147 | 8/1996 |
| WO | 96/26715 A1 | 9/1996 |
| WO | 97/28156 A1 | 8/1997 |
| WO | 98/17256 | 4/1998 |
| WO | 99/01110 A1 | 1/1999 |
| WO | 9901110 A1 | 1/1999 |
| WO | 00/09071 | 2/2000 |
| WO | 00/66126 A2 | 11/2000 |
| WO | 03/030684 A1 | 4/2003 |
| WO | 03030864 A1 | 4/2003 |
| WO | 03/092700 | 11/2003 |
| WO | 2004/017940 | 3/2004 |
| WO | 2004047801 A2 | 6/2004 |
| WO | 2005/002546 | 1/2005 |

OTHER PUBLICATIONS

Science Direct Abstract of T-H Chou, S-C Chen, I-M Chu. "Effect of Composition on the Stability of Liposomal Irinotecan Prepared by a pH Gradient Method." Journal of Bioscience and Bioengineering, vol. 95 No. 4, 2003, pp. 405-408. http://www.sciencedirect.com/science/article/pii/S1389172303800762, accessed Mar. 7, 2016, 1 printed page.*

SM Berge, LD Bighley, DC Monkhouse. "Pharmaceutical Salts." Journal of Pharmaceutical Sciences, vol. 66 No. 1, Jan. 1977, pp. 1-19.*

Office Action from Russian Application No. 2011112461/15, dated Mar. 6, 2015.

Adams et al., *Cancer. Chemother. Pharmacol.* 46:263-271, 2000.

Ahmad et al. "Antibody-Targeted Delivery of Doxorubicin Entrapped in Sterically Stabilized Liposomes Can Eradicate Lung Cancer in Mice," *Cancer Research* 53, Apr. 1, 1993, 1484-1488.

(56) References Cited

OTHER PUBLICATIONS

Author Unknown, "From Antinutrient to Phytonutrient: phytic acid gains respect." HighBeam Research, Environmental Nutrition, Apr. 1, 2004, 2 printed pages. URL: http://www.highbeam.com/doc/1G1-116341390.html/print (accessed Nov. 4, 2011).
Bobo et al., "Convection-enhanced delivery of macromolecules in the brain", PNAS 91:2076-2080, 1994.
Boman et al., "Optimization of the retention properties of vincristine in liposomal system", *Biochimica et Biophysica Acto*, 1152:253-258 (1993).
CAS Registry Record for 23214-92-8 (doxorubicin), entered STN Nov. 16, 1984.
CAS Registry Record for 97682-44-5 (irinotecan), entered STN Aug. 18, 1985.
Chou et al., "Effect of Composition on the Stability of Liposomal Irinotecan Prepared by a pH Gradient Method", *J. Bioscience and Bioengineering*, 95(4):405-408, 2003.
Colbern et al., "Encapsulation of the Topoisomerase I Inhibitor GL147211C in Pegylated (STEALTH) Liposomes: Pharmacokinetics and Antitumor Activity in HT29 Colon Tumor Xenografts", *Clin. Cancer Research* 4:3077-3082, 1998.
Dickinson et al., "Canine model of convection-enhanced delivery of liposomes containing CPT-11 monitored with real-time magnetic resonance imaging", *J. Neurosurg* 108:989-998, 2008.
Dickinson et al., "Canine spontaneous glioma: A translational model system for convection-enhanced delivery", Neuro-Oncology 10:1093, 1-13, 2010.
Drummond et al., "Development of a Highly Active Nanoliposomal Irinotecan Using a Novel Intraliposomal Stabilization Strategy", *Cancer Res* 66(6):3271-3277, 2006.
Emerson et al., "Antitumor Efficacy, Pharmacokinetics, and Biodistribution of NX 211: A Low-Clearance Liposomal Formulation of Lurtotecan", *Clinical Cancer Research* 6:2903 2912,2000.
Grahn et al., "Non-PEGylated liposomes for convection-enhanced . . . experience", *J. Neurooncol* 95:185-197, 2009.
Haran et al., "Transmembrane ammonium sulfate gradients in liposomes produce efficient and stable entrapment of amphipathic weak bases", *Biochimica et Biophysica Acta*, 1151:201-215, 1993.
Hattori et al., "Novel irinotecan-loaded liposome using phytic acid with high therapeutic efficacy for colon tumors", *J. of Controlled Release* 136:30-37, 2009.
Hong et al. "Anti-HER2 Immunoliposomes for Targeted Drug Delivery, Annals of the New York Academy of Sciences." vol. 886, pp. 293-296. Dec. 1999.
Huang, et al. "Use of ammonium sulfate gradient method in the preparation of long circulating mitoxantrone liposomes", Chinese Pharmaceutical Journal, vol. 37, No. 12, pp. 917-919 (Dec. 31, 2002).
Katsu et al., "Ion-Selective Electrode for Transmembrane pH Difference Measurements", *Anal. Chem.* 73:1849-1854, 2001.
Kirpotin et al., "Sterically Stabilized Anti-HER2 Immunoliposomes: Design and Targeting to Human Breast Cancer Cells in Vitro", Biochemist 36:66-75, 1997.
Ko et al., "A Multinational Phase II Study of PEP02 (MM-398), Liposome Irinotecan, for Patients with Gemcitabine-refractory Metastatic Pancreatic Cancer," *Suppl. Abstract* 4069. (2011).
Krauze et al., Convection-enhanced delivery of nanoliposomal CPT-11 (irinotecan) and PEGylated liposomal doxorubicin (doxil) in rodent intracranial brain tumor xenografts, *Neuro-Oncology*, pp. 393-403, Oct. 2007.
Lee et al. "Novel Chondroitin Sulfate binding Cationic Liposomes Loaded with Cisplatin Efficiently Suppress the Local Growth and Liver Metastasis of Tumor Cells in Vivo," *Cancer Research* 62, Aug. 1, 2002, 4282-4288.
Liu et al., "A Versatile Prodrug Approach for Liposomal Core-Loading of Water-Insoluble Camptothecin Anticancer Drugs", *J. Am. Chem. Soc.* 124:7650-7651, 2002.
Maddison et al. "Small Animal Clinical Pharmacology." 2002. p. 474.
Mamot et al., "Extensive distribution of liposomes in rodent brains and brain tumors following convection-enhanced delivery", *J. Neuro-Oncology* 68:1-9, 2004.
Maurer-Spurej et al., "Factors influencing uptake and retention of amino-containing drugs in large unilamellar vesicles exhibiting transmembrane pH gradients", *Biochemica et Biophysics Acta* 1416:1-10, 1999.
Mayer et al., *Cancer Research* 49:5922-5930, 1989.
Messerer et al., "Liposomal Irinotecan: Formulation Development and Therapeutic Assessment in Murine Xenograft Models of Colorectal Cancer", *Clinical Cancer Research* 10:6638-6649 2004.
Miles et al. "Combination Versus Sequential Single-Agent Therapy in Metastatic Breast Cancer," *The Oncologist*, 7(suppl 6), 2002, pp. 13-19.
Morrison et al., "Focal delivery during direct infusion to brain: role of flow rate, catheter diameter, and tissue mechanics", *Am. J. Physiol. Regulatory Integrative Comp. Physiol.* 277:1218-1229 1999.
Morrison et al., High-flow Microinfusion: Tissue Penetration and Pharmacodynamics, *Am. J. Physiol.*, 266:R292-R305,1994.
Nentwich, PF. "Intravenous Therapy." 1990. p. 310.
Neve et al., "Biological Effects of Anti-ErbB2 Single Chain Antibodies Selected for Internalizing Function", *Biochemical and Biophysical Research Communications*, 280:274-279 (2001).
Nielsen et al., "Therapeutic efficacy of anti-ErbB2 immunoliposomes targeted by a phage antibody selected for cellular endocytosis", *Biochimica et Biophysica Acta*, 1591:109-118 (2002).
Noble et al., "Novel Nanoliposomal CPT-11 Infused by Convection-Enhanced Delivery in Intracranial Tumors: Pharmacology and Efficacy", *Cancer Res.*, 66(5):2801-2806, 2006.
Ochi et al., "Crystalline Salts of Sucrose Octasulfate", *Pharmaceutical Society of Japan* 28:638-641, 1980.
PharmaEngine, Inc. and Merrimack Pharmaceuticals, Inc. Enter into a Licensing and Collaboration Agreement on PEP02 (MM-398), Nanoliposomal Irinotecan, Press Release May 9, 2011.
Pharmaengine, www.pharmaengine.com/pep02.html Webpage titled "PEP02". Aug. 4, 2011.
Paul et al., "Selection of Tumor-Specific Internalizing Human Antibodies from Phage Libraries", *J. Mol. Biol.*, 301:1149-1161 (2000).
Ramsay et al., "A Novel liposomal irinotecan formulation with significant . . . to improve drug retention", European *J. of Pharmaceutics and Biopharmaceutics* 68:607-617, 2008.
Sadzuka et al. "Effect of Liposomalization on the Antitumor Activity, Side-Effects, and Tissue Distribution of CPT-11," Cancer Letters 127 (1998) 99-106.
Saito et al., "Convection-enhanced delivery of Ls-TPT enables an effective, continuous, low-dose chemotherapy against malignant glioma xenograft model", *Neuro-Oncology*, pp. 205-214 2006.
Saito et al., "Distribution of Liposomes into Brain and Rat Brain Tumor Models by Convection-Enhanced Delivery Monitored with Magnetic Resonance Imaging", *Cancer Research* 64:2572-2579 2004.
Saito et al., Tissue affinity of the infusate affects the distribution volume during convection-enhanced delivery into rodent brans: Implications for local drug delivery, *J. Neuroscience Methods* 154:225-232, 2006.
Shimada et al. "Irinotecan Plus Low-Dose Cisplatin for Alpha Fetoprotein-Producing Gastric Carcinoma with Multiple Liver Metastases: Report of Two Cases," *Surg Today* (2002) 32:1075 1080.
Tardi et al., Liposomal Encapsulation of Topotecan Enhances Anticancer Efficacy in Murine and Human Xeno raft Models, *Cancer Research* 60:3389-3393, 2000.
Werbel et al., "Basically Substituted Ellipticine Analogues as Potential Antitumor Agents", *J. Med. Chem.* 29:1321-1322, 1986.
Yamashita et al., "Convection-enhanced delivery of a topoisomerase I inhibitor (nanoliposomal topotecan) and topoisomerase II inhibitor (pegylated liposomal doxorubicin) in intracranial brain tumor xeon rafts" *Neuro-Oncology* 8:1-9 2006.
Yeh et al. "Structural Basis for Activation of Fibroblast Growth Factor Signaling by Sucrose Octasulfate," *Molecular and Cellular Biology*, vol. 22 No. 20, Oct. 2002, pp. 7184-7192.

(56) References Cited

OTHER PUBLICATIONS

Yu, et al, "The method of improving entrapment efficiency of liposomes and its research progress", Chinese Journal of Pharmaceuticals, vol. 33, No. 11, pp. 564-568 (Dec. 31, 2002).
Zhu et al., *Cancer Chemotherapy & Pharmacology*, 39:138-142 1996.
International Search Report mailed on Aug. 18, 2005, for PCT Patent Application No. PCT/US2005/015349, 3 pages.
Written Opinion of the International Searching Authority mailed on Aug. 18, 2005, for PCT Patent Application No. PCT/US2005/015349, 6 pages.
European Search Report mailed on Sep. 1, 2010, for EP Patent Application No. 05745505.7, 6 pages.
Berge, Stephen, et al, "Pharmaceutical Salts", Journal of Pharmaceutical Sciences, vol. 66, No. 1, Jan. 1977.
Chou et al., Science Direct Abstract of "Effect of Composition on the Stability of Liposomal Irinotecan Prepared by a pH Gradient Method", J. Bioscience and Bioengineering, 95(4):405-408, accessed Mar. 7, 2016, 1 printed page.
Vucenik, Ivan, et al. "Cancer Inhibition by Inositol Hexaphosphate (IP6) and Inositol: From Laboratory to Clinic," American Society for Nutritional Sciences, 2003.
Yuan, Huang, et al. English Abstract of "Studies on preparation of long circulating mitoxantrone liposomes with transmembrane ammonium sulfate gradients", Chinese Pharmaceutical Journal, vol. 37, No. 12, pp. 917-919 (Dec. 31, 2002).
Yu, et al. "The method of improving entrapment efficiency of liposomes and its research progress", Chinese Journal of Pharmaceuticals, vol. 33, No. 11, pp. 564-568 (Dec. 31, 2002). Only Abstract in English.

\* cited by examiner

LIPOSOMES USEFUL FOR DRUG DELIVERY

STATEMENT OF PRIORITY

This application is a continuation of U.S. application Ser. No. 14/632,422, filed Feb. 26, 2015, which is a divisional of U.S. application Ser. No. 14/175,365, filed Feb. 7, 2014, which is a continuation of U.S. application Ser. No. 13/654, 373, filed Oct. 17, 2012, which is a continuation of U.S. application Ser. No. 13/416,204, filed Mar. 9, 2012, which is a continuation of U.S. application Ser. No. 11/121,294, filed May 2, 2005, which claims benefit of priority of U.S. Provisional Patent Application No. 60/567,921, filed on May 3, 2004, all of which are incorporated herein by reference in their entirety for all purposes.

FIELD OF THE INVENTION

This invention relates generally to the field of liposomes, and more specifically to liposome compositions useful for delivery of therapeutic or diagnostic entities.

BACKGROUND OF THE INVENTION

Liposomes, or lipid bilayer vesicles, have been used or proposed for use in a variety of applications in research, industry, and medicine, particularly for the use as carriers of diagnostic or therapeutic compounds in vivo. See, for example: Lasic, D. *Liposomes: from physics to applications*. Elsevier, Amsterdam, 1993. Lasic, D, and Papahadjopoulos, D., eds. *Medical Applications of Liposomes*. Elsevier, Amsterdam, 1998. Liposomes are usually characterized by having an interior space sequestered from an outer medium by a membrane of one or more bilayers forming a microscopic sack, or vesicle. Bilayer membranes of liposomes are typically formed by lipids, i.e. amphiphilic molecules of synthetic or natural origin that comprise spatially separated hydrophilic and hydrophobic domains. See Lasic D., 1993, supra. Bilayer membranes of the liposomes can be also formed by amphiphilic polymers and surfactants (polymerosomes, niosomes). A liposome typically serves as a carrier of an entity such as, without limitation, a chemical compound, a combination of compounds, a supramolecular complex of a synthetic or natural origin, a genetic material, a living organism, a 20325081.1 portion thereof, or a derivative thereof, that is capable of having a useful property or exerting a useful activity. For this purpose, the liposomes are prepared to contain the desired entity in a liposome-incorporated form. The process of incorporation of a desired entity into a liposome is often referred to as "loading". The liposome-incorporated entity may be completely or partially located in the interior space of the liposome, within the bilayer membrane of the liposome, or associated with the exterior surface of the liposome membrane. The incorporation of entities into liposomes is also referred to as encapsulation or entrapment, and these three terms are used herein interchangingly with the same meaning. The intent of the liposomal encapsulation of an entity is often to protect the entity from the destructive environment while providing the opportunity for the encapsulated entity to exert its activity mostly at the site or in the environment where such activity is advantageous but less so in other sites where such activity may be useless or undesirable. This phenomenon is referred to as delivery. For example, a drug substance within the liposome can be protected from the destruction by enzymes in the body, but become released from the liposome and provide treatment at the site of disease.

Ideally, such liposomes can be prepared to include the desired compound (i) with high loading efficiency, that is, high percent of encapsulated entity relative to the amount taken into the encapsulation process; (ii) high amount of encapsulated entity per unit of liposome bilayer material; (iii) at a high concentration of encapsulated entity, and (iv) in a stable form, i.e., with little release (leakage) of an encapsulated entity upon storage or generally before the liposome appears at the site or in the environment where the liposome-entrapped entity is expected to exert its intended activity.

Therefore, there is a need in the art to provide various liposome compositions that are useful for delivery of a variety of compounds, especially therapeutic, diagnostic, or imaging entities.

SUMMARY OF THE INVENTION

The present invention is based on the discovery that substituted ammonium and polyanion are useful for loading and retaining entities inside liposomes. Accordingly the present invention provides methods and liposome compositions useful for delivery of a variety of entities, especially therapeutic entities, that is, entities useful in the diagnosis, prognosis, testing, screening, treatment, or prevention of an undesirable condition, e.g., a disease, in living organism, such as a human, a plant, or an animal.

In one embodiment, the present invention provides a composition comprising a liposome in a medium, wherein the inside of the liposome contains a substituted ammonium

wherein each of $R_1$, $R_2$, $R_3$, and $R_4$ is independently a hydrogen or an organic group having, inclusively, in totality up to 18 carbon atoms, wherein at least one of $R_1$, $R_2$, $R_3$, and $R_4$ is an organic group, wherein the organic group is independently a hydrocarbon group having up to 8 carbon atoms, and is an alkyl, alkylidene, heterocyclic alkyl, cycloalkyl, aryl, alkenyl, or cycloalkenyl group or a hydroxy-substituted derivative thereof, optionally including within its hydrocarbon chain a S, O, or N atoms, forming an ether, ester, thioether, amine, or amide bond, wherein at least three of $R_1$, $R_2$, $R_3$, and $R_4$ are organic groups, or the substituted ammonium is a sterically hindered ammonium, such as, for example, where at least one of the organic groups has a secondary or tertiary carbon atom directly linked to the ammonium nitrogen atom. Preferably, the substituted ammonium compound encapsulated into liposomes has a negative logarithm of the acidic (deprotonation) dissociation constant (pKa) of at least about 8.0, at least about 8.5, at least about 9.0, at least 9.5, or at least 10.0, as determined in an aqueous solution at ambient temperature.

In another embodiment, the present invention provides a composition comprising a liposome in a medium, wherein the inner space of the liposome contains a polyanion and wherein the polyanion is a polyanionized polyol or a polyanionized sugar. The liposome preferably contains a transmembrane gradient capable of effecting the loading of an entity into the liposome. In one embodiment, the transmembrane gradient is a gradient of an ammonium, a quarternary ammomium, or a primary, secondary, or tertiary substituted ammonium compound having in a diluted aqueous solution at ambient temperature a negative logarithm of the acidic (deprotonation) dissociation constant (pKa) of at least about 8.0, at least about 8.5, at least about 9.0, at least 9.5, or at least 10.0. The liposome optionally contains an entrapped entity, for example, a therapeutic, a detectable marker, or a globally cationic organic molecule.

In yet another embodiment, the composition provided by the present invention further comprises an entity encapsulated in the liposomes of the present invention. Preferably, the entity is encapsulated within the inner space of the liposome. For example, the inner space of the liposome further comprises an anti-neoplastic therapeutic and wherein the toxicity level of the composition to a subject is at least equal to or less than the toxicity level of the anti-neoplastic therapeutic administered to the subject without the composition.

In yet another embodiment, the composition provided by the present invention is a liposome composition comprising a camptothecin compound. The composition has an anticancer activity at least two times, four times, or ten times higher than the camptothecin compound similarly administered in the absence of the composition, while the toxicity of the composition does not exceed, is at least two times, or at least four times lower than the toxicity of the camptothecin compound similarly administered in the absence of the composition. In a one embodiment, the camptothecin compound is a pro-drug, and is contained in the liposome of at least 0.1 mg, at least 0.2 mg, at least 0.3 mg, at least 0.5 mg, or at least 1 mg per 1 mg of the liposome membrane materials, e.g., lipids. The camptothecin compound is preferably encapsulated in the liposome substantially within the inner space of the liposome. In one instance, the camptothecin compound is irinotecan (CPT-11).

In yet another embodiment, the composition provided by the present invention is a liposome composition of a vinca alkaloid or a derivative thereof. The composition has the 24-hour drug retention within the liposome after 24 hours exposure in the blood of a mammal in vivo of at least 50%, at least 60%, or at least 70% of the original drug load. The vinca alkaloid or a derivative thereof is preferably encapsulated in the liposome substantially within the inner space of the liposome. One example of the mammal is a rat. Exemplary vinca alkaloids and derivatives are vincristine, vinblastine, and vinorelbine.

In still another embodiment, the present invention provides a method of encapsulating an entity into a liposome. The method comprises contacting the liposomes of the present invention with an entity, e.g., therapeutic or detectable entity. Preferably, the contacting is performed under the conditions when the concentration of substituted ammonium or a polyanion of the present invention in the medium is lower than that in the inner space of the liposomes. In one embodiment, the liposome composition is contacted with an entity in an aqueous medium.

In still another embodiment, the present invention provides a method of encapsulating an entity into a liposome. The method comprises contacting the liposome-containing composition of the present invention with a pre-entity, wherein the pre-entity is capable of being converted to an entity under a condition, and providing the condition inside the liposome whereby converting the pre-entity to the entity inside the liposome. In one case, the entity is an organic compound, and the pre-entity is a basic derivative thereof.

In still another embodiment, the present invention provides a kit for making liposome-encapsulated entities. The kit comprises a container with a liposome of the present invention, and, optionally, a container containing an entity, and/or instructions for a user, e.g. to encapsulate an entity.

DESCRIPTION OF THE PREFERRED EMBODIMENTS

Figure 1:
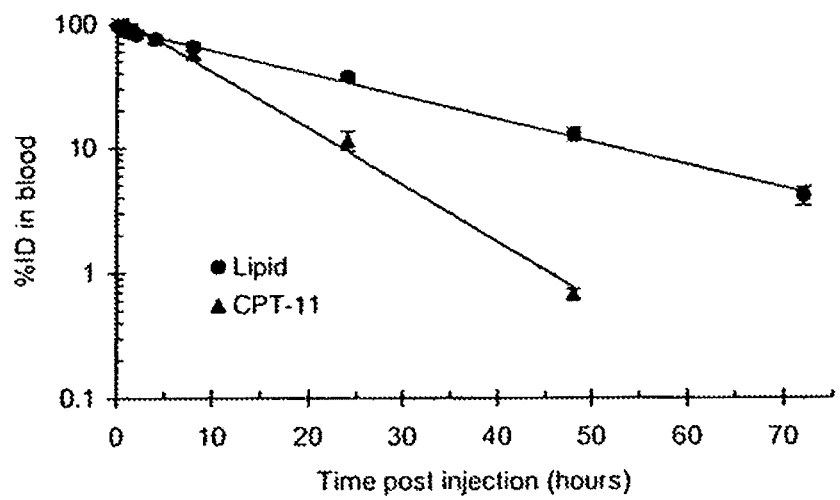
FIG. 1 shows blood pharmacokinetics of the liposome lipid (circles) and the drug (triangles) after i.v. bolus administration of CPT-11-loaded liposomes to a rat. The liposomes are loaded using TEA-Pn method (See Example 9).

The present invention relates in general to methods and liposome compositions useful for delivery a variety of entities, especially therapeutics and imaging agents. It is the discovery of the present invention that substituted ammonium and polyanion are useful for loading and retaining the entities, e.g., compound, inside liposomes. Accordingly, the present invention provides liposome compositions and kits containing substituted ammonium and/or polyanion and methods of making these liposome compositions.

According to one feature of the present invention, it provides a composition of liposomes containing within its inner space one or more substituted ammonium compounds of a formula

(I)

wherein each of $R_1$, $R_2$, $R_3$, and $R_4$ is independently a hydrogen or an organic group, and wherein at least one of $R_1$, $R_2$, $R_3$, and $R_4$ is an organic group, such as, an alkyl, alkylidene, heterocyclic alkyl, cycloalkyl, aryl, alkenyl, or cycloalkenyl group, a hydroxy-substituted derivative thereof, optionally including within its hydrocarbon chain a S, O, or N atoms, e.g., forming an ether (including an acetal or ketal), ester, sulfide (thioether), amine, or amide bond therein. If less than three of $R_1$, $R_2$, $R_3$, and $R_4$ are organic groups, then, according to the invention, at least one, and preferably two, of the organic groups has a secondary or tertiary carbon atoms (i.e., carbon atoms having 2 or 3 carbon-carbon bonds, respectively) directly linked to the ammonium nitrogen, i.e., the substituted ammonium is a sterically hindered ammonium. Generally, the presence of titratable ammonium, such as unsubstituted ammonium ion ($NH_4^+$), as well as primary and secondary straight chain alkylammonium ions in the inner space of the liposome of the present invention is known to provide for enhanced encapsulation of weak amphiphilic bases, for example, via a mechanism of "active", "remote", or "transmembrane gradient-driven" loading (Haran, et al., *Biochim. Biophys. Acta*, 1993, v. 1152, p. 253-258; Maurer-Spurej, et al., *Biochim. Biophys. Acta*, 1999, v. 1416, p. 1-10). However these ammonia compounds possess hydrogen atoms that easily enter into reactions of nucleophilic substitution, and otherwise react chemically with the liposome-entrapped entities, and therefore are capable of impairing the chemical integrity of the entitites during or after the liposome loading (entrapment) process. Thus, it is desirable for an entrapped substituted ammonium compound to be more chemically inert, lacking chemical functions which are unstable or readily reactive with the liposome components, that may include an encapsulated entity. Unexpectedly, we discovered that liposome compositions comprising within their inner space a substituted tertiary and quaternary ammonium that do not have a substitutable hydrogen, or a sterically hindered primary or secondary ammonium, in which the access to an ammonium hydrogen atom is sterically hindered by a neighbor bulky organic group, such as having one or two secondary or tertiary carbon atoms linked to the ammonium nitrogen, show not only outstanding entity-loading capacity, but also improved stability of the liposome-entrapped entity, e.g., a drug, against premature release from the liposome in the living body.

In one embodiment, the liposome-entrapped substituted ammonium compound is pharmaceutically inert, that is, does not elicit an adverse physiological response when administered to a living subject, e.g. a human or an animal, within an amount of the liposome membrane material that is sufficient to deliver an effective dose of the liposome-entrapped entity. In another embodiment, the substituted ammonium of the present invention has an acceptable level of toxicity to a subject. Usually an acceptable level of toxicity means that the toxic dose, e.g., a maximum tolerated dose (MTD), or a dose causing 50% lethality (LD50) of the substituted ammonium of the present invention is at least twice, at least four times, at least eight times, or at least ten times higher than the toxic dose of a liposome-entrapped entity, e.g., drug, loaded inside the liposomes of the present invention. For example, triethylammonium sulfate has an acceptable level of toxicity according to the present invention since its LD50 is about 40 times higher than the LD50 of doxorubicin, an anti-cancer drug. The toxicity levels or physiological responses of substituted ammoniums, as well as of the entities of interest, if not already known, can be readily established via routine techniques well known by persons skilled in the biomedical art. See, for example, S. C. Gad. *Drug Safety Evaluation*, Wiley, New York, 2002. One method of quantifying the toxicity of free and/or liposomally formulated drug is described in Example 16 herein.

In one preferred embodiment, the substituting organic groups among $R_1$, $R_2$, $R_3$, or $R_4$ are of the size and physicochemical properties sufficient to ensure that the substituted ammonium forms in aqueous environment substantially a true (molecular) solution, but not micelles, bilayers, or similar self-assembled structures. Therefore, the substituted ammonium of the present invention preferably has little or substantially no distribution into the bilayer portion of liposomes, therefore minimizing the risk of destabilization, solubilization, or permeabilization of the liposomes entrapping the substituted ammonium.

The organic group of the substituted ammonium is typically a hydrocarbon containing, inclusively, up to 8 carbon atoms, up to 6 carbon atoms, or up to 4 carbon atoms, and in totality, the substituting groups contain, inclusively, up to 18, up to 16, up to 12, or up to 9 carbon atoms. These substituting hydrocarbon groups include any combination of interlinked primary, secondary, or tertiary carbon atoms, as well as cycloalkyl groups being linked at their termini directly to the ammonium nitrogen to form a heterocycle, or to a carbon atom of an ammonium hydrogen-substituting group. These substituted alkyl groups can also include heteroatoms, e.g., oxygen, nitrogen, or sulfur in their carbon chains forming a functional group, e.g., ether, acetal, amine, or sulfide group, as well as forming a functional group, e.g., hydroxyl group, linked to the alkyl carbon chain. Examples of the organic group of the present invention include, without any limitation, alkyls, alkylidenes, heterocyclic alkyls, cycloalkyls, aryls, alkenyls, cycloalkenyls, or hydroxy-substituted derivatives thereof, e.g., a hydroxy-substituted alkylidene forming a ring inclusive of N in the substituted ammonium.

In another embodiment, the substituted ammonium is: a heterocyclic ammonium, i.e. an ammonium wherein at least two of $R_1$, $R_2$, $R_3$, or $R_4$ form a ring; a sterically hindered primary ammonium; or a sterically hindered secondary ammonium. In general, a sterically hindered primary or secondary ammonium includes any substituted ammonium with one or two of the $R_1$, $R_2$, $R_3$, and $R_4$ substituted with alkyl groups that sterically crowd the molecule, e.g., any substituted ammonium with one or two of the $R_1$, $R_2$, $R_3$, and $R_4$ substituted with one or two cycloalkyl groups or alkyl groups having at least one secondary or tertiary alkyl carbon atom linked to the nitrogen of the substituted ammonium. Examples of such heterocyclic, sterically hindered primary ammoniums, and sterically hindered secondary ammonium include, without any limitation, isopropylethylammonium, isopropylmethylammonium, diisopropylammonium, tert-butylethylammonium, dicychohexylammonium, protonized forms of morpholine, pyridine, piperidine, pyrrolidine, piperazine, tert-bulylamine, 2-amino-2-methylpropanol-1,2-amino-2-methyl-propandiol-1,3, and tris-(hydroxyethyl)-aminomethane. These substituted ammonium compounds are generally commercially available in the form of various salts, or are readily prepared from their corresponding amines by neutralization with acids.

In yet another embodiment, the substituted ammonium is a tertiary or quaternary ammonium including, without any limitation, trimethylammonium, triethylammonium, tributylammonium, diethylmethylammonium, diisopropylethylammonium, triisopropylammonium, N-methylmorpholinium, N-hydroxyethylpiperidinium, N-methylpyrrolidinium, and N,N'-dimethylpiperazinium, tetramethylammonium, tetraethylammonium, and tetrabutylammonium. These substituted ammonium compounds are generally commercially available in the form of various salts, or are readily prepared from their corresponding amines by neutralization with acids.

In yet another embodiment, the substituted ammonium compound according to the invention is a globally cationic compound, that is, under the conditions of the entity encapsulation, typically, in aqueous solution at a pH between about pH 2 and about pH 8, bears net positive charge, e.g. as a result of ionization (protonation) of the nitrogen atom.

In yet another embodiment, the substituted primary, secondary, or tertiary ammonium compound encapsulated into liposomes has a negative logarithm of the acidic (deprotonation) dissociation constant (pKa) of at least about 8.0, at least about 8.5, at least about 9.0, at least 9.5, or at least about 10.0, as determined in a diluted aqueous solution at ambient temperature (typically 25° C.). Parameter pKa is a well known characteristic of ammonium compounds that generally characterizes the strength of their basic properties, and methods for pKa determination are conventional and routine in the art. The pKa values for many amines and their protonated forms (ammoniums) are tabulated in reference books of chemistry and pharmacology. See, for example, IUPAC Handbook of Pharmaceutical Salts, ed. by P. H. Stahl and C. G Wermuth, Wiley-VCH, 2002; CRC Handbook of Chemistry and Physics, 82nd Edition, ed. by D. R. Lide, CRC Press, Florida, 2001, p. 8-44 to 8-56. Generally, higher pKa characterizes stronger bases. Exemplary substituted ammonium compounds, as well as unsubstituted ammonium (listed as their conjugated amine bases) have the following pKa values: pyrrolidine, 11.31; piperidine, 11.12; diisopropylamine, 11.05; diethylamine, 10.93; triethylamime, 10.75; dimethylamine, 10.73; tert-butylamine, 10.68; cyclohexylamine, 10.66; methylamine, 10.66; ethylamine, 10.65; propylamine, 10.54; Isopropylamine, 10.53; N-ethylpiperidine, 10.45; dicyclohexylamine, 10.4; N-methylpiperidine, 10.38; diethylmethylamine, 10.35; dimethylpropylamine, 10.15; trimethylamine, 9.8; piperazine, 9.73 (I), 5.33 (II); 2-amino-2-methylpropanol, 9.69; N,N'-dimethylpiperazine, 9.66 (I), 5.2 (II); diethyl-(2-hydroxyethyl)amine, 9.58; ethanolamine, 9.5; N-hyrdoxyethylpyrrolidine, 9.44; diethanolamine, 9.28; ammonia, 9.27; dimethyl-(2-hydroxyethyl)amine, 8.83; 2-amino-2-methylpropanediol-1,3, 8.3; morpholine, 8.5; tris-(hydroxymethyl)-aminomethane, 8.3; N-methylglucamine, 8.03; triethanolamine, 7.76; N-ethylmorpholine, 7.67; N-hydroxyethylmorpholine, 7.39; imidazole, 7.03; pyridine, 5.23. As a rule, substitution of alkyl or cycloalkyl group for a hydrogen in an ammonium compound increases pKa value. Notably, multiple hydroxyl or ether functions in the substituting alkyl groups, or the presence of aromaticity in a nitrogen-containing heterocyclic group reduce pKa value relative to similar substituted ammonia without hydroxyl or ether functions. The compounds with more than one ammonium group usually have pKa of the second and subsequent ammonium group much lower than of the first one. We unexpectedly discovered that substituted ammonia with higher pKa values, that is, formed by more strongly basic amines, were more effective than those formed from weaker amines in stabilizing the drug inside liposomes. For example, both IHP and SOS salts of triethylammonium (pKa=10.75) were notably more effective than corresponding salts of triethanolammonium (pKa=7.76) in stabilizing irinotecan within the liposomes in vivo (Example 73).

The substituted ammonium contained in the liposome composition of the present invention can be in any suitable form, e.g., salt. Suitable salts include pharmaceutically acceptable salts. See, for example, P. H. Stahl, C. G. Wermuth (eds), Handbook of Pharmaceutical Salts, Wiley-VCH, Weinheim, 2002. In one embodiment, the substituted ammonium is a salt containing one or more polyanions of the present invention. Optimally the counter-ion (anion) in the substituted ammonium salt of the present invention renders the salt water soluble, is pharmaceutically inert, capable of forming precipitates or gels when in contact with a therapeutic or detectable entity, and/or is less permeable through the liposome membrane than the substituted ammonium or its non-dissociated amine form. In general, the substituted ammonium salt of the present invention forms a true solution in the intraliposomal, e.g. aqueous, space, and does not form a significant amount of a condensed phase such as micelle, bilayer, gel, or crystalline phase. The relative amount of a substituted ammonium and a salt-forming anion, e.g., polyanion, is at or near the point of stiochiometric equivalency, and typically has the pH on the range of 3-9, more often, pH 4-8, dependent, for example, on the dissociation constant of the conjugated base of the substituted ammonium ion.

In general, the substituted ammonium is contained inside, that is, in the inner (interior) space of the liposomes of the present invention. In one embodiment, the substituted ammonium is partially or substantially completely removed from the outer medium surrounding the liposomes. Such removal can be accomplished by any suitable means known to one skilled in the art, e.g., dilution, ion exchange chromatography, size exclusion chromatography, dialysis, ultrafiltration, precipitation, etc.

According to another feature of the present invention, it provides a composition of liposomes containing a polyanion. The polyanion of the present invention can be any suitable chemical entity with more than one negatively charged groups resulting in net negative ionic charge of more than two units within the liposome interior, e.g., aqueous, space. The polyanion of the present invention can be a divalent anion, a trivalent anion, a polyvalent anion, a polymeric polyvalent anion, a polyanionized polyol, or a polyanionized sugar. Sulfate, phosphate, pyrophosphate, tartrate, succinate, maleate, borate, and citrate are, without limitation, the examples of such di- and trivalent anions. In one preferred embodiment, the polyanion of the present invention is a polyanionic polymer, having an organic (carbon) or inorganic backbone, and a plurality of anionic functional groups, i.e functional groups ionizable to a negative charge in a neutral aqueous solution, and integrated or appended to the backbone. A polymer is a natural or synthetic compound, usually of high molecular weight, consisting of repeated linked units, each a relatively light and simple molecule. Exemplary polyanionic polymers are polyphosphate, polyvinyl sulfate, polyvinylsulfonate, anionized polyacrylic polymers, anionized, e.g., polysulfonated polyamines, such as polysulfonated poly(ethylene imine); polysulfated, polycarboxylated, or polyphosphorylated polysaccharides; acidic polyaminoacids; polynucleotides; other polyphosphorylated, polysulfated, polysulfonated, polyborated, or polycarboxylated polymers. Such polyvalent anions and polymers are well known in the art and many are commercially available. A polymeric anion of the present invention is preferably a biodegradable one, that is, capable of breaking down to non-toxic units within the living organism. Exemplary biodegradable polymeric anion is polyphosphate.

In another preferred embodiment, the polyanion is a polyanionized polyol or a polyanionized sugar. A polyol is an organic molecule having a plurality of hydroxyl groups linked to, e.g., linear, branched, or cyclic, carbon backbone. Thus, a polyol can be characterized in other terms as a polyhydroxylated compound. Preferably, a majority of carbon atoms in a polyol are hydroxylated. Polyols (polyatomic alcohols) are molecules well known in the art. Both straight chain (linear or branched) and cyclic polyols can be used. Exemplary polyols of the present invention are, without limitation: ethyleneglycol; glycerol, treitol, erythritol, pentaerythritol, mannitol, glucitol, sorbitol, sorbitan, xylitol, lactitol, maltitol, fructitol, and inositol. A sugar usually comprises a cyclic acetal, a cyclic ketal, a ketone, or an aldehyde group, or an adduct thereof, within a group of interlinked predominantly hydroxylated carbon atoms. Sugars are often naturally occurring compounds. Hydrolysis of sugars in aqueous medium leads to units called monosaccharides. Typically, in an aqueous solution a monosaccharide sugar molecule of five or six carbon atoms forms a cyclic hemiacetal, a ring structure. Preferably, sugars of the present inventions are monosaccharides or disaccharides, that is, consist of one or two monosaccharide units, each having from three to seven, preferably from three to six carbon atoms. Exemplary sugars of the present invention are, without limitation, monosacharide hexoses, such as glucose (dextrose), galactose, mannose, fructose; monosaccharide pentoses, such as xylose, ribose, arabinose, and disaccharides, such as lactose, trehalose, sucrose, maltose, and cellobiose. Compounds comprised of several interlinked sugar units forming a ring (cyclodextrins) and their derivatives can be also used. Reduction of sugars is one method to obtain polyols. More stable "non-reducing" and non-metabolizable disaccharides, such as sucrose or trehalose, are preferred. Various polyols, monosaccharides, and disaccharides are commercially available.

A polyanionized polyol or sugar is a polyol or a sugar having its hydroxyl groups completely or partially modified or replaced with anionic groups (anionized). Thus, a polyanionized polyol or polyanionized sugar comprises a polyol moiety or a sugar moiety along with anionic groups linked thereto. Exemplary anionic groups include, without any limitation, carboxylate, carbonate, thiocarbonate, dithiocarbonate, phosphate, phosphonate, sulfate, sulfonate, nitrate, and borate. It is preferred that at least one anionic group of a polyanionized sugar or polyol is strongly anionic group, that is, is more than 50% ionized in the broad range of pH, e.g., pH 3-12, preferably, pH 2-12, when in the aqueous medium, or, alternatively, has a log dissociation constant ($pK_a$) of 3 or less, preferably of 2 or less. Polyanionization of a polyol or a sugar can be achieved by a variety of chemical processes well known in the art. For example, reaction of polyols and/or sugars with sulfur trioxide or chlorosulfonic acid in pyridine or 2-picoline results in some or all hydroxyl groups esterified with sulfuric acid residues (sulfated), providing for a polysulfated sugar or polyol. Exemplary sulfated sugar of the present invention is sulfated sucrose including, without limitation, sucrose hexasulfate, sucrose heptasulfate, and sucrose octasulfate (See Ochi. K., et al., 1980, Chem. Pharm. Bull., v. 28, p. 638-641). Similarly, reaction with phosphorus oxychloride or diethylchlorophosphate in the presence of base catalyst results in polyphosphorylated polyols or sugars. Polyphosphorylated polyols are also isolated from natural sources. For example, inositol polyphosphates, such as inositol hexaphosphate (phytic acid) is isolated from corn. A variety of sulfated, sulfonated, and phosphorylated sugars and polyols suitable to practice the present invention are disclosed, e.g., in U.S. Pat. No. 5,783,568 and U.S. Pat. No. 5,281,237, which are incorporated herein by reference. It was unexpectedly discovered that polyanionised polyhydroxylated compounds with only strong acid dissociation steps, e.g. the groups having pKa of less than about 3.0, preferably less than about 2.0, such as, for example, sulfate monoesters (pKa 1.0 or less), provide liposomal encapsulation with better drug retention than polyanionized polyhydroxylated compounds having also weakly acidic dissociation steps, such as phosphate monoesters (step 1, pKa about 1.5; step 2, pKa about 6.7; see Stahl and Wermuth, Op. cit., 2002). Example 73 below illustrates this discovery. Complexation of polyols and/or sugars with more than one molecule of boric acid also results in a polyanionized (polyborated) product. Reaction of polyols and/or sugars with carbon disulfide in the presence of alkali results in polyanionized (polydithiocarbonated, polyxanthogenate) derivatives. A polyanionized polyol or sugar derivative can be isolated in the form of a free acid and neutralized with a suitable base, for example, with an alkali metal hydroxide, ammonium hydroxide, or preferably with a substituted amine, e.g., amine corresponding to a substituted ammonium of the present invention, in a neat form or in the form of a substituted ammonium hydroxide providing for a polyanionic salt of a substituted ammonium of the present invention. Alternatively, a sodium, potassium, calcium, barium, or magnesium salt of a polyanionized polyol/sugar can be isolated and converted into a suitable form, e.g., a substituted ammonium salt form, by any known method, for example, by ion exchange.

The polyanion of the present invention usually has a charge density of at least two, three, or four negatively charged groups per unit, e.g., per carbon atom or ring in a carbon chain or per monosaccharide unit in a sugar. The polyanionized sugar or cyclic polyol of the present invention preferably has at least 75% of available hydroxyl groups polyanionized, and more preferably 100% of available hydroxyl groups polyanionized. In addition, polyanionization inside the liposomes of the present invention is usually at a level that is compatible with or facilitates the delivery and release of the entity entrapped inside the liposomes at the site of its intended action, but decreases the release of the entrapped entity prematurely, i.e., before the liposome reaches its site of intended action.

According to the present invention, the degree of polyanionization inside the liposomes can be used to regulate the release characteristics, e.g., release rate and kinetics of an entity entrapped inside the liposomes. In general, the degree of polyanionization can be assessed based on the amount of polyanionized sugar or polyol relative to the total amount of anion(s) or in the case of polyanion being the only kind of anion, the percentage of polyanionization with respect to the total polyanionization capacity of the polyanion, e.g., polyanionized sugar or polyol or a mixture thereof inside the liposomes of the present invention. In one embodiment, polyanionized sugar or polyol is mixed with one or more of other anions and the less the amount of polyanionized sugar or polyol over the amount of other anion(s), the faster the entity is released from the liposomes.

Usually if an entrapped entity is released from the liposomes at the site of its intended activity too slowly, the desired entity release rate can be achieved by using a mixture of polyanionized sugar or polyol with one or more other monovalent or polyvalent anions, e.g., chloride, sulfate, phosphate, etc. Alternatively, one can use mixtures of polyanionized sugar or polyols with various degrees of polyanionization. In one embodiment, the degree of polyanionization inside the liposomes of the present invention is between 0.1% to 99%, 10% to 90%, or 20% to 80% of the total anion(s) inside the liposomes, e.g., with an entrapped entity.

In general, the liposome composition of the present invention can contain one or more polyanions of the present invention in any suitable form, e.g., in the form of an acid or a salt comprising a polyanion and a cation. The amount of polyanion, e.g., polyanionized sugar or polyol can be stoichiometrically equivalent to or different from the amount of the cation. In one embodiment, the liposome composition of the present invention contains one or more polyanion salts of a cation, wherein there is a cation concentration gradient or a pH gradient present across the liposome membrane. In another embodiment, the liposome composition of the present invention contains one or more substituted ammonium polyanion salts of the present invention. In yet another embodiment, the liposome composition of the present invention contains the polyanion inside the liposomes while the polyanion in the medium containing the liposomes is partially or substantially removed by any suitable means known to one skilled in the art, e.g., dilution, ion exchange chromatography, size exclusion chromatography, dialysis, ultrafiltration, absorption, precipitation, etc. In still another embodiment, the liposome with entrapped polyanion, e.g., polyanionized polyol or polyanionized sugar, has also a transmembrane gradient effective in retaining substances within the liposome. Examples of such transmembrane gradients are pH gradient, electrochemical potential gradient, ammonium ion gradient, substituted ammonium ion gradient, or solubility gradient. A substituted ammonium gradient typically includes a substituted form of ammonium ion comprising at least one C—N bond, such as, primary, quaternary, tertiary, or quaternary ammonium. Methods of creating transmembrane gradients are routine in the art of liposomes.

According to yet another feature of the present invention, the liposome composition of the present invention contains one or more substituted ammoniums and/or polyanions of the present invention and a chemical or biological entity, e.g., therapeutics or detectable entity. For example, the entity contained in the liposome composition of the present invention can be a therapeutic agent, ink, dye, magnetic compound, fertilizer, lure, biocatalyst, taste or odor modifying substance, bleach, or any entity that is detectable by any suitable means known in the art, e.g., magnetic resonance imaging (MRI), optical imaging, fluorescent/luminescent imaging, or nuclear imaging techniques. Conveniently, an entity contained in or loadable to the liposome composition of the present invention is a weakly basic and membrane-permeable (lipophilic) entity, e.g., an amine-containing or nitrogen base entity.

In one embodiment, the entity contained in the liposome composition of the present invention is a therapeutic agent.

In another embodiment, the entity contained in the liposome composition is an anticancer entity. A partial listing of some of the commonly known commercially approved (or in active development) antineoplastic agents by classification is as follows.

Structure-Based Classes: Fluoropyrimidines—5-FU, Fluorodeoxyuridine, Ftorafur, 5'-deoxyfluorouridine, UFT, S-1 Capecitabine; pyrimidine Nucleosides—Deoxycytidine, Cytosine Arabinoside, 5-Azacytosine, Gemcitabine, 5-Azacytosine-Arabinoside; Purines—6-Mercaptopurine, Thioguanine, Azathioprine, Allopurinol, Cladribine, Fludarabine, Pentostatin, 2-Chloro Adenosine; Platinum Analogues—Cisplatin, Carboplatin, Oxaliplatin, Tetraplatin, Platinum-DACH, Ormaplatin, CI-973, JM-216; Anthracyclines/Anthracenediones—Doxorubicin, Daunorubicin, Epirubicin, Idarubicin, Mitoxantrone; Epipodophyllotoxins—Etoposide, Teniposide; Camptothecins—Irinotecan, Topotecan, Lurtotecan, Silatecan, 9-Amino Camptothecin, 10,11-Methylenedioxy Camptothecin, 9-Nitro Camptothecin, TAS 103, 7-(4-methyl-piperazino-methylene)-10,11-ethylenedioxy-20(S)-camptothecin, 7-(2-N-isopropylamino)ethyl)-20(S)-camptothecin; Hormones and Hormonal Analogues—Diethylstilbestrol, Tamoxifen, Toremefine, Tolmudex, Thymitaq, Flutamide, Bicalutamide, Finasteride, Estradiol, Trioxifene, Droloxifene, Medroxyprogesterone Acetate, Megesterol Acetate, Aminoglutethimide, Testolactone and others; Enzymes, Proteins and Antibodies—Asparaginase, Interleukins, Interferons, Leuprolide, Pegaspargase, and others; Vinca Alkaloids—Vincristine, Vinblastine, Vinorelbine, Vindesine; Taxanes—Paclitaxel, Docetaxel.

Mechanism-Based Classes: Antihormonals—See classification for Hormones and Hormonal Analogues, Anastrozole; Antifolates—Methotrexate, Aminopterin, Trimetrexate, Trimethoprim, Pyritrexim, Pyrimethamine, Edatrexate, MDAM; Antimicrotubule Agents—Taxanes and Vinca Alkaloids; Alkylating Agents (Classical and Non-Classical)—Nitrogen Mustards (Mechlorethamine, Chlorambucil, Melphalan, Uracil Mustard), Oxazaphosphorines (Ifosfamide, Cyclophosphamide, Perfosfamide, Trophosphamide), Alkylsulfonates (Busulfan), Nitrosoureas (Carmustine, Lomustine, Streptozocin), Thiotepa, Dacarbazine and others; Antimetabolites—Purines, pyrimidines and nucleosides, listed above; Antibiotics—Anthracyclines/Anthracenediones, Bleomycin, Dactinomycin, Mitomycin, Plicamycin, Pentostatin, Streptozocin; topoisomerase Inhibitors—Camptothecins (Topo I), Epipodophyllotoxins, m-AMSA, Ellipticines (Topo II); Antivirals—AZT, Zalcitabine, Gemcitabine, Didanosine, and others; Miscellaneous Cytotoxic Agents—Hydroxyurea, Mitotane, Fusion Toxins, PZA, Bryostatin, Retinoids, Butyric Acid and derivatives, Pentosan, Fumagillin, and others.

In addition to the above, an anticancer entity include without any limitation, any topoisomerase inhibitor, vinca alkaloid, e.g., vincristine, vinblastine, vinorelbine, vinflunine, and vinpocetine, microtubule depolymerizing or destabilizing agent, microtubule stabilizing agent, e.g., taxane, aminoalkyl or aminoacyl analog of paclitaxel or docetaxel, e.g., 2'-[3-(N,N-Diethylamino)propionyl]paclitaxel, 7-(N, N-Dimethylglycyl)paclitaxel, and 7-L-alanylpaclitaxel, alkylating agent, receptor-binding agent, tyrosine kinase inhibitor, phosphatase inhibitor, cycline dependent kinase inhibitor, enzyme inhibitor, aurora kinase inhibitor, nucleotide, polynucleotide, and farnesyltransferase inhibitor.

In another embodiment, the entity contained in the liposome composition of the present invention is a therapeutic agent of anthracycline compounds or derivatives, camptothecine compounds or derivatives, ellipticine compounds or derivatives, vinca alkaloinds or derivatives, wortmannin, its analogs and derivatives, or pyrazolopyrimidine compounds with the aurora kinase inhibiting properties.

In yet another embodiment, the entity contained in the liposome composition of the present invention is an anthracycline drug, doxorubicin, daunorubicin, mitomycin C, epirubicin, pirarubicin, rubidomycin, carcinomycin, N-acetyl adriamycin, rubidazone, 5-imidodaunomycin, N-acetyldaunomycine, daunoryline, mitoxantrone; a camptothecin compound, camptothecin, 9-aminocamptothecin, 7-ethylcamptothecin, 10-hydroxycamptothecin, 9-nitro-camptothecin, 10,11-methylenedioxycamptothecin, 9-amino-10,11-methyl enedioxycamptothecin, 9-chloro-10, 11-methylenedioxycamptothecin, irinotecan, topotecan, lurtotecan, silatecan, (7-(4-methylpiperazinomethylene)-10,11-ethylenedioxy-20(S)-camptothecin, 7-(4-methylpiperazinomethylene)-10,11-methylenedioxy-20(S)-camptothecin, 7-(2-N-isopropylamino)ethyl)-(20S)-camptothecin; an ellipticine compound, ellipticine, 6-3-aminopropyl-ellipticine, 2-diethylaminoethyl-ellipticinium and salts thereof, datelliptium, retelliptine.

In yet another embodiment, the entity contained in the liposome of the present invention is a pharmaceutical entity including, without limitation any of the following: antihistamine ethylenediamine derivatives (bromphenifamine, diphenhydramine); Anti-protozoal: quinolones (iodoquinol); amidines (pentamidine); antihelmintics (pyrantel); anti-schistosomal drugs (oxaminiquine); antifungal triazole derivatives (fliconazole, itraconazole, ketoconazole, miconazole); antimicrobial cephalosporins (cefazolin, cefonicid, cefotaxime, ceftazimide, cefuoxime); antimicrobial beta-lactam derivatives (aztreopam, cefmetazole, cefoxitin); antimicrobials of erythromycine group (erythromycin, azithromycin, clarithromycin, oleandomycin); penicillins (benzylpenicillin, phenoxymethylpenicillin, cloxacillin, methicillin, nafcillin, oxacillin, carbenicillin); tetracyclines; other antimicrobial antibiotics, novobiocin, spectinomycin, vancomycin; antimycobacterial drugs: aminosalicycic acid, capreomycin, ethambutol, isoniazid, pyrazinamide, rifabutin, rifampin, clofazime; antiviral adamantanes: amantadine, rimantadine; quinidine derivatives: chloroquine, hydroxychloroquine, promaquine, qionone; antimicrobial qionolones: ciprofloxacin, enoxacin, lomefloxacin, nalidixic acid, norfloxacin, ofloxacin; sulfonamides; urinary tract antimicrobials: methenamine, nitrofurantoin, trimetoprim; nitroimidazoles: metronidazole; cholinergic quaternary ammonium compounds (ambethinium, neostigmine, physostigmine); anti-Alzheimer aminoacridines (tacrine); anti-Parkinsonal drugs (benztropine, biperiden, procyclidine, trihexylhenidyl); anti-muscarinic agents (atropine, hyoscyamine, scopolamine, propantheline); adrenergic dopamines (albuterol, dobutamine, ephedrine, epinephrine, norepinephrine, isoproterenol, metaproperenol, salmetrol, terbutaline); ergotamine derivatives; myorelaxants or curane series; central action myorelaxants; baclophen, cyclobenzepine, dentrolene; nicotine; beta-adrenoblockers (acebutil, amiodarone); benzodiazepines (ditiazem); antiarrhythmic drugs (diisopyramide, encaidine, local anesthetic series—procaine, procainamide, lidocaine, flecaimide), quinidine; ACE inhibitors: captopril, enelaprilat, fosinoprol, quinapril, ramipril; antilipidemics: fluvastatin, gemfibrosil, HMG-coA inhibitors (pravastatin); hypotensive drugs: clonidine, guanabenz, prazocin, guanethidine, granadril, hydralazine; and non-coronary vasodilators: dipyridamole.

According to the present invention, the entity contained in the liposome composition of the present invention can also be a pre-entity, e.g., a pro-drug or an agent that is capable of being converted to a desired entity upon one or more conversion steps under a condition such as a change in pH or an enzymatic cleavage of a labile bond. Such conversion may occur after the release of the pro-drug from the liposome interior at the intended site of the drug/liposome action. However, the pre-entity can be converted into the desired active entity inside the liposomes of the present invention prior to the use of the liposomes as a delivery vehicle, e.g., administration to a patient. For example, an entity can be modified into a pre-entity so that it is easier to be loaded into the liposomes and then it can be converted back into the desired entity once it is inside the liposomes of the present invention. In this manner, according to the present invention, the entities that are generally not amenable to "active", "remote" or other gradient-based loading methods, can be effectively loaded into liposomes, e.g., into the liposome interior space, in their native, unmodified form.

Globally cationic compounds, that is, compounds capable of attaining a net positive ionic charge under the liposome loading conditions, especially the compounds containing a titratable amine, are known to effectively load into liposomes exhibiting transmembrane ion gradients. If an entity of interest is an organic compound and is not a globally cationic compound having a titratable amine, a derivative thereof having the requisite ionic properties can be prepared by a suitable modification, e.g., according to the methods described in Woodle et al., in WO 96/25147. For example, an amine group can be introduced by esterification of a hydroxyl group of the entity with an amino acid. Alternatively, a hydrophobic group can be introduced into a water-soluble compound to aid in its partition into the liposome membrane and subsequent traversing of the membrane to the intraliposomal compartment, i.e., inside the liposomes. Another useful modification to create a liposome-loadable pre-entity is the formation of a carbonyl group adduct, e.g., a hydrazone, an oxime, an acetal, or a ketal. A modified amino-containing group can be hydrolyzed or otherwise chemically split from the modified compound after the loading of the modified compound into the liposomes according to the present invention. Typical processes to intraliposomally regenerate the entity from a pre-entity are hydrolysis, photolysis, radiolysis, thiolysis, ammonolysis, reduction, substitution, oxidation, or elimination. These processes can be effected, without limitation, by the change of pH or by an enzymatic action. For example, paclitaxel or docetaxel, a non-ionic entities, are converted into their 2'-(diethylaminopropionyl)- or 7'-(diethylaminopropionyl) esters, which are weak bases (pre-entities). After loading into the liposomes by any known method, including, without limitation, "active", "remote", "transmembrane-gradient-based" or "solubility gradient based" methods, and/or the methods of the present invention, the intraliposomal 2'-(diethylaminopropionyl)-paclitaxel is converted into original paclitaxel by stimulating its hydrolysis through the increase of pH to above pH 7.0. Thus, a liposome encapsulating a neutral taxane molecule within its interior space is obtained with the drug/lipid ratio of over 0.05 mole per mole of the liposome lipid, without the help of hydrophilic covalent modifications of the taxane molecule (e.g. by attachment of PEG), cyclodextrine taxane compexes, or taxane-solubilizing, micelle-forming surfactants.

According to the present invention, the liposomes contained in the liposome composition of the present invention can be any liposome known or later discovered in the art. In general, the liposomes of the present invention can have any liposome structure, e.g., structures having an inner space sequestered from the outer medium by one or more lipid bilayers, or any microcapsule that has a semi-permeable membrane with a lipophilic central part where the membrane sequesters an interior. A lipid bilayer can be any arrangement of amphiphilic molecules characterized by a hydrophilic part (hydrophilic moiety) and a hydrophobic part (hydrophobic moiety). Usually amphiphilic molecules in a bilayer are arranged into two dimensional sheets in which hydrophobic moieties are oriented inward the sheet while hydrophilic moieties are oriented outward. Amphiphilic molecules forming the liposomes of the present invention can be any known or later discovered amphiphilic molecules, e.g., lipids of synthetic or natural origin or biocompatible lipids. Liposomes of the present invention can also be formed by amphiphilic polymers and surfactants, e.g., polymerosomes and niosomes. For the purpose of this disclosure, without limitation, these liposome-forming materials also are referred to as "lipids".

According to the present invention, the liposomes contained in the liposome composition of the present invention can also be targeting liposomes, e.g., liposomes containing one or more targeting moieties or biodistribution modifiers on the surface of the liposomes. A targeting moiety can be any agent that is capable of specifically binding or interacting with a desired target. In one embodiment, a targeting moiety is a ligand. The ligand, according to the present invention, preferentially binds to and/or internalizes into, a cell in which the liposome-entrapped entity exerts its desired effect (a target cell). A ligand is usually a member of a binding pair where the second member is present on or in a target cells or in a tissue comprising the target cell. Examples of ligands suitable for the present invention are: the folic acid, protein, e.g., transferrin, growth factor, enzyme, peptide, receptor, antibody or antibody fragment, such as Fab', Fv, single chain Fv, single-domain antibody, or any other polypeptide comprising antigen-binding sequences (CDRs) of an antibody molecule. A ligand-targeted liposome wherein a targeting moiety is an antibody or a target antigen-binding fragment thereof is called an immunoliposome. In a preferred embodiment, the liposome carrying a targeting moiety, e.g., a ligand, is internalized by a target cell. In yet another embodiment, a targeting moiety is a ligand that specifically interacts with a tyrosine kinase receptor such as, for example, EGFR, HER2, HER3, HER4, PD-GFR, VEGFR, bFGFR or IGFR receptors. In still another embodiment, the targeting moiety specifically interacts with a growth factor receptor, an angiogenic factor receptor, a transferrin receptor, a cell adhesion molecule, or a vitamin receptor.

According to another embodiment of the present invention, the liposomes contained in the liposome composition exhibit a transmembrane concentration gradient of a substituted ammonium and/or polyanion of the present invention. Preferably, the higher concentration is in the interior (inner) space of the liposomes. In addition, the liposome composition of the present invention can include one or more trans-membrane gradients in addition to the gradient created by the substituted ammonium and/or polyanion of the present invention. For example, the liposomes contained in the liposome composition of the present invention can additionally include a transmembrane pH gradient, ion gradient, electrochemical potential gradient, and/or solubility gradient.

According to yet another embodiment of the present invention, the liposome composition of the present invention can be provided in a kit comprising a container with the liposomes, and optionally, a container with the entity and an instruction, e.g., procedures or information related to using the liposome composition in one or more applications. Such instruction can be provided via any medium, e.g., hard paper copy, electronic medium, or access to a database or website containing the instruction.

The liposome membrane composition of the present invention can be made by any suitable method known to or later discovered by one skilled in the art. In general, a variety of lipid components can be used to make the liposomes of the present invention. Lipid components usually include, but are not limited to (1) uncharged lipid components, e.g., cholesterol, ceramide, diacylglycerol, acyl(poly ethers) or alkylpoly(ethers); (2) neutral phospholipids, e.g., diacylphosphatidylcholines, sphingomyelins, and diacylphosphatidylethanolamines, (3) anionic lipids, e.g., diacylphosphatidylserine, diacylphosphatidylglycerol, diacylphosphatidate, cardiolipin, diacylphosphatidylinositol, diacylglycerolhemisuccinate, diaclyglycerolhemigluratate, cholesterylhemisuccinate, cholesterylhemiglutarate, and the like; (4) polymer-conjugated lipids, e.g., N-[methoxy-(poly(ethylene glycol)diacylphosphatidylethanolamine, poly(ethylene glycol)-diacylglycerol, poly(ethylene glycol)-ceramide; and (5) cationic lipids, e.g., 1,2,-diacyl-3-trimethylammonium-propane (DOTAP), dimethyl dioctadecylammonium bromide (DDAB), and 1,2-diacyl-sn-glycero-3-ethylphosphocholine. Monoacyl-substituted derivatives of these lipids, as well as di- and monoalkyl-analogs can be also employed.

Various lipid components can be selected to fulfill, modify or impart one or more desired functions. For example, phospholipid can be used as principal vesicle-forming lipid. Inclusion of cholesterol is useful for maintaining membrane rigidity and decreasing drug leakage. Polymer-conjugated lipids can be used in the liposomal formulation to increase the lifetime of circulation via reducing liposome clearance by liver and spleen, or to improve the stability of liposomes against aggregation during storage, in the absence of circulation extending effect. While inclusion of PEG-lipids in the amount 1 mol % or above of the liposome lipid is asserted to have a several-fold prolongation of the liposome blood circulation time (see, e.g., U.S. Pat. No. 5,013,556), we have surprisingly discovered that liposomes of the present invention are quite long-circulating, and the addition of PEG-lipid to the liposome composition only extended the circulation longevity for less than two-fold, if at all. In addition, charge-modulating (titratable) lipids can be used to help delivery of liposome encapsulated entities to cytosolic or nuclear targets via facilitating some classes of entities escaping the confines of endosomal pathway.

In one embodiment, the liposomes of the present invention include lecithin, cholesterol, and an amphipathic polymer. The lecithin included in the liposomes of the present invention can be a natural lecithin, a hydrogenated natural lecithin, a synthetic lecithin, 1,2-distearoyl-lecithin, dipalmitoyl lecithin, dimyristoyl lecithin, dioleolyl lecithin, 1-stearoyl-2-oleoyl lecithin, or 1-palmitoyl-2-oleoyl lecithin whereas the amphipathic polymer can be a polyethylene glycol-lipid derivative, e.g., polyethylene glycol phosphatidylethanolamine, polyethylene glycol-diacylglycerol, or polyethyleneglycol-ceramide derivative, where the poly (ethylene glycol) portion has molecular weight from about 250 to about 20,000, most commonly from about 500 to about 5,000. In another embodiment, the lecithin and cholesterol ratio in the liposomes of the present invention is about 3:2 by mole. In yet another embodiment, the amphipathic polymer is at least 0.1 mole % of the liposome-forming lipid in the liposomes of the present invention. In yet another embodiment, the amount of an amphipathic polymer is between 0.1 mole % and 1 mole % of the liposome-forming lipid in the liposomes of the present invention. Preferably, the amphipathic polymer is a neutral polymer, i.e. possesses under the drug loading conditions the net ionic charge of zero, for example, PEG-diacylglycerol, PEG-dialkylglycerol, or PEG-ceramide. It was unexpectedly discovered that inclusion of ionically neutral amphipathic lipids up to PEG-lipid content of about 5.7 mol. % of total lipid afford high efficiency liposome loading of, e.g., vinca alkaloids, such as vinorelbine, while in the case of anionically charged PEG-DSPE the loading efficiency noticeably declined at the PEG-lipid content of 1.6 mol. % or more (Example 72).

In still another embodiment, the liposomes of the present invention contain a camptothecin derivative, e.g., a camptothecin prodrug such as irinotecan and is comprised of lecithin and cholesterol, e.g., at a ratio of about 3:2 by mole, and an amphipathic polymer, e.g., at an amount of at least 0.1 mole % or less than 1% of the liposome-forming lipid.

Liposomes of the present invention can be made by any method that is known or will become known in the art. See, for example, G. Gregoriadis (editor), *Liposome Technology*, vol. 1-3, 1st edition, 1983; 2nd edition, 1993, CRC Press, Boca Raton, Fla. Examples of methods suitable for making liposome composition of the present invention include extrusion, reverse phase evaporation, sonication, solvent (e.g., ethanol) injection, microfluidization, detergent dialysis, ether injection, and dehydration/rehydration. The size of liposomes can be controlled by controlling the pore size of membranes used for low pressure extrusions or the pressure and number of passes utilized in microfluidisation or any other suitable methods. In one embodiment, the desired lipids are first hydrated by thin-film hydration or by ethanol injection and subsequently sized by extrusion through membranes of a defined pore size; most commonly 0.05 μm, 0.08 μm, or 0.1 μm.

Liposome compositions containing the substituted ammonium and/or polyanion of the present invention inside the liposomes can be made by any suitable methods, e.g., formation of liposomes in the presence of the substituted ammonium and/or polyanion of the present invention, e.g., in the form of salt. The substituted ammonium and/or polyanion outside of the liposomes can be removed or diluted either following liposome formation or before loading or entrapping a desired entity. Alternatively, liposome composition containing the substituted ammonium and/or polyanion of the present invention can be made via ion exchange method directly or via an intermediate free acid step having a gradient of substituted ammonium of the present invention, e.g., substituted ammonium salt of polyanionized sugar or polyol. Such liposomes can be neutralized using the amine or its salt with a volatile acid, e.g., carbonate. The resulting liposome solution can be used directly or alternatively the salt contained therein can be removed if desired, e.g., by evaporation and crystallization followed by dissolution in an aqueous medium.

Preferably, the liposome composition of the present invention has a transmembrane concentration gradient of the substituted ammonium and/or polyanion, e.g., the concentration of the substituted ammonium and/or polyanion salt inside the liposome is higher, usually at least 100 times higher, than the concentration of the substituted ammonium and/or polyanion in the medium outside the liposome.

In one embodiment, the concentration of the substituted ammonium and/or polyanion salt inside the liposome is at least 100 times higher than the concentration of the substituted ammonium and/or polyanion salt in the medium outside the liposome and is at least at a concentration of about 10 mM, 50 mM, 0.1M, 0.2M, 0.5M, 0.6M, 0.7M, or 1.0M, wherein molarity is calculated based on the substituted ammonium. In another embodiment, the concentration of the substituted ammonium and/or polyanion salt inside the liposome is at least 100 times higher than the concentration of the substituted ammonium and/or polyanion salt in the medium outside the liposome and is at a concentration of about 0.65M or about 1.0M.

In addition, the liposome composition of the present invention usually has a pH outside which is compatible with or helpful for maintaining the stability of a desired entity during the loading process, along with the high loading efficiency, e.g., above 90% entrapment. For example, pH in the range of 4-7, or pH 4.5-6.5, is preferred. In particular, according to the present invention, loading of a camptothecin compound, e.g., topotecan or irinotecan, is best accomplished at the pH of the outer medium in the range between about 4.0 and about 7.0, more preferably between about pH 5.0 and pH 6.5. Loading of a vinca derivative, e.g., vincristine, vinorelbine, or vinblastine is best accomplished at pH about 5.0-7.0, more preferably at pH about 6.5.

According to the present invention, a desired entity can be loaded or entrapped into the liposomes by incubating the desired entity with the liposomes of the present invention in an aqueous medium at a suitable temperature, e.g., a temperature above the component lipids' phase transition temperature during loading while being reduced below the phase transition temperature after loading the entity. The incubation time is usually based on the nature of the component lipids, the entity to be loaded into the liposomes, and the incubation temperature. Typically, the incubation times of few minutes to several hours are sufficient. Because high entrapment efficiencies of more than 85%, typically more than 90%, are achieved, there is usually no need to remove unentrapped entity. If there is such a need, however, the unentrapped entity can be removed from the composition by various mean, such as, for example, size exclusion chromatography, dialysis, ultrafiltration, adsorption, or precipitation. It was unexpectedly found that maintaining of the low ionic strength during the incubation of an entity, such as, in particular, a camptothecin derivative or a vinca alkaloid derivative, with the liposomes of the present invention, followed by the increase in ionic strength at the end of the incubation, results in higher loading efficiency, better removal of unentrapped drug, and better liposome stability against aggregation. Typically, the incubation is conducted, e.g., in an aqueous solution, at the ionic strength of less than that equivalent to 50 mM NaCl, or more preferably, less than that equivalent to 30 mM NaCl. Following the incubation, a concentrated salt, e.g., NaCl, solution may be added to raise the ionic strength to higher than that of 50 mM NaCl, or more preferably, higher than that of 100 mM NaCl. Without being bound by a theory, we hypothesize that the increase of ionic strength aids dissociation of the entity from the liposome membrane, leaving substantially all entity encapsulated within the liposomal interior space.

In general, the entity-to-lipid ratio, e.g., drug load ratio obtained upon loading an entity depends on the amount of the entity entrapped inside the liposomes, the concentration of entrapped substituted ammonium and/or polyanion, e.g., salt, the physicochemical properties of the entrapped entity and the type of counter-ion (anion), e.g., polyanion used. Because of high loading efficiencies achieved in the compositions and/or by the methods of the present invention, the entity-to-lipid ratio for the entity entrapped in the liposomes is over 80%, over 90%, and typically more than 95% of the entity-to-lipid ratio calculated on the basis of the amount of the entity and the liposome lipid taken into the loading process (the "input" ratio). Indeed, practically 100% (quantitative) encapsulation is common. The entity-to lipid ratio in the liposomes can be characterized in terms of weight ratio (weight amount of the entity per weight or molar unit of the liposome lipid) or molar ratio (moles of the entity per weight or molar unit of the liposome lipid). One unit of the entity-to-lipid ratio can be converted to other units by a routine calculation, as exemplified below. The weight ratio of an entity in the liposomes of the present invention is typically at least 0.05, 0.1, 0.2, 0.35, 0.5, or at least 0.65 mg of the entity per mg of lipid. In terms of molar ratio, the entity-to-lipid ratio according to the present invention is at least from about 0.02, to about 5, preferably at least 0.1 to about 2, and more preferably, from about 0.15 to about 1.5 moles of the drug per mole of the liposome lipid. In one embodiment, the entity-to-lipid ratio, e.g., drug load ratio of camptothecin derivatives is at least 0.1, e.g., 0.1 mole of camptothecin derivative per one mole of liposome lipid, and preferably at least 0.2. In another embodiment, the entity-to-lipid ratio, e.g., drug load is at least about 300 mg entity (e.g., vinca alkaloid or a derivative thereof) per mg of liposome-forming lipid. In yet another embodiment, the entity-to-lipid ratio, e.g., drug load is at least about 500 mg entity (e.g. camptothecin derivative or camprothecin prodrug) per mg of liposome-forming lipid. Surprisingly, the invention afforded stable and close to quantitative liposomal encapsulation of a camptothecin derivative drug, e.g., irinotecan, at the drug-to-lipid ratio of over 0.8 mmol of the entity per 1 g of liposome lipid, over 1.3 mmol of entity per 1 g of liposome lipid, and even at high as 1.7 mmol entity per 1 g liposome lipid (see Example 74).

If the liposome comprises a phospholipid, it is convenient to express the entity content in the units of weight (mass) amount of the drug per molar unit of the liposome phospholipid, e.g., mg drug/mmol of phospholipid. However, a person skilled in the art would appreciate that the drug content can be equivalently expressed in a manner independent of the presence of phospholipids in a liposome, and furthermore, can be equivalently expressed in terms of a molar amount of the drug per unit (mass or molar) of the liposome lipid content. For example, a liposome containing 3 molar parts of distearoylphosphatidylcholine (DSPC, molecular weight 790), 2 molar parts of cholesterol (molecular weight 387), and 0.015 molar parts of poly(ethylene glycol)-derivatized di stearoylphosphatidylethanolamine (PEG-DSPE, molecular weight 2750), and containing a drug doxorubicin (molecular weight 543.5) at the drug/lipid ratio of 150 mg/mmol phospholipid, the same drug content can be equivalently expressed in terms of mg drug/mg total lipid as follows:

(a) Calculate the molar amounts of liposome lipid components normalized to the molar unit of liposome phospholipids (DSPC and PEG-DSPE in this example) by dividing the molar quantity of a component by the total of the molar quantities of the liposome phospholipids:
DSPC 3/(3+0.015)=0.99502
Cholesterol 2/(3+0.015)=0.66335
PG-DSPE 0.015/(3+0.015)=0.00498

(b) Calculate the mass amount of total liposome lipid corresponding to a unit molar amount of liposome phospholipid and the components molecular weights:
Total lipid, mg/mmol phospholipid=0.99502×790+0.66335×387+0.00498×2750=1056.48

(c) Calculate the mass amount of drug per mass unit of total lipid by dividing the drug content expressed in mass units per molar unit of phospholipid by the number obtained in step (b):
Doxorubicin, mg/mg total lipid=150/1056.48=0.14198.

(d) Calculate the molar amount of the drug per unit mass of total lipid by dividing the number obtained in step (c) by the drug molecular weight (in this case, 543.5):
Doxorubicin, mmol/g total lipid=0.14198/543.5×1000=0.261.

(e) Calculate the molar part of phospholipids in the liposome lipid matrix:
Phospholipid molar part=(total moles of phospholipids)/(total moles amount of lipids)=(3+0.015)/(3+2+0.015)= 0.6012.

(f) Calculate the molar ratio of doxorubicin to total lipid.
Doxorubicin, mol/mol of total lipid=(Phospholipid molar part)×(Doxorubicin, g/mole phospholipid)/(Doxorubicin molecular weight)=0.6012×150/543.5=0.166

Thus, the relationship between drug-to-lipid and drug-to-phospholipid ratio expressed in various units is readily established. As used herein, a "lipid" includes, without limitation, any membrane-forming components of the liposome membrane, such as, for example, polymers and/or detergents.

The liposome entrapped substituted ammonium and/or polyanion salt solution of the present invention usually has an osmotic strength (osmolality) which helps to keep the liposomes stable against osmotic damage (swelling and/or burst) without sacrificing the loading capacity of the liposomes. In one embodiment, the osmolality of the liposome composition of the present invention is in the range of 0.1 to 1.5 mol/kg or, preferably, 0.2 to 1.0 mol/kg. Surprisingly, we found that liposomes of the present invention are stable against adverse effect of high intraliposomal osmotic strength on the drug loading. Intraliposomal osmolarities of as high as 0.727 mol/kg were well tolerated, resulting in practically quantitative loading of a drug up to the theoretical maximum of stoichiometric exchange of intraliposomal substituted ammonium ions for molecules of the drug (in the case of irinotecan, one drug molecule per one substituted ammonium ion), even though the osmolarity of the extraliposomal aqueous medium during the co-incubation of the drug and the liposomes was close to the physiological value of about 0.3 mol/kg (Example 74).

In general, the liposome composition of the present invention is quite stable during storage, e.g., as measured by the percentage of entrapped entity released outside of the liposomes or still maintained inside of the liposomes after a certain time period from the initial loading of the entity inside the liposomes of the present invention. For example, the liposome composition of the present invention is stable at 4° C. for at least 6 months, e.g., less than 10% of entrapped entity is released 6 months after the initial loading of the entity. In one embodiment, the liposome composition of the present invention is stable at 4° C. for at least 2 years, e.g., less than 20% of entrapped entity is released 2 years after the initial loading of the entity.

It is advantageous for a liposome-entrapped entity to remain encapsulated in the liposome until the liposome reaches the site of its intended action, e.g., in the case of a liposomal antitumor drug administered in a patient, a tumor. The liposomes of the present invention showed surprising stability against the release (leakage) of the entrapped entity under in vivo conditions, e.g. in the blood of a mammal. The exposure time needed for 50% release of the entrapped entity, e.g. drug, from the liposomes (half-release time) in the blood of a rat in vivo was more than 24 hours. In particular, liposomes loaded with vinca alkaloid drugs, e.g., vinblastine, vincristine, and vinorelbine, showed remarkable stability against drug leakage in vivo, with half-release time of at least 24 hours, or the amount of entity remaining encapsulated after 24 hours in the blood in vivo at least about 50% of the pre-administration value. Typically the half-release time over 33 hours, or the amount of encapsulated entity remaining encapsulated after 24 hours in the blood in vivo at least about 60%, was observed; and even the half-release time over 46 hours, or the amount of encapsulated entity after 24 hours in the blood in vivo at least about 70% of the pre-administration value, was common. Sometimes the half-release time for an encapsulated drug in the blood in vivo was over 93 hours, and even over 120 hours.

The liposome loaded with camptothecin derivatives, such as topotecan and irinotecan, also showed exceptional in vivo stability in the blood, with 79-85% of the original drug load remaining encapsulated after 24 hours. Remarkably, the liposomes of the present invention, while having such low in vivo drug release rate in the blood circulation, showed substantial in vivo antitumor activity exceeding that of the free drug (i.e administered as a solution).

The liposomes of the present invention provided unexpected combination of the high efficiency of the entrapped therapeutic agent and low toxicity. In general, the activity of a therapeutic entity liposomally encapsulated according to the present invention, e.g., the anti-neoplastic activity of a camptothecin derivative in a mammal, is at least equal to, at least two times higher, or at least four times higher than the activity of the therapeutic entity if it is administered in the same amount via its routine non-liposome formulation, e.g., without using the liposome composition of the present invention, while the toxicity of the liposomally encapsulated entity does not exceed, is at least twice, at least three times, or at least four times lower than that of the same therapeutic entity administered in the same dose and schedule but in a free, non-encapsulated form. For example, it is generally known that liposomal encapsulation of anti-cancer camptothecin derivatives by the published methods of others results in the increased toxicity (lower maximum tolerated dose, lower 50% lethality dose) compared to unencapsulated drug. See U.S. Pat. No. 6,355,268; U.S. Pat. No. 6,465,008; Colbern, et al. *Clinical Cancer Res*. 1998, v. 4, p. 3077-3082; Tardi, et al. *Cancer Res*., 2000, v. 60, p. 3389-3393; Emerson, et al. *Clinical Cancer Res*. 2000, v. 6, p. 2903-2912. Liposomally encapsulated camptothecin pro-drugs, such as irinotecan (CPT-11), which is a water-soluble, cationic camptothecin pro-drug derivative, have substantially higher, e.g. at least 4 times, and even 10 times, higher antitumor activity assessed in an in vivo tumor model than the drug in the absence of a liposomal formulation, e.g., in a free (solution) form. This is even more remarkable since a therapeutic compound, e.g., a camptothecin pro-drug, requires enzymatic activation, e.g., by the action of endogenous non-specific carboxylesterase, but according to the present invention is encapsulated substantially within the interior space of the liposome. On the other hand, surprisingly, the toxicity of camptothecin prodrug such as CPT-11 in the liposomal form (drug/lipid mass ratio over 0.1, e.g., 0.2-0.6 or more) according to the present invention was over 2 times, over 3 times, and even over 4 times lower that than of the free (unencapsulated) pro-drug CPT-11. Moreover, a prolonged drug release from the CPT-11 liposomes in vivo was achieved, with more than 50%, and even more than 70% (79-86%) of the original drug content still remaining in the liposomes 24 hours after administration into the bloodstream, and with half-release times in excess of 24 hours, typically in excess of 48 hours. The prolonged remanence of the drug in the liposome in vivo was associated with higher antitumor effect. Surprisingly, the slowest in vivo CPT-11 release and the highest antitumor activity was observed in the liposomes containing low-molecular polyanionized sugar derivative (sucrose octasulfate) rather than a polymeric anion (polyphosphate) (Example 15).

According to another embodiment of the present invention, the liposome composition of the present invention can be provided as a pharmaceutical composition containing the liposome composition of the present invention and a carrier, e.g., pharmaceutically acceptable carrier. Examples of pharmaceutically acceptable carries are normal saline, isotonic dextrose, isotonic sucrose, Ringer's solution, and Hanks' solution. A buffer substance can be added to provide pH optimal for storage stability. For example, pH between about 6.0 and about 7.5, more preferably pH about 6.5, is optimal for the stability of liposome membrane lipids, and provides for excellent retention of the entrapped entities. Histidine, hydroxyethylpiperazine-ethylsulfonate (HEPES), morpholipo-ethylsulfonate (MES), succinate, tartrate, and citrate, typically at 2-20 mM concentration, are exemplary buffer substances. Other suitable carriers include, e.g., water, buffered aqueous solution, 0.4% NaCl, 0.3% glycine, and the like. Protein, carbohydrate, or polymeric stabilizers and tonicity adjusters can be added, e.g., gelatin, albumin, dextran, or polyvinylpyrrolidone. The tonicity of the composition can be adjusted to the physiological level of 0.25-0.35 mol/kg with glucose or a more inert compound such as lactose, sucrose, mannitol, or dextrin. These compositions may be sterilized by conventional, well known sterilization techniques, e.g., by filtration. The resulting aqueous solutions may be packaged for use or filtered under aseptic conditions and lyophilized, the lyophilized preparation being combined with a sterile aqueous medium prior to administration.

The pharmaceutical liposome compositions can also contain other pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. Additionally, the liposome suspension may include lipid-protective agents which protect lipids against free-radical and lipid-peroxidative damages on storage. Lipophilic free-radical quenchers, such as alpha-tocopherol and water-soluble iron-specific chelators, such as ferrioxamine, are suitable.

The concentration of the liposomes of the present invention in the fluid pharmaceutical formulations can vary widely, i.e., from less than about 0.05% usually or at least about 2-10% to as much as 30 to 50% by weight and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, liposome pharmaceutical compositions composed of irritating lipids may be diluted to low concentrations to lessen inflammation at the site of administration.

The amount of liposome pharmaceutical composition administered will depend upon the particular therapeutic entity entrapped inside the liposomes, the disease state being treated, the type of liposomes being used, and the judgment of the clinician. Generally the amount of liposome pharmaceutical composition administered will be sufficient to deliver a therapeutically effective dose of the particular therapeutic entity.

The quantity of liposome pharmaceutical composition necessary to deliver a therapeutically effective dose can be determined by routine in vitro and in vivo methods, common in the art of drug testing. See, for example, D. B. Budman, A. H. Calvert, E. K. Rowinsky (editors). *Handbook of Anticancer Drug Development*, L W W, 2003. Therapeutically effective dosages for various therapeutic entities are well known to those of skill in the art; and according to the present invention a therapeutic entity delivered via the pharmaceutical liposome composition of the present invention provides at least the same, or 2-fold, 4-fold, or 10-fold higher activity than the activity obtained by administering the same amount of the therapeutic entity in its routine non-liposome formulation. Typically the dosages for the liposome pharmaceutical composition of the present invention range between about 0.005 and about 500 mg of the therapeutic entity per kilogram of body weight, most often, between about 0.1 and about 100 mg therapeutic entity/kg of body weight.

Typically, the liposome pharmaceutical composition of the present invention is prepared as a topical or an injectable, either as a liquid solution or suspension. However, solid forms suitable for solution in, or suspension in, liquid vehicles prior to injection can also be prepared. The composition can also be formulated into an enteric-coated tablet or gel capsule according to known methods in the art.

The liposome composition of the present invention can be administered in any way which is medically acceptable which may depend on the condition or injury being treated. Possible administration routes include injections, by parenteral routes such as intramuscular, subcutaneous, intravenous, intraarterial, intraperitoneal, intraarticular, intraepidural, intrathecal, or others, as well as oral, nasal, ophthalmic, rectal, vaginal, topical, or pulmonary, e.g., by inhalation. For the delivery of liposomally drugs formulated according to the invention, to tumors of the central nervous system, a slow, sustained intracranial infusion of the liposomes directly into the tumor (a convection-enhanced delivery, or CED) is of particular advantage. See Saito, et al., Cancer Research, vol. 64, p. 2572-2579, 2004; Mamot, et al., J. Neuro-Oncology, vol. 68, p. 1-9, 2004. The compositions may also be directly applied to tissue surfaces. Sustained release, pH dependent release, or other specific chemical or environmental condition mediated release administration is also specifically included in the invention, e.g., by such means as depot injections, or erodible implants.

EXAMPLES

The following examples are intended to illustrate but not to limit the invention in any manner, shape, or form, either explicitly or implicitly. While they are typical of those that might be used, other procedures, methodologies, or techniques known to those skilled in the art may alternatively be used.

Example 1

Preparation of the Solutions of Substituted Ammonium Salts

Trialkylammonium and dialkylammonium sulfate solutions useful for loading drugs (e.g., doxorubicin) into liposomes were prepared by diluting sulfuric acid with water to a concentration of 0.25 M and then titrating the sulfuric acid solution with one of a variety of amines. The substituted amines used in this example were triethylamine, trimethylamine, dimethylamine, diethylamine, or diethanolamine. After the addition of the amines, the resulting solution was diluted to a final concentration of 0.2 M of the substituted ammonium salt. Osmolality was determined using a dew point osmometer. The properties of resulting substituted alkylammonium sulfate salt solutions are shown in the Table 1 below.

TABLE 1

Properties of various dialkylammonium and trialkylammonium sulfate solutions

| Salt | Osmolality, mmol/kg | pH |
|---|---|---|
| Dimethylammonium sulfate | 472 | 5.65 |
| Dimethylethanolammonium sulfate | 509 | 5.72 |
| Diethylammonium sulfate | 519 | 5.85 |
| Trimethylammonium sulfate | 497 | 5.81 |
| Triethylammonium sulfate | 559 | 5.33 |

Example 2

Preparation of Liposomes with Entrapped Dialkylammonium and Trialkylammonium Salts, and Loading of a Substance into these Liposomes Di stearoylphosphatidylcholine (DSPC), cholesterol (Chol), and N-(methoxy-poly(ethylene glycol)-oxycarbonyl)-di stearoylphosphatidylethanolamine (PEG-DSPE) (prepared from poly(ethylene glycol) with mol. weight 2,000) were co-dissolved in chloroform in a molar ratio of 3:2:0.015, and the chloroform was removed at 55-60° C. by rotary evaporation. The dried lipid film was then hydrated in a solution of one of each dialkyl- or trialkylammonium sulfates listed in Example 1 at 60° C. for 30 min. The lipid suspension was extruded under pressure through two stacked polycarbonate track-etched membrane filters with the pore size of 0.1 µm (Corning Nuclepore). The liposome size determined by quasielastic light scattering method was approximately 110-120 nm. Unencapsulated trialkylammonium or dialkylammonium salts were removed from the external medium of the liposomes by gel filtration using a cross-linked dextran gel (Sephadex G-75, Amersham Pharmacia Biotechnology) column eluted with HEPES-buffered saline, pH 7.2-7.4, and the liposomes were collected in a void-volume fraction of the column. Doxorubicin hydrochloride USP (lyophilized powder containing 5 weight parts of lactose per 1 part of doxorubicin) was added to the liposomes at a concentration of 150 µg drug/µmol of liposome phospholipid. The mixture was incubated at 55° C. for 45 min, chilled on ice for 10 min, and unencapsulated drug was removed by gel filtration chromatography using a Sephadex G-75 column eluted with HEPES-buffered saline, pH 7.4. The presence of free doxorubicin (characterized by the appearance of a slower moving red colored band) was visually undetectable. The purified doxorubicin-loaded liposomes were analyzed for phospholipid and doxorubicin according to Examples 70 and 71 (spectrophotometric method), respectively. The resulting drug loading efficiencies are shown in Table 2.

TABLE 2

Loading of doxorubicin in liposomes with entrapped solutions of dialkyl- and trialkylammonium salts. Input drug/phospholipid ratio 150 µg/µmol.

| Liposome-entrapped salt: | Drug/phospholipid ratio in liposomes (µg/µmol) | Entrapment Efficiency (%) |
|---|---|---|
| Trimethylammonium sulfate | 140.74 ± 10.35 | 93.8 ± 5.7 |
| Triethylammonium sulfate | 163.81 ± 16.41 | 109.2 ± 11.6 |
| Diethylammonium sulfate | 158.16 ± 18.34 | 105.4 ± 7.8 |
| Dimethylethanolammonium sulfate | 155.08 ± 8.51 | 103.4 ± 11.6 |

Example 3

Preparation of Liposomes Containing Various Dialkyl-, Trialkyl-, and Heterocyclic-Substituted Ammonium Sulfate Salts and Loading of Doxorubicin into these Liposomes The substituted ammonium sulfate salt solutions were prepared as in Example 1 using commercially available alkyl-substituted, hydroxyalkyl-substituted and heterocyclic amines. Liposomes were formed as in Example 1, except that instead of the lipid film hydration step, the neat lipids were dissolved in ethanol (approximately 100 μl of ethanol for every 50 μmol of phospholipid) and mixed with the substituted ammonium salt solution at 60-65° C. so that the resulting lipid dispersion contained about 10 vol. % of ethanol.

Doxorubicin loading was accomplished by adding doxorubicin solution (2 mg/ml in HEPES-buffered saline pH 6.5) to the liposomes at a ratio of 155 μg drug/μmol liposome phospholipid (PL) and heating at 58° C. for 45 min in a hot water bath. The resulting liposomes were separated from any residual unencapsulated doxorubicin and analyzed for drug and lipid content as in Example 1. The results are shown in Table 3.

TABLE 3

Loading doxorubicin into liposomes with entrapped sterically hindered substituted alkyl, dialkyl-, trialkyl- and heterocyclic ammonium salts solutions.

| Amine used to prepare substituted ammonium salt | Osmolality, mmol/kg | drug load, mg/mmol phospholipid | Loading efficiency, % |
|---|---|---|---|
| Trimethylamine | 497 | 149.4 ± 7.9 | 96.4 ± 4.9 |
| Triethylamine | 559 | 149.6 ± 6.9 | 96.5 ± 4.3 |
| Dimethylethanolamine | 509 | 163.1 ± 6.6 | 105.3 ± 4.5 |
| Dimethylamine | 472 | 158.6 ± 7.4 | 102.3 ± 4.9 |
| Diethylamine | 519 | 156.7 ± 13.0 | 101.1 ± 8.5 |
| Diisopropylamine | 533 | 159.9 ± 6.2 | 103.2 ± 4.1 |
| Tris(hydroxymethyl)-minomethane | 423 | 179.9 ± 15.3 | 116.1 ± 11.5 |
| 1-Piperidineethanol | 506 | 153.5 ± 7.1 | 99.0 ± 4.5 |
| 4-Methylmorpholine | 465 | 152.4 ± 9.8 | 98.3 ± 6.2 |
| Piperidine | 479 | 158.5 ± 12.5 | 102.3 ± 8.2 |
| 1-Methylpyrolidine | 492 | 153.6 ± 12.3 | 99.1 ± 7.8 |
| Dimethylpiperazine | 378 | 158.0 ± 6.5 | 101.9 ± 4.3 |

Example 4

Preparation of Triethylammonium Polyphosphate (TEA-Pn) Solution

Linear sodium poly(phosphate) having 13-18 phosphate units per molecule (Phosphate glass; CALGON®, obtained from Sigma Chemical Company) was dissolved in water to a concentration of about 1.3 M phosphate. The solution was passed through a column packed with 120 mL of sulfonated polystyrene-divinylbenzene copolymer cation exchange resin beads (Dowex 50W×8-200, Dow Chemical Co.) in the hydrogen form. The column was pre-equilibrated with aqueous 3-3.6 M HCl to bring the resin into hydrogen form, and washed with deionized water to neutral pH. Fifteen ml of the sodium polyphosphate solution was applied on the column and eluted with deionized $H_2O$. The column eluent was monitored using a conductivity detector. The column outflow corresponding to the conductivity peak was titrated with neat triethylamine to pH 5.5-6.0. The solution was analyzed for residual sodium by potentiometry using a sodium-sensitive glass electrode and for phosphate content using an inorganic phosphate assay as in Example 1. The solution having residual sodium content of less than 1% was diluted to a final phosphate concentration of 0.55 M. The solution typically has a TEA concentration of 0.52-0.55 M, pH of 5.5-6.0, and osmolality of 430-480 mmol/kg

Example 5

Removal of Unentrapped Polyphosphate Salts from Liposome Preparations

Liposomes (120 nm in size) with entrapped fluorescent marker 8-hydroxypyrene trisulfonate were prepared according to Kirpotin, et al., Biochemistry 36:66-75, 1997, and mixed with the solution of sodium polyphosphate. The mixture was loaded on size exclusion columns containing cross-linked dextran beads (Sephadex G-75), 6% agarose beads (Sepharose 6B-CL), or 4% agarose beads (Sepharose 4B-CL), all from Amersham Pharmacia, and eluted with MES-Dextrose buffer (pH 5.5). The effluents were assayed for phosphate content using the phosphate assay of Bartlett (1959), and for the liposome content by spectrofluorometry. Of the studied gel-chromarography carries, Sepharose CL-6B provided complete separation of the polyphosphate from the liposomes at the sample/column bed volume ratio of 13.

Example 6

Preparing Solution of Triethylammonium Sucroseoctasulfate (TEA-SOS)

Sodium sucrose octasulfate (equivalent weight 144.8) is the sodium salt of sucrose derivative in which all hydroxyl groups have formed sulfuric acid esters. Sucrose octasulfate (SOS) sodium salt was purchased from Toronto Research Chemicals, Toronto, Canada, p/n S699020. Six grams of sodium sucrose octasulfate was dissolved in 16.57 ml of deionized water to give a final concentration of about 2.5 N of the sulfate groups. The solution was treated by ion exchange as in Example 4. The solution of sucroseoctasulfuric acid obtained as an ion exchange column effluent was then titrated with neat triethylamine to pH 5.7 (neutralization point), and the pH and osmolality of the solution were determined. The resulting solution had the calculated triethylammonium concentration of 0.643 M, pH 5.7, and the osmolality of 530 mmol/kg. The presence of residual sodium was undetectable by potentiometry (less than 0.1%).

Example 7

Liposomes Loaded with Irinotecan (CPT-11) Using Substituted Ammonium Salts: Preparation and In Vitro Drug Release in the Presence of Blood Plasma In this example, sulfate, citrate, pyrophosphate, triphosphate, and linear polyphosphate (13-18 mer) were studied as anions in the liposome-entrapped substituted ammonium salt solutions. Phosphate polymers were chosen because of their biodegradability and because polyphosphates are found naturally in the cells, as opposed to other synthetic polymeric anions (polyacrylate, dextran sulfate, and the like). Also, the viscosity of solutions of low molecular weight polyphosphates was lower than that of other polymers, making polyphosphates more process-friendly.

The following materials were used for preparation of salt solutions.

1. Sodium polyphosphate, NaO—[$PO_3Na$]$_n$—Na, n=13-18, purchased from Sigma (Product No. P-8510, "Phosphate Glass, Practical Grade", also known as sodium hexametaphosphate or by the brand name CALGON);

2. Pentasodium tripolyphosphate, $Na_5P_3O_{10}$, purchased from Sigma (Product No. T-5883); 3. Tetrasodium pyrophosphate decahydrate, $Na_4P_2O_7 \cdot 10H_2O$, purchased from Sigma (Product No. P-9146).

4. Ion exchange resins Dowex 50W×4 (4% cross-linked sulfonated polystyrene resin, 100-200 mesh) purchased from Sigma (Product No. 50X4-200) or Dowex HCR-W2 (8% cross-linked sulfonated polystyrene resin 50-100 mesh) purchased from Sigma (Product No. I-8880) were used interchangeably. The resins were washed by decantation in the following order: three times with deionized water, twice with 1N HCl (3× excess over the resin by volume), three times with water, twice with 1N NaOH, three times with water, three times with 1N HCl, and three times with water. After the decantation, the resins were in $H^+$-form.

5. Trimethylamine (TMA), aqueous solution 40%, from Aldrich Chemical Co. (Product No. 43, 326-8). The concentration was established by acid titration to be around 5.9 N.

6. Triethylamine (TEA), 99%, HPLC Grade, from Fisher (Product No. 04884). The concentration by acid titration was 6.9-7.1 N.

Water was purified through reverse osmosis, ion exchange, and organic removal to achieve organic free "16-18 MOhm" quality.

Aqueous solutions of pyrophosphate, triphosphate, and polyphosphate salts were prepared by ion exchange method. Solutions of sodium polyphosphate (3 g in 25 mL of water), pyrophosphate (4 g in 27 mL of water), or polyphosphate (6.7 g in 30 mL of water) were loaded on the column containing 100 mL (bed volume) of the ion exchange resin prepared as above. The column was eluted with water, and fractions were collected. The fractions showing acidic pH (pH<3) were pooled. Triplicates of 0.5-mL aliquots of the pooled fraction containing the phosphate acid were diluted with 20 mL water and titrated with 0.100 N NaOH to the end point of pH 4.5-5.0 (Fisher analytical solution) to determine normality. The pooled fractions after ion exchange were titrated with trimethylamine (to obtain trimethylammonium salts) to pH 5.4-5.5. After titration, the solutions were diluted, if necessary, to obtain a final concentration of trimethylammonium close to 0.5 N.

Trimethylammonium and triethylammonium sulfates were prepared by diluting 1.39 mL of concentrated (17.9 M) sulfuric acid with 80 mL water, and titrating the diluted solution with neat triethylamine or aqueous trimethylamine under the control of a pH-meter to equivalence point (pH 5.1-5.5). The volume was adjusted to 100 mL with water.

Trimethylammonium citrate solution was prepared by dissolving 1.572 g of citric acid monohydrate ACS from Sigma (Product No. C-1909) in 20 mL of water, and titrating the solution with aqueous trimethylamine to the point of equivalence. The volume was adjusted to 25 mL with water.

The solutions were filtered through a 0.2-µm cellulose acetate filter using positive pressure. Osmolality and pH of the solutions was measured using a vapor pressure osmometer and glass-calomel electrode pH-meter, respectively. The normality of the anion in the phosphate solutions was determined by blue phosphomolybdate spectrophotometric assay (see Example 70) after acid hydrolysis (5 min. 100° C., 3N $H_2SO_4$). Anion normality took into account only the acidic functional groups that are substantially ionized at pH 5.5. Cation normality was determined on the basis of the added trialkylammonium base. The obtained solutions had the following properties (Table 4):

TABLE 4

Properties of substituted ammonium salt solutions for CPT-11 loading into liposomes.

| Salt | cation normality | anion normality | pH | Osmolality (mmol/kg) |
|---|---|---|---|---|
| TMA citrate | 0.58 | 0.60 | 5.1 | 791 |
| TMA sulfate | 0.50 | 0.50 | 5.4 | 625 |
| TMA pyrophosphate | 0.44 | 0.54 | 5.4 | 651 |
| TMA triphosphate | 0.57 | 0.68 | 5.4 | 695 |
| TMA polyphosphate | 0.49 | 0.58 | 5.5 | 336 |
| TEA sulfate | 0.54 | 0.50 | 5.35 | 719 |

Cholesterol and DSPC were purchased from Avanti Polar Lipids, Alabaster, Ala., USA. PEG-DSPE (PEG mol. weight 2,000) was from Shearwater Polymers, Huntsville, Ala., USA. DSPC, cholesterol, and PEG-DSPE in the weight ratio of 3:1:0.1 (molar ratio approximately 3:2:0.03) were dissolved in chloroform (Fisher; Optima grade, stabilized with amylene) at 60 mg/mL of DSPC. The solution was dispensed into Pyrex tubes at 30 mg of DSPC (0.5 mL) per tube and slowly evaporated at reduced pressure using rotary evaporator at 60° C. The lipid films were dried under vacuum (100 micron mercury, oil pump) for 30-60 minutes at room temperature.

Dry lipid films were hydrated by gentle shaking in the above aqueous salt solutions at 60° C. for 15-20 minutes. The lipids formed a milky suspension (multilamellar vesicles). This milky suspension was subjected to five cycles of freezing in the mixture of dry ice and isopropanol (−80° C., 3 minutes) and thawing in a water bath at 60° C. for 3 minutes. Then, the lipid suspension was extruded 10 times (double-strokes) through two stacked polycarbonate membrane filters (Nucleopore, Whatman, pore size 0.1 µm) using a manually operated reciprocating extruder (Avanti Polar Lipids) heated at 60° C.

The extruded liposomes were kept at 60° C. for five minutes and quenched in ice water (0-4° C.) for five minutes. Then, the liposomes were separated from the gradient-forming salt solution into the loading buffer MES-Dextrose (50 g/L of Dextrose ACS, 0.975 g/L of 2-(N-morpholino)-ethanesulfonic acid (MES), and sufficient amount of 5M NaOH to bring the pH to 6.4) by gel-chromatography on Sephadex G-75. Liposomes appear in the void volume fraction (approximately 30% of the column bed volume).

CPT-11 (Irinotecan hydrochloride) preparation containing 0.860 mg of the CPT-11 base per 1 mg of the solid was dissolved in 0.001N HCl to make a stock solution of 16.5 mg/mL CPT-11 base. This solution was mixed with the liposomes in MES-Dextrose buffer to achieve the ratio of 150 µg CPT-11 per 1 µmol of liposome phospholipids. The mixture was incubated at 55° C. in a water bath, with occasional gentle shaking (approximately every five minutes) for 30 minutes, then quickly chilled in ice water (0-4° C.). The liposomes were separated from the unencapsulated drug by gel-chromatography on Sephadex G-75, using MES-Dextrose as eluent. The encapsulated drug was determined by a spectrophotometric assay (Example 71), and the phospholipids determined using an extraction assay (Example 70).

In vitro drug release from so obtained CPT-11-loaded liposomes in the presence of 50% human plasma was studied as follows. Frozen human donor plasma was thawed as 37° C., centrifuged at 14,500 g for 10 minutes, and filtered through a 0.45-μm cellulose acetate syringe filter. The liposome preparations with loaded CPT-11 were sterilized by passage through 0.2-μm surfactant-free cellulose acetate (SFCA) sterile syringe filter. 0.5-mL of the liposomes were mixed with 0.5 mL of plasma in sterile 1.5-mL copolymer Eppendorf tubes, sealed, and incubated on a rocking platform at 37° C. for 24 hours. Blank sample contained 0.5 mL of sterile MES-Dextrose instead of liposomes. The liposomes were isolated by gel-chromatography on a beaded cross-linked 2% agarose gel (Sepharose CL-2B, Pharmacia; 10 mL bed volume) using 144 mM NaCl, 5 mM HEPES-Na, pH 7.4 buffer (HBS-5). The liposomes appeared at the void volume fraction, while plasma proteins and released drug (if any) were retarded by the gel. The liposome fractions were assayed for CPT-11 and phospholipids, and the drug/phospholipids ratio (output ratio) was determined. Readings of the blank samples (plasma only) were subtracted from the readings of the liposome-containing samples. Percent of the drug remaining in the liposomes after the incubation was determined by dividing output drug/lipid ratio by the input drug/lipid ratio (drug/lipid ratio prior to incubation with plasma). The loading and release data are summarized in Table 5.

TABLE 5

Loading of CPT-11 into liposomes with tertiary alkylammonium salts and in vitro release of the drug in the presence of human plasma.

| Entrapped salt solution | Before incubation with plasma | | After incubation with plasma | |
|---|---|---|---|---|
| | drug/lipid ratio | encapsulation efficiency (%) | drug/lipid ratio | drug remaining encapsulated (%) |
| TMA sulfate | 127.2 ± 5.6 | 84.8 ± 3.8 | 132.1 ± 6.9 | 103.8 ± 10.0 |
| TMA pyrophosphate | 136.2 ± 9.0 | 90.8 ± 6.0 | 132.3 ± 5.0 | 97.1 ± 10.1 |
| TMA triphosphate | 132.9 | 88.6 | 129.2 | 97.3 |
| TMA-Pn | 134.4 ± 9.3 | 89.6 ± 6.2 | 135.0 ± 7.4 | 100.4 ± 12.4 |
| TEA sulfate | 131.1 ± 6.5 | 87.4 ± 4.4 | 125.2 ± 5.0 | 95.5 ± 8.6 |

Example 8

In Vivo Stability of the Liposomes Loaded with CPT-11 Using Pyrophosphate, Triphosphate, Polyphosphate, Citrate, and Sulfate Trialkylammonium Salts While camptothecin liposomes may show acceptable drug leakage in blood plasma in vitro, the drug may leak more quickly in the blood circulation in vivo. Therefore, a panel of CPT-11 liposome formulations was screened for drug stability in the blood circulation in vivo using a single time point assay in mice.

The liposomes were prepared and loaded with CPT-11 as described in Example 6, with the following modifications. Instead of using PEG-DSPE from Shearwater Polymers, we used similar PEG-DSPE from Avanti Polar Lipids. To afford quantification of the liposome lipid matrix in the blood/tissue samples, a non-exchangeable radioactive label, [$^3$H]-Cholesteryl hexadecyl ether ([$^3$H]-CHE; (Amersham, USA) was added to the chloroform solution of the lipids in the amount of 0.25 mCi/mmol of phospholipids. The lipid solutions were dispensed into Pyrex tubes at 12 mg of DSPC/tube, and lipid films were formed by rotary evaporation/vacuum drying. Lipid films were hydrated in 0.7 mL of the gradient-forming substituted ammonium salt solutions. Lipid concentration in the liposomes with entrapped phosphate-containing salts was determined by radioactivity scintillation counting. The preparations without entrapped phosphate-containing salts were also assayed for phospholipids without extraction as described in Example 70, and used as lipid radioactivity standards. Portions of the liposome-drug mixtures prepared for the loading were saved and assayed to confirm the pre-loading ratio of the added CPT-11 to the liposome lipid prior to loading ("input ratio"). Volume-averaged mean and standard deviation of the liposome size distribution were determined by quasi-elastic light scattering (QELS) using Gaussian model. The properties of these liposomes are summarized in Table 6.

TABLE 6

Characterization of CPT-11 loading into [$^3$H]-CHE-labeled liposomes for in vivo stability study

| Entrapped salt solution | drug/lipid ratio before loading | drug/lipid ratio after loading | loading efficiency (%) | liposome size, (mean ± SD) nm |
|---|---|---|---|---|
| TMA citrate | 159.2 ± 3.5 | 156.7 ± 3.6 | 98.5 ± 4.4 | 122.1 ± 25.3 |
| TMA sulfate | 156.1 ± 2.5 | 156.1 ± 3.1 | 100.0 ± 3.6 | 122.2 ± 28.4 |
| TMA pyrophosphate | 164.6 ± 5.8 | 156.6 ± 4.3 | 95.2 ± 6.0 | 121.1 ± 19.9 |
| TMA triphosphate | 163.6 ± 5.7 | 156.0 ± 3.2 | 95.3 ± 5.3 | 122.4 ± 12.9 |
| TMA polyphosphate | 170.5 ± 8.0 | 162.4 ± 4.0 | 95.3 ± 6.8 | 123.0 ± 12.7 |
| TEA sulfate | 153. ± 3.3 | 154.9 ± 4.9 | 101.0 ± 5.3 | 121.1 ± 18.0 |

Six-week-old female CD-1 mice (Charles River) received tail vein injections of these liposomal CPT-11 formulations at the dose of 10 mg/kg (0.2 mg CPT-11/mouse) in duplicate. Eight hours later, the mice were anesthetized and exsanguinated through open heart puncture. The blood was collected into heparinized syringes (10-20 μl of 1000 U/ml heparin USP) and transferred into weighed tubes containing 0.4 ml of the phosphate-buffered physiological saline solution (PBS) containing 0.04% EDTA (Gibco BRL), kept on ice. The tubes were weighed to determine weights of the blood samples, blood cells were separated by centrifugation at 9,000 g for 5 minutes, and supernatants containing PBS-diluted plasma, were saved for drug and liposome lipid assays. CPT-11 was quantified by fluorometric assay (Example 71). Liposome lipid was quantified by quenching-corrected radioactivity scintillation counting. The liposome and phospholipid-radioactivity standards were counted in parallel with the plasma samples. Percent of the drug that remained encapsulated was calculated by dividing the drug/radioactivity ratio in the plasma samples by the drug/radioactivity ratio of the injected liposomes. Due to the fast elimination of free CPT-11 from the blood (see Example 69) and the known stability of the [$^3$H]-CHE against lipid exchange, the assays' readings were considered indicative of the blood content of liposomal CPT-11 and lipid. Percent of injected lipid dose (% I.D.) remaining in the circulation was calculated assuming 100% of the injected bolus entered the circulation; blood volume being 6.3% of the mouse body weight, and hematocrit of 45%. The results are summarized in Table 7.

TABLE 7

In vivo stability of CPT-11-encapsulation and circulation longevity of CPT-11-loaded liposomes in mice at a single point (8 hours) post injection. % I.D., % of injected dose.

| Liposome-entrapped salt | Drug/lipid ratio, % of pre-injection value | Liposome lipid, % I.D. in the blood |
|---|---|---|
| TMA citrate | 80.2 ± 7.8 | 18.8 ± 3.4 |
| TMA sulfate | 70.1 ± 4.8 | 23.6 ± 1.8 |
| TMA pyrophosphate | 67.3 ± 9.2 | 23.2 ± 3.1 |
| TMA triphosphate | 70.6 ± 6.0 | 24.9 ± 8.2 |
| TMA polyphosphate | 107.5 ± 8.9 | 24.3 ± 3.4 |
| TEA sulfate | 76.6 ± 13.1 | 23.6 ± 0.1 |

All preparations showed the level of drug encapsulation after 8 hours in the blood in vivo at 70-80% of the pre-injection level, while the liposomes containing polyphosphate were the most stable (drug encapsulation remains at about 100%).

Example 9

Blood Pharmacokinetics of CPT-11 Liposomes Prepared Using Riethylammonium Polyphosphate The formulation of liposomal CPT-11 using triethylammonium polyphosphate salt was prepared as outlined in Example 3. The lipids—DSPC, cholesterol, and N-(methoxy-poly(ethylene glycol) (M.w. 2000)-oxycarbonyl)-DSPE (PEG-DSPE) (all from Avanti Polar Lipids, Inc.)—were combined as dry powders in the molar ratio of 3:2:0.015 and dissolved in 100% ethanol (USP grade, approx. 0.15 mL/100 mg of the lipids) at 62-65° C. For pharmacokinetic studies, $^3$H-cholesteryl hexadecyl ether ($^3$H-CHE, obtained from Amersham Pharmacia) was added to the lipids in the amount of 0.5 mCi/mmol of phospholipids as a non-exchangeable radioactive lipid label. The aqueous solution of TEA-Pn (0.5 M triethylammonium, pH 5.7-6.2) was prepared as in Example 4. TEA-Pn solution (10 times the volume of added ethanol) was mixed with the lipid solution at 60-65° C. and stirred at this temperature until a homogeneous milky suspension of multilamellar vesicles was formed. This suspension was extruded 15 times through 2 stacked polycarbonate track-etched filters (Corning Nuclepore) with the pore size of 100 nm using argon pressure extruder (Lipex Biomembranes) at 60-65° C., and resulting unilamellar liposomes were quickly chilled in ice and then let attain ambient temperature. Ethanol and unincorporated polyphosphate salt were removed by gel chromatography on Sepharose CL-4B column eluted with MES-Dextrose buffer (5 mM MES, 50 g/L dextrose, pH adjusted to 6.5 with NaOH).

A stock solution of CPT-11 (Irinotecan hydrochloride) containing 20 mg/mL Irinotecan base in water was added to the liposomes at a drug/lipid ratio of 150-200 mg/mmol phospholipids, and the mixture was incubated with occasional agitation for 45-60 minutes at 60-62° C. The incubation mixture was quickly cooled down and incubated for 10 minutes at 0° C., then allowed to attain ambient temperature. 1/20 of the volume of 2.88 M NaCl was added to adjust to physiological ionic strength and improve the removal of membrane-bound CPT-11 (as opposed to the drug encapsulated within the liposome interior). Unencapsulated drug was removed by gel chromatography on Sephadex G-25 or G-75 column (Amersham Pharmacia) eluted with HBS-6.5 buffer (5 mM 2-(4-(2-hydroxyethyl)-piperazino)-ethylsulfonic acid (HEPES), 144 mM NaCl, pH 6.5). Liposome fractions eluted in the void volume were combined, sterilized by 0.2 micron filtration, and stored at 4-6° C. before use. The liposomes were characterized by lipid concentration, drug concentration, and particle size as in Example 7. The liposomes had the average size of 108 nm and CPT-11 content of 139±18 mg of CPT-11 base per mmol of phospholipids.

The longevity of the liposome lipid and liposome drug in the blood and the characteristics of drug release from the liposomes in vivo were studied in female Sprague-Dawley rats (190-210 g) with indwelling central venous catheters. The rats were injected with a 0.2-0.3 mL bolus of $^3$H-CHE-labeled Irinotecan liposomes (0.05 mmol phospholipids, or 7-8 mg CPT-11 per kg of the body weight). Blood samples (0.2-0.3 mL) were drawn at various times post injection using heparin-treated syringe. The withdrawn blood volume was replenished using phosphate buffered physiological saline. The blood samples were diluted with 0.3 ml of ice-cold PBS containing 0.04% EDTA, weighed, and the blood cells were separated by centrifugation. The supernatant fluids were collected and assayed for CPT-11 using the fluorometric procedure of Example 71, and for the liposome lipid label by scintillation radioactivity counting using conventional methods. The liposome preparations with known drug and $^3$H-CHE-lipid concentration were used as standards. Radioactivity standards contain equal amount of diluted rat plasma to account for quenching. The amount of CPT-11 and the liposome lipid in the blood was calculated assuming the blood volume in ml as 6.5% of the body weight in grams, and the hematocrit of 40%. The total amount of the lipid and the drug in the blood was expressed as % of injected dose (% I.D., % ID) and plotted against post-injection time. The percent of drug remaining in the liposomes was calculated by dividing the drug/lipid ratio in the blood samples by the drug/lipid ratio of the injected liposomes (taken as 100%). Because the plots generally showed good agreement with monoexponential kinetics (linearity in semi-logarithmic scale), blood half-lives of the drug, the lipid, and of the drug release from the liposomes, were calculated from the best fit of the data to monoexponential decay equation using the TREND option of the Microsoft EXCEL computer program (Microsoft Corp., USA). The results are shown on FIG. 1. From the best fit parameters, the blood half-lives for lipid and drug were 16.4 hours and 6.61 hours, respectively. Under these conditions, free CPT-11 clears from the circulation very rapidly (see Example 69).

Figure 2:
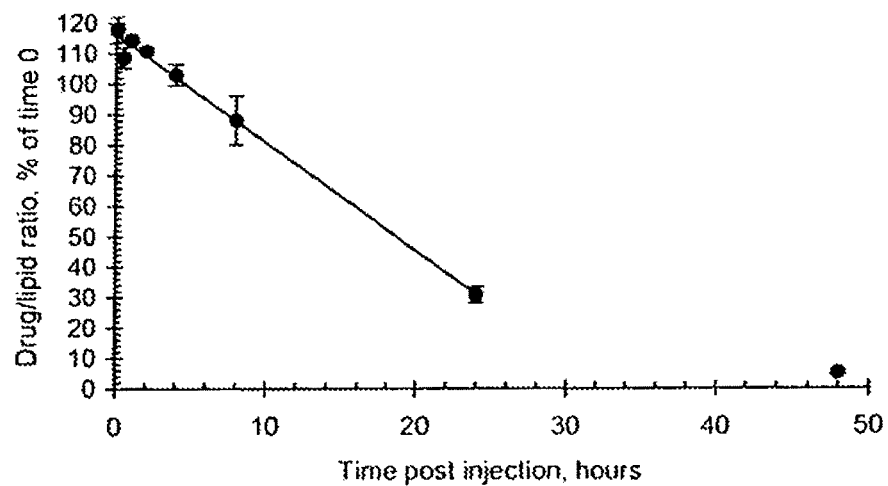
FIG. 2 shows the dynamics of drug-to-liposome lipid ratio in the blood of a rat in vivo following i.v. bolus administration of the liposome loaded with CPT-11 using TEA-Pn method (See Example 9).

The blood drug/lipid ratio revealed biphasic character of the CPT-11 release from the liposomes (FIG. 2). In the first 24 hours, the release of drug followed was linear over time (R=0.992) giving evidence for zero-order release kinetics. Only after about 75% of the drug was released at 24 hour time point, further release became non-linear. For 24 hours, the liposomes released the drug at a constant rate of about 3.6% of the initial load/hour. Thus, 50% of the drug was released over the period of approximately 14 hours. Zero-order release of the drug is an attractive quality in sustained release formulations, as the rate of drug release remains constant over time.

Example 10

Antitumor Efficacy of CPT-11 Liposomes Prepared Using Triethylammonium Polyphosphate Against Breast Cancer Xenografts in Nude Mice Antitumor efficacy of CPT-11 liposomes was studied in the model of human breast carcinoma BT-474, an estrogen-dependent ductal adenocarcinoma that over-expresses C-ErbB2 (HER2) receptor. BT-474 cells were obtained from American Type Culture Collection (Rockville, Md.). A BT-474 sub-line with higher tumor growth rate was established from a fast-growing xenograft tumor nodule raised as described below. The cells were propagated in vitro in RPMI-1460 medium with 10% fetal calf serum, 0.1 mg/mL streptomycin sulfate, and 100 U/ml Penicillin Gin T-150 flasks, and split 1:3 every week. NCR nu/nu female mice (4-6 week old; Taconic Farms) were subcutaneously implanted (at the base of tail) with 60-day sustained-release 0.72-mg 17β-estradiol pellets (Innovative Research of America, Inc.), and in two days were inoculated subcutaneously in the upper back area with 0.1 mL suspension containing $2 \times 10^7$ BT-474 cells in cell growth medium. The tumor progression was monitored by palpation and caliper measurements of the tumors along the largest (length) and smallest (width) axis twice a week. The tumor sizes were determined twice weekly from the caliper measurements using the formula (Geran, R. I., et al., 1972 *Cancer Chemother. Rep.* 3:1-88):

Tumor volume=[(length)×(width)$^2$]/2

At day 13 after inoculation, the tumor reached an average size of 200 mm$^3$ and the animals were randomly assigned to three groups of 13-15 animals.

Liposomal CPT-11 was prepared as in Example 8 (drug/phospholipid ratio 192 mg/mmol; average liposome size 86.8 nm). Free and liposomal CPT-11 were diluted with MES-dextrose vehicle to 5 mg/ml of CPT-11 base The animals were injected via the tail vein with free CPT-11, liposomal CPT-11, or vehicle only on days 14, 18, 21, and 25 post tumor inoculation. The drug-containing formulations were given at the dose of 50 mg CPT-11/kg per injection, which is the average of the doses reported in the literature for the CPT-11 studies in rodent tumor models.

Figure 3:
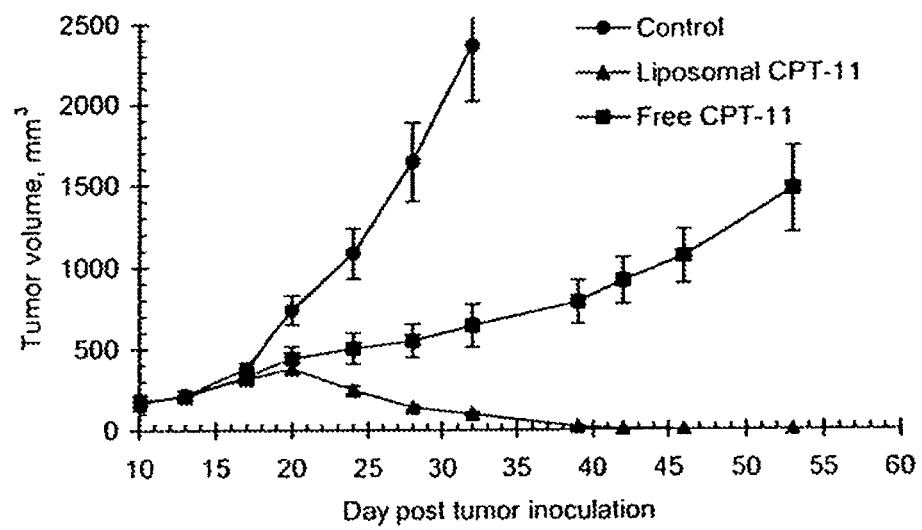
FIG. 3 shows antitumor efficacy of freeCPT-11 and liposomal CPT-11 against BT-474 human breast cancer xenografts in nude mice. "Control" designates the mice treated with drug- and liposome-free vehicle only. (See Example 10).

To assess treatment-related toxicity, the animals were also weighted twice weekly. The observations were made until day 60 post inoculation, at which time the estrogen supplementation pellet was exhausted. Average tumor volumes across the groups were plotted together and compared over time. As shown in FIG. 3, while free CPT-11 reduced the rate of tumor growth, in the group that received liposomal treatment the tumors regressed dramatically. While at day 36 in the control group the tumors reached the maximum allowable size averaging 3,500 mm$^3$, and at day 46 in the group treated with free drug the tumors were about 1,000 mm$^3$ at average, at the same time point none of the animals in the liposome-treated group had a palpable tumor.

Figure 4:
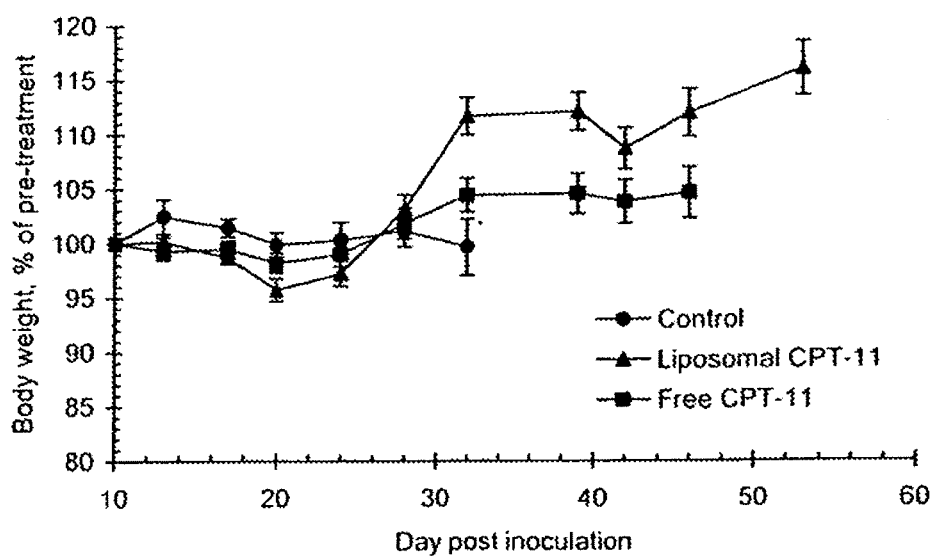
FIG. 4 shows the dynamics of the animals' body weights during the treatment of BT-474 tumor-bearing nude mice with free CPT-11 or liposomal CPT-11. "Control" designates the mice treated with drug- and liposome-free vehicle only. (See Example 10).

The treatment related toxicity was assessed by the dynamics of animals' body weight (FIG. 4). Neither group revealed any significant toxicity. The weight of the animals in the control group was consistently increasing. There was a slight decrease in the average body weight of the animals receiving liposomal CPT-11, by about 3.3%, on the day of the last treatment. This weight loss was reversed, however, and the animals reached their expected weight. This decrease in the mean body weight was not statistically significant by Student's t-test compared to pretreatment weight (p=0.274). Thus, all treatments were tolerated without significant toxicity.

Thus, the liposome formulation of CPT-11 obtained by loading of the drug via pre-entrapped sterically hindered substituted ammonium salt (triethylammonium) of a polyanionic, biodegradable polymer (polyphosphate) showed extended blood life, sustained release characteristics, and increased antitumor activity in the studied tumor model without an appreciable increase in toxicity.

Example 11

Comparative Assessment of CPT-11 Loaded Liposomes Prepared Using Pre-Entrapped Triethylammonium Salts: Effect of Liposome Size, Drug/Lipid Ratio, and the Nature of Pre-Entrapped Anion Two prototype formulations of CPT-11-loaded liposomes were prepared, one using the liposomes with pre-entrapped TEA-Pn, and the other with pre-entrapped TEA-SOS. Preparation of these liposomes included the following manufacturing steps.

1) Combining The Lipids By Co-Dissolving In Ethanol. The lipid matrix composition consisted of 1,2-Distearoyl-SN-phosphatidylcholine (DSPC) (Mol. wt. 790) 3 molar parts (59.8 mol. %); Cholesterol (Chol) (Mol. weight 387) 2 molar parts (39.9 mol. %); and N-(omega-methoxy-poly(ethylene glycol)-oxycarbonyl)-1,2-distearoylphosphatidyl ethanolamine (Mol. weight 2787) (PEG-DSPE) 0.015 molar parts (approx. 0.3 mol. %). DSPC and PEG-DSPE were purchased from Avanti Polar Lipids, Birmingham, Ala. Cholesterol (highest purity grade) was purchased from Calbiochem. Dry lipids were weighed with the accuracy of +0.1 mg in a borosilicate glass container and combined with absolute ethanol at the ratio suitable for the lipid dispersion step below. Because of the high transition temperature of DSPC (55° C.) the dissolution was typically performed at 55-60° C. until clear solution was obtained.

2) Preparing the TEA-Pn and TEA-SOS Solutions. Sodium polyphosphate (n=13-18) was from Sigma Chemical Co., p/n P 8510. Sodium sucrose octasulfate was purchased from Toronto Research Chemicals, Toronto, Canada, p/n S699020. The salts were weighed down and dissolved in water to provide 1.2-2.5 N solutions. Anion exchangers Dowex 50W×8-200 or Dowex HCR-W2 in H$^+$-form (available from Sigma) were used to convert the sodium salts into free acids. Before the first use, the resins were washed by stirring with 3 volumes of the following solutions, followed by decanting: (1) 1.0-1.2 M aqueous HCl 2 times; (2) Water 2 times; (3) 1.0-1.2 M aqueous NaOH 2 times; (4) Water 2 times; (5) 1.0-1.2 M aqueous HCL, 2 times. The suspension of washed resin in water was packed under gravity flow in a suitable size chromatography column to have at least 8 mL of the packed resin for each mL of the sodium salt solutions. The resin was further equilibrated by passage of 2 column volumes of 3.0-3.6 M aqueous HCL, followed by 5 column volumes of water or until the conductivity of the eluate falls below 1micro-S. After use, the columns were regenerated by sequential passage of: 1.0-1.2 M HCl—3 column volumes; 3.0-3.6 M HCl—2 column volumes; water—at least 5 column volumes, or until the conductivity of the eluate falls below 1 μS, and stored under 0.2-um filtered water at room temperature. The Pn and SOS sodium salt solutions were applied on the drained surface of the column (approximately 1 ml for each 4 ml of the packed resin volume) and allowed to flow under gravity at the rate of about 1-2 ml/min for the resin bed size of 75-150 mL. The column was eluted with water. The eluate was tested for conductivity. The fractions with 10 mS or higher conductivity were collected. If more concentrated solutions of polyacids are required, the collection can start at 20-50 mS, but at the expense of somewhat higher loss of the gradient-forming salt. In the case of polyphosphoric acid, the collected solution is kept refrigerated (0-4° C.) until the amine titration step because of the hydrolytic instability of the phosphodiester bond at low pH. The collected eluates would have a pH of less than 0.7 (typically about 0.4) and conductivity of about 120-200 mS. Optionally, the amine titration step is performed without delay because the stability of polyphosphate at low pH. HPLC-grade triethylamine (99.5+% purity) from Fisher, p/n 04884 was used to titrate the acid solutions obtained from ion exchange. The normality of neat TEA was determined by potentiometric titration. 0.100-mL Aliquots of TEA (0.100 ml) were taken into 20 ml of water in triplicate. The aliquots are titrated with 0.1 N HCl standard solution to the pH end point (glass electrode) of 5.5-6.0. The calculated normality (7.07 N) was close to the theoretical value of 7.17N. A measured volume of the polyphosphoric (Pn) acid or sucrose octasulfuric (SOS) acid solution was titrated with neat TEA under the control of pH (glass) electrode. Thorough stirring was required to disperse the amine. Titration endpoint was pH 5.6-6.2. The volume of added TEA was accurately recorded. The volume of titrated solution was measured, and the concentration of TEA was calculated on the basis of the added TEA volume and normality. Water was added as necessary to adjust the TEA concentration to required 0.55±0.05 N or 0.65±0.03 N, as indicated below. The amount of residual sodium in the obtained TEA-Pn or TEA-SOS solutions was determined by potentiometry using sodium-selective glass electrode (Corning). One mL of the solution was diluted with 19 mL of water, and the sodium concentration was determined using the increment method according to the electrode manufacturer's manual. The amount of residual sodium was less than 1 mM, typically less than 0.5 mM. The obtained TEA-Pn or TEA-SOS solutions were passed through 0.2 μm cellulose acetate sterile filter using positive pressure feed. The final pH and osmolality of the solutions was measured and recorded. We use pH calomel micro-combination all-glass electrode for pH measurements, and vapor pressure/dew point osmometer for osmolality measurements. The solutions were stored refrigerated until use.

3). Preparing lipid dispersion in the gradient-forming buffer by mixing of ethanolic Solution of the lipids with the gradient-forming buffer. The lipids were dispersed in the gradient-forming salt solution using ethanol mixing method. All steps were performed at 60-65° C. The lipids were dissolved in 100% Ethanol USP at a concentration of about 0.5-0.6 M of DSPC in a chemical resistant glass pear-shaped flask or tube. The gradient-forming salt solution (TEA-Pn or TEA-SOS) was pre-warmed to 60-65° C. and added to the ethanolic lipid solution at once, and the components were thoroughly mixed by swirling and/or vortexing. The final amount of ethanol was about 10 vol. %. For preparations of the scale in excess of 0.1 mmol phospholipid, the resulting suspension was placed on a rotary evaporator at 60-65° C. and vacuumized with rotation until the evolution of ethanol stopped, as manifested by the end of foam formation. For the scale of 0.1 mmol phospholipid or less, ethanol was not removed from the lipid dispersion at this step. The resulting lipid suspensions were kept at 60-65° C. and used promptly for the extrusion step.

4). Sequential extrusion of the lipid dispersion through defined pore membranes. For the lipid suspension volumes up to 1 mL we used a manually operated reciprocating extruder supplied by Avanti Polar Lipids. The extruder is charged with 19 mm track-etched filter membranes and thermostatted by virtue of a metal heating block. For the volumes from 1 to 10 mL, we used a thermostatted, gas pressure operated, unidirectional flow extruder from Lipex Biomembranes. The extruder is charged with 25 mm filter membranes. The lipid suspensions were repeatedly extruded at 60-65° C. using manual feed or argon gas pressure, as appropriate, through a series of 2 stacked polycarbonate membrane filters (the filters from Corning-Nuclepore and Osmonics Corp. were equally suitable) having nominal pore sizes of 100 nm, 80 nm, or 50 nm. Where the effect of liposome size was of interest, the extrusion was stopped at 100 nm, 80 nm, or 50 nm step. The exact type of filters used and number of extrusions is indicated below for each experiment. The extruded liposomes were kept at 60-65° C. for about 15 min. and quickly cooled down to 2-4° C. in an ice bath. After about 15 min. in the ice bath, the liposomes were allowed to reach room temperature.

5). Removal of extraliposomal gradient-forming buffer and transfer of the liposomes Into a drug-loading buffer. Non-encapsulated gradient-forming salt was removed, and the liposomes were transferred into the drug loading buffer using size exclusion chromatography (SEC). Tangential flow filtration, hollow fiber dialysis, of other scalable step can be used in scale-up manufacture. It is advantageous to ensure the complete removal of the extraliposomal polyanion by treatment of the liposomes with an anion-exchange resin (e.g., Dowex-1 or Dowex-2 quaternary ammonium cross-linked polystyrene beads). Drug-loading buffer contained 50 g/L anhydrous Dextrose USP, and 5 mM tissue-culture certified HEPES in water, adjusted to pH 6.5 with NaOH. The buffer was vacuum-filtered through 0.2 micron Nylon filter (Whatman). The extruded liposomes were chromatographed on a column with Sepharose CL-4B (Pharmacia) and eluted with the drug-loading buffer. The liposomes appeared in the void volume fraction and were collected, based on the eluate turbidity, in the volume of about 2× of that applied. The eluted liposomes were assayed for phospholipid concentration according to Example 70, particle size by QELS, and stored at 4-6° C.

6) Incubation of liposomes with the drug. Stock solution of CPT-11 (Irinotecan Hydrochloride) was prepared immediately before mixing with the liposomes by dissolving Irinotecan Hydrochloride in water to achieve concentration of 20 mg/mL drug base. The pH of the solution was between 4.0 and 5.0. The drug solution was filtered through 0.2 micron polyethersulfone (PES) sterile filter using positive pressure. Aliquots of the liposomes in the drug loading buffer produced at the step 5 above were mixed at room temperature with the stock Irinotecan solution to achieve the drug/lipid input ratio in the range of 0.15-0.55 g of drug for mmol of liposome phospholipid. Particular input drug/lipid ratios are indicated below, where appropriate. The pH of the mixtures was adjusted to 6.5 with 1 M NaOH, the mixtures in glass vials were incubated on the thermostatted water bath at 58-62° C. with slow agitation for 30-45 min, quickly cooled down in ice-water bath (0-2° C.), and left at this temperature for 15 min. Then the liposomes were allowed to warm up to room temperature for the next step (removal of unencapsulated drug and transfer into the storage buffer). This step resulted in the encapsulation efficiency of more than 95%, typically 98-100% in the whole range of studied drug/lipid ratios.

7). Removal of unencapsulated cpt-11, transfer of the liposomes into the storage buffer, final filtration, and storage. Unencapsulated drug was removed and the liposomes were transferred into the storage buffer using size exclusion chromatography. The storage buffer contained 20 mM HEPES, 135 mM NaCl, pH 6.5 (adjusted with NaOH) in water, and was 0.2-micron vacuum-filtered before use. Gel-chromatography on Sephadex G-75 (Amersham Pharmacia Biotech) was performed essentially as described under Step 2 above. CPT-11 liposomes eluted from the column (void volume fraction) were assayed for liposome phospholipid and CPT-11 (by spectrophotometry, see Examples 70 and 71), and volume-weighted mean particle size by QELS. The drug concentration was adjusted, if necessary, to be in the range of 2.0-4.0 mg/mL. The liposomes were filtered through 0.2 micron polyethersulfone sterile filters and aseptically dispensed into sterile polypropylene vials (Corning Cryo-Vials) or PTFE-lined screw-cap borosilicate 4-mL glass vials to approximately 70-80% of the vial volume. The vials were aseptically closed (in air), labeled, and stored at 4-6° C.

Example 12

Effect of Drug/Lipid Ratio on the Drug Loading Efficiency and In Vivo Drug Retention of TEA-Pn-Containing Liposomes Liposomes with entrapped aqueous 0.65N solution of TEA-Pn, pH 6.1, osmolality 531 mmol/kg, were prepared following the procedure of Example 11. The lipid dispersion was extruded ten times through two stacked 100 nm pore size polycarbonate filters. Liposome lipid matrix also included [$^3$H]-CHE at 0.5 mCi/mmol phospholipid. The liposome size before drug loading was 98.5±34.3 nm. The liposomes were loaded at initial drug-to-phospholipid ratios of 200, 300, 400, and 500 mg CPT-11/mmol phospholipid. The drug and phospholipid amounts in the liposomes were determined by spectrophotometry according to Example 71, and by phospholipid extraction-digestion-blue phosphomolybdate assay of Example 72, respectively.

To evaluate in vivo drug release rate, the method of Example 8 was followed. The liposomes were injected via tail vein into 6-week-old female Swiss Webster mice (body weight 18-22 g) at a dose of 5 mg CPT-11/kg. At 8 and 24 hours post injection, the mice, in groups of 3, were anesthetized, and exsanguinated via open heart puncture. The blood was mixed with 0.4 mL of ice-cold 0.04% EDTA in PBS, the blood cells were separated by centrifugation, and the plasma concentration of CPT-11 was measured by spectrofluorometry as described in Example 71. Lipid was determined by measuring the amount of [$^3$H]-CHE using quenching-corrected liquid scintillation counting, and the amount of drug retained in the liposomes was calculated by dividing the determined drug/lipid ratio by the drug/lipid ratio in the injected liposomes. Because of the fast blood clearance of free CPT-11, resulting in low blood level, we assumed that all assayed drug was in the liposomal form.

The results are presented in Table 8. The differences between drug retention among the groups were not statistically significant. As a result of these studies, we concluded that increasing the drug load up to 500 mg/mmol will not adversely affect drug loading or in vivo stability. This ratio was adopted for further studies.

TABLE 8

The effect of drug/lipid ratio on the drug loading and in vivo drug retention in Irinotecan TEA-Pn liposomes (average ± standard deviation).

| Drug/lipid ratio, mg/mmol phospholipid | | | Drug remaining in the liposomes, % of pre-injection value | |
|---|---|---|---|---|
| Input | Output | % loaded | After 8 hours | After 24 hours |
| 200 | 208.4 | 104.2 | 54.6 ± 9.9 | 9.72 ± 2.23 |
| 300 | 286.3 | 95.4 | 85.2 ± 14.3 | 14.52 ± 2.51 |
| 400 | 348.8 | 87.2 | 81.5 ± 18.3 | 17.31 ± 6.14 |
| 500 | 518.9 | 103.8 | 66.8 ± 19.6 | 13.47 ± 1.44 |

Example 13

Drug Loading Efficiency of CPT-11 Loading into TEA-SOS-Containing Liposomes: Effect of Liposome Size and In Vivo Drug Retention in Mice Liposomes with entrapped solutions containing prepared as in Example 11 using gradient forming solution having 0.643 N TEA-SOS, pH 5.7, osmolality 530 mmol/kg. Lipid dispersion was extruded ten times through two stacked polycarbonate filters with the pore size of 50 nm, 80 nm, or 100 nm. Liposome lipid matrix also included [$^3$H]-CHE at 1.5 mCi/mmol of liposome phospholipid. The liposome size was determined by dynamic light scattering. The liposomes were loaded with CPT-11 at initial drug-to-phospholipid ratios of approximately 550 mg Irinotecan/mmol of phospholipid. The drug loaded liposomes were sized by QELS and assayed as described in Examples 70 and 71.

Female Swiss Webster mice (8-10 weeks, average 27-30 grams) were injected via tail vein with these CPT-11 liposome formulations at a drug dose of 10 mg/kg. The mice were sacrificed at 24 h and the blood was collected and assayed for CPT-11 and liposome lipids as in Example 11. The results are summarized in Table 9.

TABLE 9

Irinotecan loading and in vivo drug retention in TEA-SOS liposomes.

| Extrusion membrane pore size, nm | Liposome size, nm mean SD | Drug load, mg Irinotecan/mmol phospholipid | Drug remaining in the liposomes after 24 hours in mice, % of pre-injection value |
|---|---|---|---|
| 50 | 87.6 ± 28.1 | 579.3 ± 24.2 | 79.2 ± 3.8 |
| 80 | 98.5 ± 15.1 | 571.1 ± 69.7 | 82.6 ± 2.1 |
| 100 | 110.8 ± 25.2 | 567.7 ± 37.7 | 86.2 ± 2.7 |

Surprisingly, the liposomes with triethylammonium salt of sucrose octasulfate, a non-polymeric polyanionized organic hydroxylated organic compound (sugar), provided dramatically better (4-5 fold) in vivo drug retention in liposomes compared with similar liposomes with a polyanionic polymer (polyphosphate).

Example 14

Blood Pharmacokinetics of CPT-11-Loaded SOS-TEA Liposomes in Rats

Figure 5:
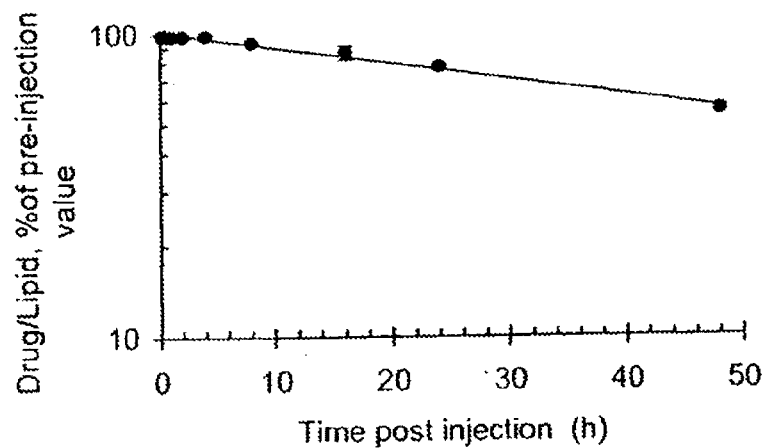
FIG. 5 shows the dynamics of drug-to-liposome lipid ratio in the blood of a rat in vivo following i.v. bolus administration of the liposome loaded with CPT-11 using TEA-SOS method. (See Example 14).

Liposomes (100 nm extrusion membrane pore size) were prepared as described in Example 12 The liposomes was administered intravenously at a dose of 10 mg CPT11/kg to two nine-week-old female Sprague Dawley rats (Harlan) (body weight about 200 g) with indwelling central venous catheter at a dose of 10 mg CPT-11/kg (17.6 μmol of phospholipids/kg). Blood samples were taken at prescribed time points and analyzed for drug and liposome lipid content as in Example 9. The data were expressed as the % injected lipid dose/ml of plasma and the % drug retained inside the liposome at each time point, plotted against post injection time, and half-lives for liposome lipid, as well as half-lives for drug release from the liposomes, were calculated by best fit to a monoexponential kinetic model (FIG. 5). The half-life of drug release from CPT-11 loaded TEA-SOS liposomes was 56.8 hours, much longer than that of the similar TEA-Pn liposomes.

Example 15

Antitumor Activity of Free CPT-11, and CPT-11 Encapsulated into TEA-Pn and TEA-SOS-Containing Liposomes in Athymic Nude Mice Bearing Subcutaneous Xenografts of Human Colon Carcinoma (HT-29)

The liposomes were prepared as in Example 11 using TEA-Pn solution with 0.65 M TEA, pH 6.1, and osmolality 531 mmol/kg, or TEA-SOS solution with 0.643 M TEA, pH 5.7, and osmolality 530 mmol/kg. The extrusion included 10 passages through two stacked polycarbonate membranes with pore size 100 nm. The resulting TEA-Pn and TEA-SOS liposomes had the size of 112.3±15.5 nm and 120.5±42.5 nm, respectively (mean±SD of the size distribution). The liposomes were loaded with CPT-11 at the input drug/phospholipids ratio of 500 mg/mmol. The resulting liposomes had the drug content of 465.6±26.5 (93% loading efficiency) and 499.9±22.5 mg (100% loading efficiency) of CPT-11/mmol phospholipid for the TEA-Pn and TEA-SOS formulations, respectively.

HT-29 cells were obtained from American Type Culture Collection, Rockville, Md., and propagated in DMEM medium supplemented with 10% fetal calf serum, 50 U/ml penicillin G, and 50 μg/mL of streptomycin sulfate at 37° C., 5% $CO_2$ as recommended by the supplier. NCR nu/nu homozygous athymic male nude mice (6 week old, weight at least 16 g) were obtained from Charles River. The mice were inoculated subcutaneously in the right flank with 0.1 mL of the suspension containing $5 \times 10^6$ cells suspended in the growth medium without antibiotics. Eleven days later the animals having tumors with the size between 150 mm$^3$ and 350 mm$^3$ were assigned to the treatment groups according to the following method. The animals were ranked according to the tumor size, and divided into 6 categories of decreasing tumor size. Six treatment groups of 11 animals/group were formed by randomly selecting one animal from each size category, so that in each treatment group all tumor sizes were equally represented. Starting at day 13, the animals received four tail vein injections, at the intervals of 4 days, of the following preparations: 1) Control (HEPES-buffered saline pH 6.5); 2) Free CPT-11 50 mg/kg, administered as freshly prepared 5 mg/mL solution in unbuffered physiological saline; 3) TEA-Pn liposomal CPT-11 at 25 mg/kg per injection; 4) TEA-Pn liposomal CPT-11 at 50 mg/kg per injection; 5) TEA-SOS liposomal CPT-11 at 25 mg/kg per injection; 6) TEA-SOS liposomal CPT-11 at 50 mg/kg per injection. The animal weight and tumor size were monitored twice weekly as described in Example 10. The weight of tumor was subtracted from the animal weighing results to obtain animal body weight. The animals were observed for 60 days following tumor inoculation. When the tumors in the group reached 20% of the mouse body weight, the animals in the group were euthanized. There were complete tumor regressions in some groups without the signs of tumor regrowth at the end of study. The tissues from the tumor inoculation site from these animals were collected and preserved for pathological analysis for residual tumor cells.

Figure 6:
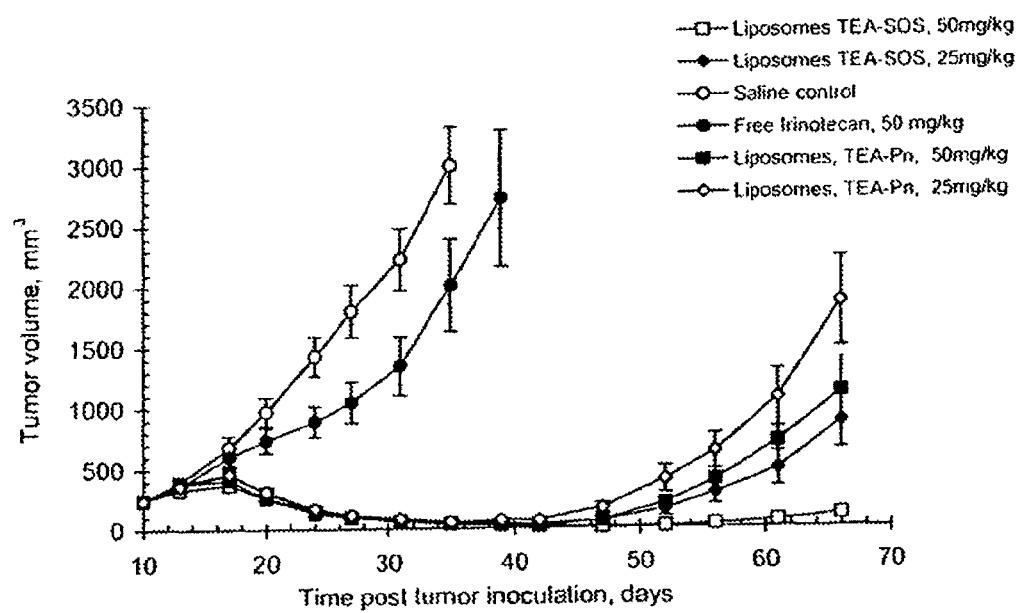
FIG. 6 shows antitumor efficacy of free and liposomal CPT-11 against HT-29 human colon cancer xenografts in nude mice. The on-panel caption indicates the drug loading method and the administered dose per injection. "Saline control" designates the mice treated with drug- and liposome-free vehicle only. (See Example 15).
Figure 7:
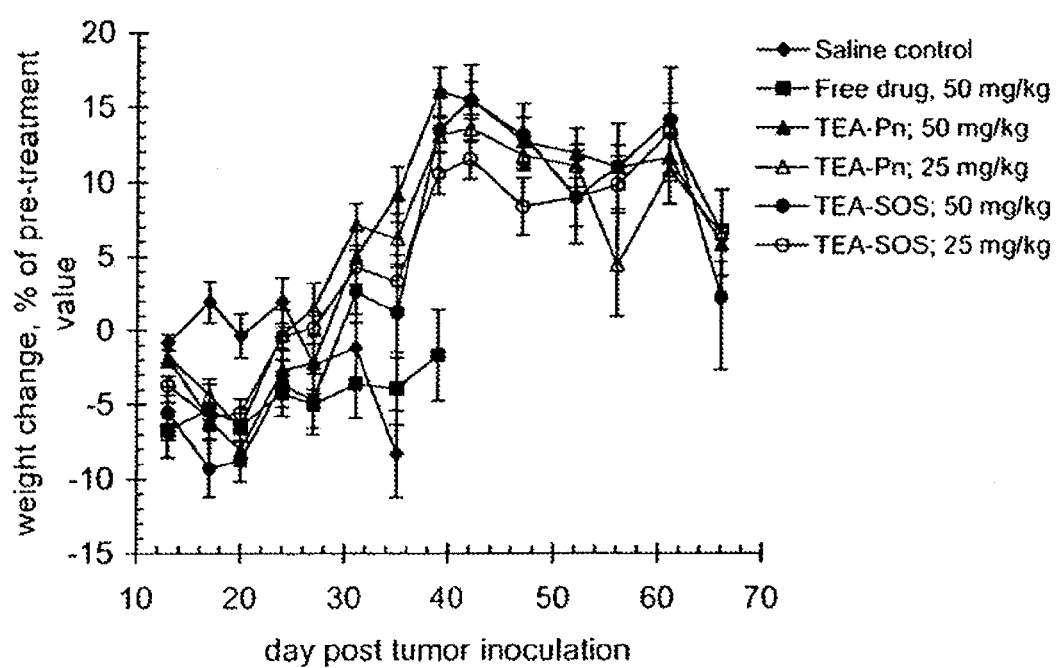
FIG. 7 shows the dynamics of the animals' body weights during the treatment of HT-29 tumor-bearing nude mice with free or liposomal formulations of CPT-11. The error bars represent standard deviation of the data. "Saline control" designates the mice treated with drug- and liposome-free vehicle only. (See Example 15).

The results of this study are shown in FIGS. 6 and 7. Free CPT-11 had only minor effect on the tumor growth. All liposomes had pronounced effect resulting in tumor regression later followed by regrowth in most animals. 50 mg/kg dose was more effective than 25 mg/kg dose in both TEA-Pn and TEA-SOS CPT-11 liposomes. Average tumor doubling times calculated from the tumor size data (FIG. 7) were: control—4.2 days; free drug, 50 mg/kg-4.8 days; TEA-Pn liposomal drug, 25 mg/mg-43.6 days; TEA-Pn liposomal drug, 50 mg/kg-47.5 days; TEA-SOS liposomal drug at 25 mg/kg-48.2 days, and TEA-SOS liposomal drug at 50 mg/kg—over 56 days (doubling time was not reached). Thus, liposomal CPT-11 prepared according to the present invention was at least about 10-fold more active than the free drug, given at the same dose and schedule. Unexpectedly, TEA-SOS CPT-11 liposomes were prominently more effective in reducing tumor growth than TEA-Pn CPT-11 liposomes administered at the same dose. While in the groups treated with free drug and TES-Pn liposomal drug at 50 mg/kg per injection there were no animals without tumor regrowth, in the groups receiving 25 mg/kg of each liposomal formulation, one animal (9.1%) was tumor-free at the end of study, and in the group receiving 50 mg/kg of TEA-SOS liposomal CPT-11 formulation, at the end of study 4 animals (36.4%) were tumor-free without signs of regrowth.

The drug manifested some toxicity. The animals receiving free CPT-11, but not liposomal CPT-11, experienced temporary morbidity (loss of alertness, humped posture, ruffled fur, decreased mobility) for about one hour after drug injection. The animals receiving free CPT-11 suffered permanent loss of about 6% of weight during treatment, and did not recover, The animals receiving both liposomal CPT-11 formulations experienced transient weight loss at the time between second and third injections averaging about 5% (at 25 mg/kg) or about 9% (at 50 mg/kg) of the pre-treatment value, and eventually attained normal weight. Therefore, the toxicity of liposomal drug was not more than that of the free (non-liposomal) drug, while the efficacy of the liposomal drug was substantially higher. The weight loss was reversed when the drug treatment was finished, and all animals recovered their weight without terminal morbidity or toxic deaths. Later on, the animals gained weight concomitantly with tumor regressions. In the saline control group, animals that developed large tumors experienced weight loss evidently due to tumor-related morbidity. Overall, the liposome drug formulation where the drug was loaded into the liposomes having pre-entrapped polyanionized sugar (sucrose octasulfate) proved to be the most efficacious while having less toxicity than the non-liposomal drug.

Example 16

Toxicity of Free and Liposomal CPT-11 in Mice

Acute toxicities of free CPT-11 and liposome-encapsulated CPT-11 prepared according to the present invention were compared by determining the maximum tolerated dose (MTD) following single i.v. injection in regular (immunocompetent) mice.

The following materials were used:

1) CPT-11 (Irinotecan Hydrochloride) preparation having Irinotecan Hydrochloride 98.9% by HPLC, and moisture 7.6%. In this study drug formulations were prepared on the "as is" basis, without correction for the moisture content or the Irinotecan base content.

2) Liposomal CPT-11 (Ls-CPT-11) was prepared as in Example 11, using lipid matrix of DSPC 200 mol. parts, Cholesterol 133 mol. parts, PEG-DSPE 1 mol. part; entrapped solution TEA-SOS having 0.65 M TEA, pH 6.4; drug loaded into liposomes in 5 mM HEPES buffer, 5% dextrose, pH 6.5, at 60° C. for 30 min at the input drug/lipid ratio 500 mg drug/mmol of phospholipid. Loading efficiency was >99%. Liposome size (volume average mean±standard deviation by QELS): 101±37 nm. Liposomes were formulated in the vehicle, 20 mM HEPES-Na, 135 mM NaCl; pH 6.5. Drug concentrations in the injected formulations were as stated in the Tables below.

3) Free CPT-11 solution. Free drug stock solution was prepared by dissolving Irinotecan Hydrochloride in 5% aqueous dextrose at 22 mg/mL, and sterilized by 0.2-μm filtration. This stock solution was diluted with sterile 5% dextrose prior to injection.

4) Animals. Female Swiss Webster mice, 6-8 week old, were from Harlan, USA.

MTD determination generally followed the protocol adopted by the United States National Cancer Institute Developmental Therapeutics Program. The protocol included the following three steps:

Step 1): Range-seeking step with the dose escalation factor of 1.8. The groups of two animals were injected into the tail vein with increasing doses of the free or liposomal Irinotecan, beginning with the dose of 60 mg/kg, and continuing with the dose escalation factor of 1.8, until acute mortality or terminal morbidity (within >1 day post injection) is observed in any of the animals. The dose one step below the mortality/terminal morbidity dose is recorded.

Step 2): Range-seeking step with the dose escalation factor of 1.15. The groups of two animals were injected into the tail vein with increasing doses of the free or liposomal Irinotecan, beginning with the dose recorded at Step 1, and continuing with the dose escalation factor of 1.15, until acute mortality or terminal morbidity (within >1 day post injection) is observed in any of the animals. The dose one step below the mortality/terminal morbidity dose is recorded at tentative MTD.

Step 3): Validation step. The group of 5 animals is injected i.v. (tail vein) with free or liposomal Irinotecan at tentative MTD determined at Step 2. The animals are followed for 7 days, the animal body weight is recorded twice weekly and compared with the pre-injection weight. General health of the animals is observed (alertness, grooming, feeding, excreta, skin, fur, and mucous membrane conditions, ambulation, breathing, posture). If during the observation period there is no mortality, progressive morbidity, or weight loss in excess of 15% of the pre-injection body weight, the dose is considered to be validated as acute single injection MTD. If any of these effects occur, the experiment is repeated at the next lower dose by a factor 1.15.

To obtain additional statistics for validation step, the body weight dynamics of surviving animals was followed for up to 11 days post injection. The dose of more than 324 mg/kg of the liposomal Irinotecan was impossible to administer because of the concentration and injection volume limitations. The results are presented in Table 10.

TABLE 10

MTD seeking study of CPT-11 formulations in mice.
RESULTS

Step 1. increase dose by a factor of 1.8

| drug | inj. Dose (mg/kg) | drug conc. (mg/ml) | Inj. volume (μl) | mouse # | 0 (g) | 1 (g) | 2 (g) | 4 (g) | 5 (g) | 6 (g) | 7 (g) | 11 (g) |
|---|---|---|---|---|---|---|---|---|---|---|---|---|
| Ls-CPT11 | 60 | 8 | 150 | 1 | 19.2 | 18.0 | nd | 20.3 | 20.6 | 20.6 | 20.0 | 19.7 |
|  |  |  |  | 2 | 19.7 | 19.3 | nd | 20.6 | 20.4 | 19.6 | 19.7 | 20.7 |
|  | 100 | 12 | 165 | 1 | 19.5 | 18.6 | nd | 19.6 | 20.0 | 20.1 | 19.4 | 19.9 |
|  |  |  |  | 2 | 20.1 | 18.9 | nd | 20.2 | 21.5 | 22.2 | 21.8 | 22.5 |
|  | 180 | 22 | 165 | 1 | 19.4 | 18.4 | nd | 18.9 | 19.7 | 20.5 | 19.5 | 20.5 |
|  |  |  |  | 2 | 20.0 | 19.3 | nd | 19.6 | 20.6 | 21.4 | 21.6 | 21.7 |
|  | 324 | 30.6 | 210 | 1 | 21.8 | 21.2 | 21.2 | nd | 20.2 | nd | 20.2 | nd |
|  |  |  |  | 2 | 21.6 | 20.4 | 21.3 | nd | 20.8 | nd | 21.4 | nd |
| free CPT11 | 60 | 8 | 150 | 1 | 20.6 | 20.4 | nd | 22.1 | 22.1 | 22.2 | 22.0 | 22.5 |
|  |  |  |  | 2 | 19.5 | 19.1 | nd | 20.2 | 20.3 | 20.4 | 20.5 | 21.1 |
|  | 100 | 12 | 165 | 1 | 19.3 | died 1-2 min after injection |  |  |  |  |  |  |
|  |  |  |  | 2 | 20.1 | died 1-2 min after injection |  |  |  |  |  |  |
|  |  |  |  | 3 | 19.9 | died 1-2 min after injection |  |  |  |  |  |  |

After injection, all mice treated with free CPT11 were sick, short of breath for about 1 h and then recovered
After injection, all mice treated with Ls-CPT11 were normal.

Step 2. increase dose by a factor of 1.15

| drug | inj. Dose (mg/kg) | drug conc. (mg/ml) | Inj. volume (μl) | mouse # | 0 (g) | 1 (g) | 2 (g) | 5 (g) | 7 (g) |
|---|---|---|---|---|---|---|---|---|---|
| free CPT11 | 60 | 8 | 150 | 3 | 19.9 | 20.0 | 20.9 | 19.9 | 21.3 |
|  |  |  |  | 4 | 19.5 | 18.7 | 19.4 | 18.8 | 18.9 |

TABLE 10-continued

| | | | | | | | | |
|---|---|---|---|---|---|---|---|---|
| 70 | 8 | 175 | 5 | 20.9 | 20.0 | 20.6 | 19.3 | 20.4 |
| | | | 6 | 22.3 | 21.8 | 22.4 | 22.4 | 22.8 |
| 80 | 8 | 200 | 7 | 20.6 | 19.9 | 20.1 | 19.9 | 20.9 |
| | | | 8 | 20.6 | 20.8 | 21.1 | 20.7 | 21.4 |
| 90 | 12 | 150 | 9 | 22.3 | died 1-2 min after injection | | | |
| | | | 10 | 22.4 | died 1-2 min after injection | | | |
| | 8 | 225 | 11 | 20.6 | died 1-2 min after injection | | | |

Step 3. Validation

| drug | inj. Dose (mg/kg) | drug conc. (mg/ml) | Inj. volume (µl) | mouse # | Animal body weight, at day post injection | | | |
|---|---|---|---|---|---|---|---|---|
| | | | | | 0 (g) | 3 (g) | 5 (g) | 7 (g) |
| free CPT11 | 80 | 8 | 200 | 1 | 20.2 | 19.3 | 20.0 | 21.7 |
| | | | | 2 | 20.5 | 20.6 | 20.5 | 21.2 |
| | | | | 3 | 20.7 | 20.6 | 20.8 | 21.9 |
| | | | | 4 | 20.8 | 21.4 | 22.1 | 23.0 |
| | | | | 5 | 21.9 | 21.9 | 21.6 | 21.5 |
| Ls-CPT11 | 324 | 36.5 | 180 | 6 | 21.0 | 20.0 | 20.1 | 20.2 |
| | | | | 7 | 20.4 | 20.4 | 20.2 | 19.2 |
| | | | | 8 | 20.4 | 19.8 | 20.3 | 20.7 |
| | | | | 9 | 20.9 | 19.9 | 20.5 | 21.5 |
| | | | | 10 | 20.7 | 19.5 | 19.8 | 20.2 |

Thus, while the MTD of free CPT-11 was 80 mg/kg, the MTD of liposomal CPT-11, surprisingly, was not achieved even at the highest administered dose of 324 mg/kg. Therefore, liposome encapsulation of CPT-11 according to the present invention has reduced the drug toxicity at least 4-fold.

Example 17

Storage Stability of CPT-11-Loaded TEA-SOS Liposomes Against Drug Leakage

Five batches of liposomal CPT-11 were prepared using the TEA-SOS method (Example 11), at the drug/lipid input ratio of 500-550 mg/mmol phospholipid. The liposomes were prepared using membrane extrusion through polycarbonate membrane with 80 nm or 100 nm pore size, as indicated in the table below. The liposomes were 0.2-µm filter sterilized and stored at 3.4-14.5 mg/mL of CPT-11 in 135 mM NaCl, 20 mM HEPES-Na, pH 6.5 (storage buffer), at 4-8° C. After the indicated storage time, the leaked drug was removed by gel-chromatography on Sephadex G-75 using the storage buffer as eluent. The drug and phospholipid concentrations in the liposomes before and after gel-chromatography were assayed using spectrophotometry method and acid digestion-blue phosphomolybdate method, respectively, as described in Examples 70 and 71. CPT-11 liposomes prepared according to the present invention were very stable. The leakage of CPT-11 from these liposomes during storage was less than 5% over 6 months (Table 10).

TABLE 11

Encapsulation stability of CPT-11 liposomes during storage (data are mean ± SE).

| Liposome Lot # | Extrusion pore size, nm | CPT-11 concentration, mg/ml | Storage time, months | % drug remaining encapsulated |
|---|---|---|---|---|
| 1 | 80 | 3.44 ± 0.06 | 6 | 99.02 ± 3.77 |
| 2 | 80 | 7.88 ± 0.19 | 6 | 102.38 ± 4.78 |
| 3 | 100 | 4.57 ± 0.06 | 6 | 96.38 ± 4.69 |
| 4 | 100 | 4.62 ± 0.11 | 6 | 95.72 ± 4.36 |
| 5 | 80 | 14.52 ± 0.42 | 3 | 103.4 ± 5.92 |

Example 18

Liposomes Loaded with Topotecan

Liposomes with entrapped TEA-Pn solution and TEA-SOS solution were prepared as in Example 11. Stock solution of Topotecan Hydrochloride (GlaxoSmithKline, PA, USA) was prepared immediately before mixing with the liposomes by dissolving Topotecan Hydrochloride in water at 15-20 mg/ml, counting on the actual Topotecan HCl content. The pH was adjusted to 3.0 with 1 N HCl. The drug solution was filtered through 0.2 micron polyethersulfone (PES) sterile filter using positive pressure. Aliquots of the TEA-Pn or TEA-SOS-containing liposomes in the drug-loading buffer were mixed at room temperature with the stock Topotecan HCl solution to achieve the drug/lipid input ratio in the range of 0.15-0.45 g/mmol of liposome phospholipid. Preferred ratio was 0.35 g of Topotecan HCl for mmol of liposome phospholipid. The mixtures in glass containers were incubated on the thermostatted water bath at 55-62° C. with slow agitation for 30-60 min, quickly cooled down in ice-water bath (0-2° C.) and left at this temperature for 5-15 min. This step resulted in the encapsulation efficiency of 89-90% (TEA-Pn gradient) or 97-100% (TEA-SOS gradient). Unencapsulated Topotecan was removed, and the liposomes were transferred into the storage buffer using size exclusion column chromatography. Before application on the column, the ionic strength of the liposome preparation was increased by mixing with 1/20 vol. of 2.88 M aqueous sodium chloride, and the mixture was incubated for about 15 min. We unexpectedly found that adjusting the ionic strength of the liposome medium from the low value during the loading (typically equivalent to less than 20 mM NaCl) to the higher value of above 20 mM NaCl, and preferably to 50 mM NaCl and above, improved the removal of unencapsulated drug and increased the stability of Topotecan-loaded liposomes against aggregation, possibly by facilitating the removal of membrane-bound Topotecan, as opposed to the drug encapsulated in the liposome interior. The rest of the procedure followed Example 11, step 7. For the results, see Table 12 below.

Example 19

Preparation of Anti-HER2-Immunoliposomal Formulations of Topotecan

Topotecan immunoliposomes specifically internalizable by cancer cells overexpressing HER2 (C-ErbB-2) surface receptor tyrosine kinase oncoprotein were prepared by conjugating Topotecan liposomes to anti-HER2 single chain human Fv antibody fragment, F5, selected from the phage display library for its high internalization into HER2-overexpressing cells (Poul, et al., 2000, J. Molecular Biology, v. 301, p. 1149-1161). F5 is a 27-KDa protein that binds to extracellular domain of HER2 receptor with affinity of about 150 nM, causing rapid internalization (Neve, et al., 2001, Biophys. Biochim. Res. Commun. v. 280, p. 2'74-2'79). For liposome conjugation, the method of U.S. Pat. No. 6,210,707 and of Nielsen, et al. (2002), Biochim. Biophys. Acta, v. 1591, p. 109-118, were generally followed. A hydrophilic lipopolymer conjugate of F5 was first prepared. C-terminus of F5 amino acid chain had an added terminal cysteine group (F5Cys). The F5Cys construct was expressed in *E. coli* and isolated from the bacterial lysate by Protein A column chromatography. Protein A eluted fractions were adsorbed on anion-exchange resin to remove pyrogens and host DNA, and treated with a thiol reducing agent to liberate the thiol group of the terminal cysteine. The reduced F5Cys was further purified by ion exchange chromatography using SP Sepharose Fast Flow (Amersham Pharmacia). The purified protein was conjugated to a thiol-reactive lipid-poly(ethylene glycol) linker, N-(3-(N-maleimido)propyonylamido)-poly(oxyethylene)-oxycarbonyl)-1,2-distearoylphosphatidyl ethanolamine (Mal-PEG-DSPE), a derivative of PEG with mol. weight 2,000 (FIG. 4.1), commercially produced by Avanti Polar Lipids, Inc., Alabama, USA. The protein and the linker were incubated in aqueous buffer solution at the molar ratio of 1:4, and the un-reacted linker was quenched with 1 mM cysteine. During the reaction, terminal cysteine of F5Cys is covalently attached to maleimido group of the linker. The resulting F5-PEG-DSPE conjugate was water soluble in the form of micelles having high apparent molecular weight (500-850 KDa), and was separated from unreacted protein (about 25%) by size exclusion chromatography. The amount of protein in the purified conjugate was determined by UV spectrophotometry at 280 nm, and the amount of the linker was assayed using a spectrophotometric method identical to that used for phospholipid quantification (see Example 70) The purified F5-PEG-DSPE conjugate was stable in water, fully immunoreactive, and was stable against denaturation and loss of reactivity for at least 1 hour at 65° C. and at least 3 months at 37° C.

To prepare anti-HER2 immunoliposomal Topotecan, Topotecan-loaded liposomes of Example 18 were mixed with F5-PEG-DSPE in the aqueous saline buffer at the ratio of 15 microgram of protein per 1 micromole of phospholipid (about 45 F5 copies per liposome). The mixture was incubated for 40 min. at 60° C., chilled on ice, and chromatographed on a column with Sepharose CL-4B (cross-linked 4% agarose beads, Amersham Pharmacia) to remove residual micellar conjugate, unconjugated protein, and any traces of extraliposomal drug that may have been released during the incubation. The liposomes with membrane-incorporated F5-PEG-DSPE were eluted with 5 mM HEPES-144 mM NaCl buffer pH 7.4, collected in the void volume of the column, sterile-filtered and dispensed for storage (4-6° C.). The amount of liposome-incorporated F5 was typically >80% of the added conjugate. It was determined by SDS-PAGE of the liposomes with quantification of the Coomassie-stained F5 band by densitometry. Drug and lipid concentrations in the immunoliposome preparations were determined similarly to non-targeted liposomes. The properties of Topotecan liposomes and F5-immunoliposomes (Examples 18-19) are summarized in Table 12.

TABLE 12

Characteristics of Topotecan liposomes and immunoliposomes.

| Liposome-entrapped salt | F5 scFv attachment: | Drug/lipid ratio, g/mol phospholipid | | % encapsulation | Liposome size, Mean ± SD, nm |
|---|---|---|---|---|---|
| | | Input | Output | | |
| TEA-Pn | No | 173.6 | 155.2 ± 5.9 | 89.4 ± 3.4% | 96.4 ± 38.7 |
| TEA-Pn | Yes | 173.6 | 156.2 ± 5.2 | 90.0 ± 3.0% | 96.2 ± 33.8 |
| TEA-SOS | No | 347.2 | 340.8 ± 14.7 | 98.2 ± 4.2% | 99.1 ± 32.6 |

Example 20

Effect of Loading Buffer pH and Drug/Lipid Ratio on the Topotecan Loading into Liposomes Liposomes (DSPC/Chol/PEG-DSPE, 3:2:0.015 molar ratio) with entrapped 0.5 N TEA-Pn, pH 6.2, osmolality 413 mmol/kg, were prepared using the ethanol injection method (Example 18), extruded through two stacked polycarbonate filters with 100 nm pore size 5 times and with 50 nm pore size 10 times. The loading buffer was 5 mM MES, 50 g/L Dextrose, adjusted to various pHs in the range 5.0-6.5. The liposome size was 73.1±21.3 nm by QELS. The liposomes were loaded by mixing a Topotecan stock solution (20 mg/ml) with the liposomes in the loading buffer at the input drug-to-phospholipid ratio of 100 mg/mmol, incubating the mixture at 60° C. for 45 min, quenching on ice for 15 min and removing the unencapsulated drug using a Sephadex G-75 column eluted with 20 mM HEPES, 135 mM NaCl, pH 6.5. Topotecan and phospholipid were quantified by spectrophotometry (Examples 70 and 71). The results (Table 13) indicated that Topotecan loading was nearly quantitative in the range of pH 5.5-6.5.

TABLE 13

Effect of loading buffer pH on the % of Topotecan encapsulation into the liposomes with entrapped TEA-Pn.

| Loading buffer pH | % encapsulation |
|---|---|
| 5.0 | 50.1 ± 2.1 |
| 5.5 | 97.2 ± 8.1 |
| 6.0 | 115.5 ± 15.0 |
| 6.5 | 102.1 ± 8.1 |

The effect of drug to lipid ratio (0.15-0.45 mg/mmol phospholipid) on the loading efficiency was also studied. The liposomes with entrapped TEA-Pn (0.5 M TEA, pH 5.8, osmolality 480 mmol/kg) were prepared as above, except the final extrusion step was ten times through two stacked 0.08 μm polycarbonate filters. The loading was at pH 6.5. The liposome size was 93.1±15.1 nm by QELS. The results (Table 14) showed that drug loading efficiency was over 85% over the whole range of drug/lipid ratios studied.

TABLE 14

Effect of drug/lipid ratio on the encapsulation efficiency of Topotecan into the liposomes containing TEA-Pn.

| Topotecan/phospholipid ratio, mg/mmol | | % encapsulation |
| --- | --- | --- |
| Input ratio | Output ratio (after loading) | (mean ± SE) |
| 168.2 | 166.9 ± 11.1 | 99.2 ± 6.6 |
| 224.4 | 232.5 ± 47.6 | 103.7 ± 21.2 |
| 280.3 | 253.5 ± 19.8 | 90.4 ± 7.0 |
| 336.4 | 298.3 ± 18.0 | 88.7 ± 5.3 |
| 392.5 | 361.2 ± 36.8 | 92.0 ± 9.4 |
| 448.5 | 394.9 ± 29.5 | 88.0 ± 6.6 |

Example 21

Topotecan Liposome Stability In Vitro in the Presence of Plasma

Liposomes (DSPC/Chol/PEG-DSPE, molar ratio 3:2:0.015) with entrapped 0.5 N TEA-Pn, pH 6.2, osmolality 413 mmol/kg, were prepared as described in Example 18. Liposomes with the size of 96.4±29.3 nm were produced by extrusion ten times through two stacked 100 nm pore size polycarbonate filters. For quantitation of the liposome lipid in plasma, [$^3$H]-CHE was included in the lipid solution at 0.5 μCi/μmol of DSPC. Topotecan was loaded at pH 6.0, 58° C. for 45 min at a drug/phospholipid ratio of 150 mg/mmol. The efficiency of loading was 148.48±10.26 μg Topotecan/μmol phospholipid (99.0±6.8%).

The liposomes were incubated with 50% human plasma in a multiwell microdialysis device (Spectra-Por MicroDialyzer 10-well, Spectrum, USA). Human donor plasma was diluted by the equal volume of HEPES-buffered saline (20 mM HEPES, 135 mM NaCl), pH 6.5, containing 0.02% sodium azide and charged into the lower reservoir of the dialyzer (32 mL). The wells (0.4 mL) were separated from the reservoir by a polycarbonate membrane with 30 nm pore size, to afford free passage of plasma proteins and small molecules but not the liposomes. The liposomes were mixed with calculated amounts of plasma and HEPES-buffered saline to achieve the concentration of 2.5 mM phospholipid and 50 vol. % of plasma. The device was incubated at 37° C., and the contents of the reservoir were stirred slowly. After 8 hours of incubation, the contents of the lower reservoir were changed for fresh 50% plasma. At the given time points (see below) 50-μL aliquots were withdrawn from the wells, and chromatographed on the columns containing 2.2-2.4 mL of Sepharose CL-2B, eluent HEPES-buffered saline to separate the liposomes from plasma proteins and free drug. The liposomes were collected in the void volume fractions. Topotecan was quantified by fluorometry using excitation at 384 nm and emission at 524 nm after solubilization of the plasma samples in 90% aqueous isopropanol-0.1 N HCl, and the lipid was quantified by scintillation counting of [$^3$H]-CHE (quenching corrected). The determined drug-to-lipid ratio at time was compared to the initial ratio prior to incubation to obtain the % of Topotecan that remained encapsulated at each time point. After 8 hours of incubation, the amount of drug remaining in the liposome was about 55% of its initial value (Table 15).

TABLE 15

In vitro release of Topotecan from the liposomes loaded by TEA-Pn gradient in 50% human plasma at 37° C.

| Incubation time, hours | % drug remaining encapsulated |
| --- | --- |
| 1 | 95.5 ± 5.4 |
| 4 | 76.8 ± 7.3 |
| 8 | 55.9 ± 4.1 |
| 24 | 55.4 ± 16.8 |

Example 22

Topotecan Liposomes with Entrapped TEA-Pn Gradient at Various Drug/Lipid Ratios: In Vivo Drug Retention and Circulation Longevity in Mice The liposomes (DSPC/Chol/PEG-DSPE at 3:2:0.015 molar ratio, containing [$^3$H]-CHE at 0.5 mCi/mmol DSPC) with encapsulated gradient-forming salt solution (0.5 N TEA-Pn, pH 6.2, osmolality 413 mmol/kg) were prepared as in Example 18 using extrusion 12 times through two stacked 100 nm pore size polycarbonate filters. The liposome size was 107.7±19.1 nm by QELS. The liposomes in 5 mM HEPES, 50 g/L Dextrose, pH 6.5 were mixed with the aqueous stock solution of Topotecan (20 mg/ml) at drug/phospholipid ratios in the range 130-360 μg/μmol, followed my incubating the mixture at 58° C. for 45 min, placing on ice for 15 min and removal of unencapsulated drug by Sephadex G-75 chromatography. Twelve-week old female FvB mice were injected with the liposomes via the tail vein at a dose of 5 mg Topotecan per kg body weight (approx. 0.2 mg Topotecan/animal) in triplicate. At indicated times, typically 8 hours or 24 hours post injection, the mice were anesthetized, exsanguinated, and the blood samples were assayed for the drug and the liposome lipid as in Example 8. The results are shown in Table 16. After 24 hours, about 6-32% of the initial drug load remained encapsulated. Higher loads of the drug (>200 mg/mmol phospholipid) resulted in longer drug retention.

TABLE 16

In vivo drug retention and circulation longevity of prototype Topotecan liposomes loaded using TEA-Pn gradient method to different drug/lipid ratios.

| Encapsulated drug/phospholipid ratio, mg/mmol | Lipid remaining in circulation, % injected dose | | Topotecan remaining encapsulated, % of initial load | |
|---|---|---|---|---|
| | After 8 hours | After 24 hours | After 8 hours | After 24 hours |
| 127.2 ± 10.9 | 36.1 ± 2.0 | 18.7 ± 8.1 | 51.7 ± 7.1 | 6.72 ± 2.5 |
| 207.2 ± 21.6 | 32.1 ± 5.2 | 9.84 ± 1.88 | 75.6 ± 13.0 | 13.8 ± 3.5 |
| 301.3 ± 24.5 | 34.4 ± 3.2 | 8.04 ± 4.25 | 79.2 ± 4.2 | 25.6 ± 4.4 |
| 360.3 ± 35.6 | 33.6 ± 2.4 | 8.68 ± 4.96 | 73.5 ± 7.0 | 32.3 ± 9.8 |

Example 23

In Vivo Drug Retention and Circulation Longevity of Topotecan Liposomes Loaded Using Different Entrapped Ammonium and Triethylammonium Salts The liposomes composed of DSPE, cholesterol, and PEG-DSPE (3:1:0.1 by weight), also containing [$^3$H]-CHE at 0.22 mCi/mmol DSPE, were prepared as in Example 18, except that the extrusion step included 10 passages through 2 stacked 200-nm pore filters, 10 passages through 2 stacked 100-nm pore filters, and 20 passages through 2 stacked 50-nm pore filters. The liposomes contained the following salt solutions:

0.5 N ammonium dextran sulfate solution (A-DS) was prepared from sodium dextran sulfate (M.w. 5000), purchased from Sigma, and converted into ammonium salt by the ion exchange procedure similar to that of Example 4. The solution of dextran sulfuric acid was immediately titrated with 12.4 M aqueous ammonia. The A-DS solution has pH 5.66, osmolality 208 mmol/kg.

0.48 N ammonium sucrose octasulfate (A-SOS) was prepared similar to Example 6, but ammonium hydroxide was used for titration. The solution had pH 6.27, osmolality 258 mmol/kg.

0.47 M triethylammonium sucrose octasulfate (TEA-SOS) was prepared as in Example 6. The solution has pH 6.6, osmolality 297 mmol/kg.

Topotecan was loaded into the liposomes in the aqueous solution of 10 mM MES-Na, 50 g/L dextrose, pH 6.5, by incubating the liposomes with the drug at 61-62° C. and input drug/phospholipid ratio of 346±1 mg/mmol, for 40 min, followed by incubating on ice for 10 min. The liposomes were purified from unencapsulated drug by chromatography on Sephadex G-25, eluent-aqueous 2 mM Histidine, 144 mM NaCl, pH 6.6 (HCl).

Seven to nine week old female Swiss Webster mice were injected via the tail vein with these liposomal Topotecan formulations at the dose of 5 mg Topotecan per kg body weight (approx. 0.2 mg Topotecan/animal) in triplicate. After 8 hours or 24 hours post injection the blood was collected and analyzed for Topotecan and liposome lipid as in Example 22.

The results are presented in Table 17 below. While all three liposome formulations demonstrated very close liposome circulation longevity, having about 23-28% of the injected dose remaining in blood 24 hours post injection, unexpectedly the drug retention in TEA-SOS liposomes and in A-SOS liposomes was better than in A-DS liposomes both in terms of magnitude (about 2-fold improvement in drug retention) and statistical significance (statistical significance at 95% confidence level by 2-tailed non-paired Student's t-test p=0.0257 and p=0.00995, respectively; and by Mann's U-test the difference was significant with α=0.01). Drug retention in TEA-SOS containing Topotecan liposomes was better than in A-SOS containing Topotecan liposomes.

TABLE 17

In vivo drug retention and circulation persistence of Topotecan liposomes prepared using TEA-SOS, ammonium-SOS (A-SOS), and ammonium dextran sulfate (A-DS.

| Gradient | Drug/phospholipid ratio, mg/mmol | Loading efficiency, % | Liposome size, nm | Lipid remaining in circulation, % injected dose | | Topotecan remaining encapsulated, % of initial load | |
|---|---|---|---|---|---|---|---|
| | | | | After 8 hours | After 24 hours | After 8 hours | After 24 hours |
| A-DS | 288.1 ± 20.6 | 83.3 ± 6.0 | 76.9 ± 22.7 | 43.7 ± 1.2 | 27.7 ± 1.5 | 43.6 ± 6.8 | 18.7 ± 1.5 |
| A-SOS | 346.2 ± 14.3 | 100.0 ± 4.1 | 99.7 ± 28.9 | 42.3 ± 2.2 | 23.4 ± 2.0 | 53.3 ± 0.8 | 31.3 ± 3.2 |
| TEA-SOS | 340.8 ± 14.7 | 98.5 ± 4.2 | 99.1 ± 32.6 | 42.1 ± 2.3 | 23.0 ± 2.9 | 57.0 ± 5.6 | 38.1 ± 6.1 |

Example 24

Drug and Lipid Plasma Pharmacokinetics of Liposomal Topotecan in Rats

The circulation longevity and Topotecan release parameters were assessed in rats. The liposomes (DSPC/Cholesterol/PEG-DSPE molar ratio 3:2:0.015) were prepared by ethanol mixing/extrusion method and loaded with Topotecan using TEA-Pn gradient or TEA-Sucrose octasulfate (TEA-SOS) gradient as described in Example 18 and loaded at various drug/lipid ratios (15-450 mg/mmol phospholipid). For lipid matrix quantification, the liposome lipid contained [3H]-CHE at 0.5-1.5 mCi/mmol DSPC. Female Sprague Dawley rats (6-8 week old; body weight about 200 g) with indwelling central venous catheters were injected i.v. (via the catheter) with the Topotecan liposomes at the dose of 4-5 mg/kg of body weight. The catheter was flushed with saline. At selected times (up to 48 hours post injection) the blood samples (0.2-0.3 mL) were drawn via the catheter into heparinized syringes, mixed with 0.4 mL of cold phosphate buffered saline with 0.04% EDTA, blood cells were separated by centrifugation, and the supernatants (PBS-diluted plasma) were assayed for lipid by $^3$H-CHE radioactivity counting (quenching corrected), and for Topotecan by fluorometry (Example 71). The assay results were corrected for plasma dilution, calculated from the weight of obtained blood sample and assuming a hematocryt of 40%. The total blood dose of the drug and lipid was estimated from the blood volume calculated as 6.5% of the body weight. The percent of Topotecan retained in the liposomes was calculated by comparing the drug/lipid ratio at a given time point to the drug/lipid ratio of the injected liposomes. Table 18 below summarizes blood half-lives of the lipid, the drug, and the half-lives for drug release, as well as other properties of the liposomes.

Figure 8A:
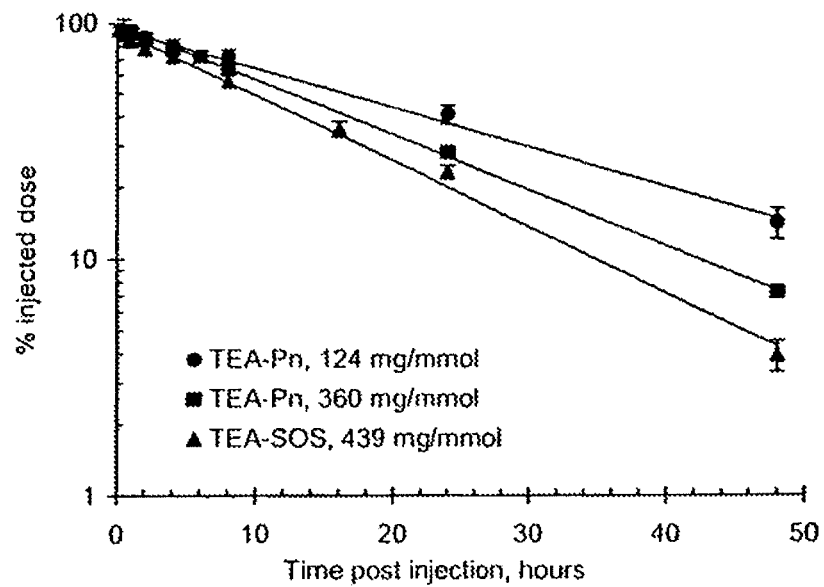
FIG. 8A shows blood pharmacokinetics of the liposome lipid after i.v. bolus administration of Topotecan-loaded liposomes to a rat. The on-panel caption indicates the drug loading method and the drug content of the liposomes. (See Example 24).
Figure 8B:
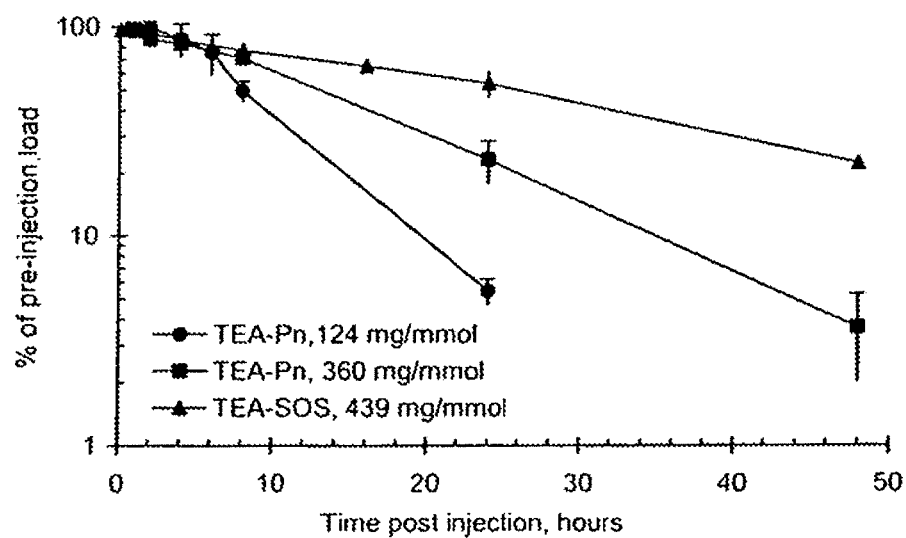
FIG. 8B shows the dynamics of drug-to-liposome lipid ratio in the blood of a rat in vivo following i.v. bolus administration of the liposomes loaded with Topotecan The on-panel caption indicates the drug loading method and the drug content of the liposomes. (See Example 24).

Pharmacokinetic (PK) curves are shown on FIGS. 8A (lipid) and 8B (drug/lipid ratio). In summary, the blood PK curves for both drug and lipid fit well to single exponent model ($R^2$ 0.984-0.999). Despite their 90-100 nm size and very small amount of PEGylated lipid (0.3 mol. %), the liposomes unexpectedly showed good circulation longevity (plasma half-lives of the lipid component were in the range of 11-16 hours). The slowest release of Topotecan (half-time 22.9 hours) was observed with the liposomes loaded using the TEA-SOS method.

TABLE 18

Circulation half-life ($t_{1/2}$) of lipid, drug, and half-time for drug release from the prototype Topotecan liposomes in rats.

| Entrapped salt, and concentration | Topotecan load, mg/mmol phospholipid | Liposome size, nm (mean ± SD) | Injected dose, mg/kg | $t_{1/2}$ lipid, hours | $t_{1/2}$ drug, hours | $t_{1/2}$ of drug release, hours | No. of animals per group |
|---|---|---|---|---|---|---|---|
| TEA-Pn 0.5N | 124.3 ± 9.7 | 92.3 ± 23.3 | 4 | 15.8 | 4.13 | 5.34 | 3 |
| TEA-Pn 0.5N | 360.3 ± 35.6 | 107.7 ± 19.1 | 5 | 12.8 | 6.06 | 9.97 | 2 |
| TEA-SOS 0.643N | 439.2 ± 15.9 | 108.8 ± 13.4 | 5 | 10.8 | 7.36 | 22.87 | 2 |

Example 25

Drug Stability Against Leakage During Storage of Topotecan Liposomes

The samples of several prototype formulations prepared for the above-described studies, were stored at 4-6° C. for various times to assess the storage stability of the encapsulated Topotecan against drug leakage from the liposomes. The liposome samples were passed through Sephadex G-75 columns, eluted with 20 mM HEPES, 135 mM NaCl, pH 6.5, to remove extraliposomal drug, and analyzed for drug content by spectrophotometry and for lipid by [3H]-CHE radioactivity counting. The results (Table 19) indicate good retention of Topotecan in the liposomes during storage.

TABLE 19

Drug retention in prototype Topotecan liposomes during storage.

| Liposome gradient-forming salt | Liposome size, mean ± SD, nm | Initial drug load, mg drug/mmol phospholipid | Storage time, months | Drug load after storage as % of initial |
|---|---|---|---|---|
| TEA-Pn 0.500N pH 6.2 | 96.4 ± 29.3 | 148.5 ± 10.3 | 8 | 101.6 ± 5.5 |
| TEA-Pn 0.500N pH 6.2 | 107.7 ± 19.1 | 127.2 ± 10.9 | 6 | 94.6 ± 6.2 |

TABLE 19-continued

Drug retention in prototype Topotecan liposomes during storage.

| Liposome gradient-forming salt | Liposome size, mean ± SD, nm | Initial drug load, mg drug/mmol phospholipid | Storage time, months | Drug load after storage as % of initial |
|---|---|---|---|---|
| TEA-Pn 0.500N pH 6.2 | 107.7 ± 19.1 | 207.2 ± 21.6 | 6 | 113.9 ± 9.4 |
| TEA-Pn 0.500N pH 6.2 | 107.7 ± 19.1 | 301.3 ± 24.5 | 6 | 112.9 ± 9.3 |
| TEA-SOS 0.643N pH 5.6 | 108.8 ± 13.4 | 439.2 ± 15.9 | 2 | 97.8 ± 9.4 |

Example 26

In Vitro Uptake of Liposomal and Immunoliposomal Topotecan by HER2-Overexpressing Cancer Cells This study addressed the capacity of Topotecan-loaded anti-HER2-immunoliposomes prepared according to the invention to deliver Topotecan specifically into HER2-overexpressing cells in cell culture. The (immuno)liposomes were prepared and loaded with Topotecan using TEA-Pn method of Example 19. HER-2 overexpressing human breast carcinoma cells (SKBr-3, ATCC) were grown in modified McCoy 5A medium (without tricine) supplemented with 10% fetal calf serum, 50 μg/mL streptomycin sulfate and 50 U/ml penicillin G (complete growth medium) in T-75 flasks at 37° C., 5% $CO_2$, to confluency. The cells were harvested by trypsinization, inoculated into 24-well cell culture plates at 150,000 cells/well in 0.5 mL of the complete growth medium, and allowed to acclimate overnight. The medium was replaced with 0.5 mL of complete growth medium containing Topotecan formulations at the selected concentration in the range of 0.01-0.1 mM phospholipid. Triplicate wells were used for each condition. Control wells were incubated in the absence of drug and/or liposomes (to obtain background readings for drug assay). The plates were incubated with slow agitation at 37° C., 5% $CO_2$ for 4-8 hours. The media were aspirated, and the cells were rinsed 4 times with 1 mL portions of cold Hanks' balance salt solution containing Ca and Mg salts. The cells were solubilized by adding 0.1 mL of 1% Triton X-100 in water, and the amount of drug in the cell lysates was determined by fluorometry (Example 71). The standard curve was obtained in the range of 10-2500 ng Topotecan/well, and fit to second order polynomial (to account for self-quenching at higher drug concentration) after subtracting the cell autofluorescence background. When a microplate fluorometer was used, the filter selection was 400/30 nm for excitation, 530/25 nm for emission. Both cuvette- and microplate fluorometers gave the same results.

The results of two experiments are summarized in Table 20 below. There was prominent cellular uptake of HER2-targeted liposomal drug (50-300 times higher than of no-targeted liposomal Topotecan). Interestingly, uptake of free Topotecan was also significantly lower than of HER2-targeted immunoliposomal Topotecan. This may be explained by rapid hydrolysis of the camptothecin lactone ring of Topotecan molecule in the cell growth medium in the presence of serum, generating the carboxylate form of the drug which may have lower cell permeability and lower cytotoxicity. In summary, the ability of cell-targeted, internalizable, ligand-conjugated immunoliposomes to deliver Topotecan intracellularly was confirmed.

TABLE 20

In vitro cellular uptake of Topotecan liposomes and anti-HER2 immunoliposomes containing TEA-Pn (nd, not determined). For liposome characteristics see Table 12.

| Liposome concentration, mM phospholipid | Topotecan concentration μg/mL | Exposure time, hours | Topotecan uptake by SK-Br-3 cells, ng/100,000 cells | | |
|---|---|---|---|---|---|
| | | | Non-targeted liposomes | F5-Immuno-liposomes | Free drug |
| 0.1 | 15.5 | 4 | 1.45 ± 0.09 | 163 ± 5.7 | nd |
| 0.01 | 1.55 | 4 | 0.185 ± 0.03 | 60.2 ± 2.0 | nd |
| 0.033 | 5.0 | 8 | 3.62 ± 2.03 | 169.6 ± 13.7 | 5.56 ± 0.91 |

Example 27

Cytotoxicity of Liposomal and Immunoliposomal Topotecan Against HER2-Overexpressing Cancer Cells In Vitro Once the capacity of anti-HER2 Topotecan immunoliposomes for intracellular drug delivery into HER2-overexpressing cancer cells was established (Example 26), it was important to ensure that the internalized liposomes can release the drug in its active form. To this end, in vitro cytotoxicity of the free Topotecan (i.e., Topotecan formulated as a solution), liposomal Topotecan, and anti-HER2-immunoliposomal Topotecan was studied. The liposomal Topotecan formulations were prepared, and SKBr-3 cells were grown and harvested as described in Example 26. The cells were inoculated into 96-well cell culture plates at 5,000 cells in 0.1 mL of the complete growth medium, in triplicate, and left to acclimate overnight. Edge-most rows and columns of the plate were left empty. Sterile preparations of Topotecan liposomes, immunoliposomes, or free drug (freshly prepared by diluting Topotecan 20 mg/mL stock, pH 3, into unbuffered saline to 2 mg/mL) were diluted with complete drug medium to achieve concentrations starting from 90, 30, or 10 μg/mL and serially diluted down in the medium by the factor of 3. The media in the wells were replaced with 0.2 mL of drug/liposome dilutions, and incubated at 37° C., 5% $CO_2$, for specified time (4-6 hours). One well in each row was incubated with drug-free medium to serve as a non-treated control. The drug-containing media were aspirated from the wells, the cells were rinsed with 0.2 mL of drug-free medium, and 0.2 mL of fresh drug-free medium was added to all wells. The plates were incubated for 4 days at 37° C., 5% $CO_2$. Without medium change, 0.03 mL of the 2 mg/mL solution of a tetrazolium dye (Thiazolyl Blue, MTT) (Sigma Chemical Co.) in serum-free medium was added to each well. The plates were incubated for additional 2-3 hours at 37° C., 5% $CO_2$. The media were aspirated, and the wells were filled with 0.2 mL of 70 vol. % aqueous isopropanol, 0.075 N HCl, and agitated gently until the formazan dye dissolves (15-30 min). The optical density of the formazan solutions was determined using microplate photometer at 540 nm. The cell viability as % of non-treated control was calculated as the ratio of the optical density in the experimental wells to the optical density in the wells containing non-treated cells, corrected for background. The data were plotted against the drug concentration, and the IC50 dose was estimated graphically from intersection of the viability-concentration curve with the 50% viability line.

Figure 9:
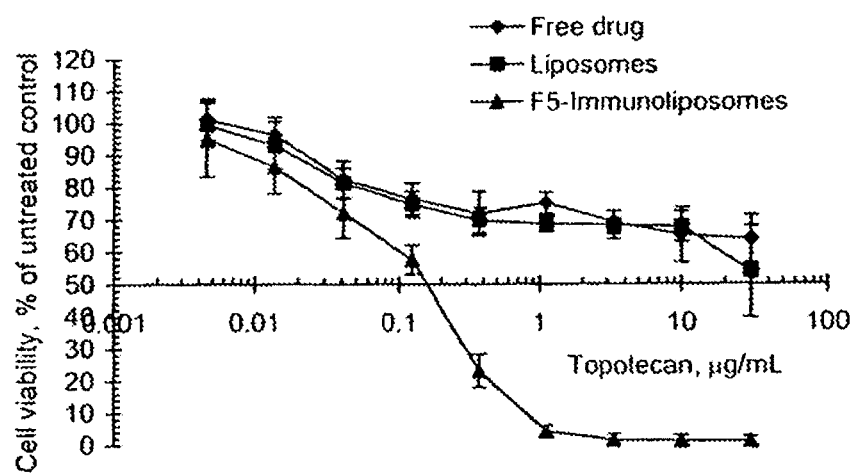
FIG. 9 shows the in vitro cytotoxicity of free, liposomal, or HER2-targeted immunoliposomal Topotecan (TEA-Pn method) against SKBr-3 breast carcinoma cells. (See Example 27).

The results are presented in FIG. 9. The drug dose resulting in 50% growth inhibition ($IC_{50}$) for free Topotecan or non-targeted liposomal Topotecan was in excess of 30 μg/mL; for F5-Immunoliposomal Topotecan, 0.15 μg/mL. These results are consistent with the targeted drug uptake data.

Example 28

Comparative Stability and Plasma Pharmacokinetics of Liposomal and F5-Immunoliposomal Topotecan in Mice Topotecan liposomes containing radioactive lipid label [$^3$H]-CHE at 1.5 mCi/mmol of phospholipid were prepared according to Examples 11 and 19 using an ethanol lipid solution mixing-extrusion procedure under the following conditions: gradient-forming salt solution: 0.643 N triethylammonium sucrose octasulfate; polycarbonate membrane extrusion: 15 passages through 2 stacked PCTE filters, 80 nm pore size; Topotecan loading: drug/phospholipid input ratio 350 mg/mmol (calculated for Topotecan free base); F5 scFv conjugation was performed as described in Example 19. The liposomes had the following characteristics:

Size by QELS: weight average 101.2 nm; standard deviation, 20.1 nm.

Drug encapsulation: Topotecan liposomes (Topo-Ls) 359.3±27.4 mg/mmol phospholipid; Topotecan F5scFv-immunoliposomes (Topo-F5-ILs) 326.3±15.9 mg/mmol phospholipid.

The study was performed generally as in Example 22. The groups of nine male Swiss Webster mice (8-10 week old, 24-27 g) were injected via tail vein with Topo-Ls, Topo-F5ILs, or freshly prepared Topotecan 1 mg/mL in unbuffered saline, at the dose of 5 mg Topotecan base per kg of the body weight (equivalent to the lipid dose of 14-16 μmol of phospholipid/kg body weight). At 1 hour, 8 hour, or 24 hour post injection time points, 3 animals per time point were exsanguinated via open heart punction under Ketamine/Xylazine anesthesia, the blood was collected into tubes containing PBS-EDTA, and assayed for Topotecan (fluorometry) and liposome lipid (by radioactivity scintillation counting). The amounts of drug and lipid dose remaining in the blood at given time points were calculated from the administered dose being taken as 100%, assuming the blood amount per animal as 6.3% of the body weight, and packed blood cell fraction of 45%. The amount of drug remaining encapsulated in the liposomes at each time point was calculated for each animal individually by comparing drug/lipid radioactivity ratio of the plasma samples with that of the injected liposomes. The amount of free Topotecan in the plasma samples collected at 1 hour post injection was less than 1% of the injected dose (indeed, they were below the detection limit of our assay method); therefore, further time points of the free Topotecan group were not studied. Because of the fast blood clearance and low blood levels of free Topotecan we assumed that essentially all Topotecan found in the blood at all time points represents liposomally encapsulated Topotecan.

The results are summarized in Table 21 below. Remarkably, the liposomes prepared according to the invention retained 79-85% of the original drug load even 24 hours after injection into the bloodstream of the animals. The differences between average plasma values of the lipid or drug between the liposome and immunoliposome groups were in the range of 1.8-13.6% and were close to, or within the range of, assay errors. Probabilities of the null hypothesis between the liposome and immunoliposome group with regard to drug or lipid values at each time point, calculated using Student's t-test, were in the range of 0.543-0.938. We conclude that the differences in residual blood levels of the drug or lipid between the two preparations were negligible and statistically indistinguishable.

TABLE 21

The amounts of liposome lipid, Topotecan, and of Topotecan remaining encapsulated in the liposomes in the plasma of mice at various time points post i.v. injection.

| Time post injection | Lipid, % of injected dose | Drug, % of injected dose | Drug/Lipid, % of pre-injection value |
|---|---|---|---|
| F5-conjugated liposomal Topotecan (Topo-F5ILs): | | | |
| 1 hour | 57.58 ± 4.95 | 55.45 ± 7.23 | 96.14 ± 7.32 |
| 8 hours | 35.37 ± 3.84 | 34.18 ± 5.87 | 96.31 ± 11.92 |
| 24 hours | 15.51 ± 11.84 | 12.30 ± 9.02 | 79.36 ± 8.03 |
| Liposomal Topotecan (unconjugated) (Topo-Ls): | | | |
| 1 hour | 58.88 ± 9.51 | 57.63 ± 9.45 | 97.90 ± 5.29 |
| 8 hours | 39.61 ± 1.99 | 38.82 ± 1.49 | 98.06 ± 4.44 |
| 24 hours | 15.84 ± 3.85 | 13.45 ± 2.64 | 85.25 ± 7.03 |

Example 29

Antitumor Efficacy of Liposomal and Anti-HER2-Immunoliposomal Topotecan in BT-474 Xenograft Model In this study we used the first prototype Topotecan immunoliposomes that use triethylammonium-polyphosphate gradient for drug entrapment. The liposomes were prepared generally following the methods of Examples 11 and 19. Lipid matrix components—DSPC (Avanti Polar Lipids; 3 mol. parts), Cholesterol (Calbiochem, 98.3%; 2 mol. parts) and methoxy-PEG(2000)-DSPE (Avanti Polar Lipids, 0.015 mol. parts)—were combined with 100% ethanol USP to give the solution containing 0.5 mM phospholipid at 60° C. The ethanol lipid solution was diluted at 60° C. with the aqueous triethylammonium polyphosphate solution (0.608 M triethylamine, 0.65 N phosphate, pH 6.1, osmolality 531 mmol/kg), mixed thoroughly, and extruded 10 times through 2 stacked polycarbonate membranes with the pore size of 100 nm (Nuclepore, Corning) using thermostatted gas-pressure extruder (Lipex Biomembranes) at 60° C. The extruded liposomes were chilled on ice, and unencapsulated triethylammonium polyphosphate was removed by gel chromatography on Sepharose CL-4B using 5% dextrose-5 mM HEPES-Na buffer, pH 6.5, as eluent. The liposome size was 103.8±35.1 nm by QELS. The liposomes in this buffer were incubated with Topotecan hydrochloride at 60° C. for 30 min. at the ratio of 0.35 mg Topotecan base per μmol of phospholipid. At the end of incubation, the liposomes were chilled on ice and chromatographed on Sephadex G-75, eluent 20 mM HEPES-Na, 135 mM NaCl, pH 6.5, to remove any unencapsulated drug. The drug content was determined by fluorometry, and the lipid content by phosphate assay as previously reported. Liposomal Topotecan so obtained has 365.4±23.1 mg Topotecan base per mmol of phospholipid. To prepare HER2-targeted Topotecan immunoliposomes, a portion of this liposomal Topotecan preparation was incubated with the purified conjugate of anti-HER2 scFv F5 and maleimido-PEG-DSPE linker generally as described in Example 19. Briefly, F5-PEG-DSPE conjugate in aqueous 10% sucrose-10 mM Na citrate solution, pH 6.5, was combined with Topotecan liposomes at the ratio of 15 mg protein per mmol of liposome phospholipid, and incubated at 60° C. for 30 min. The incubation mixture was chilled on ice and chromatographed on Sepharose CL-4B, eluent 20 mM HEPES-Na, 135 mM NaCl, pH 6.5, to remove any unincorporated scFv conjugate. The drug-to-lipid ratio decreased by 14% following this additional incubation.

The Topotecan liposome and immunoliposome formulations containing 1-2 mg/mL of Topotecan were passed through 0.2 micron sterile syringe filter, dispensed aseptically into polypropylene vials and stored at 4-6° C. for up to 1 month before use.

Free Topotecan was freshly prepared by dissolving Topotecan Hydrochloride powder at 2 mg/mL in 5% dextrose and sterilized by passage through 0.2-micron syringe filter.

A HER2-overexpressing BT-474 human breast adenocarcinoma xenograft model was established as described in Example 10. At day 13 post tumor inoculation, the animals having tumors in the range of 120-350 cubic mm were selected and randomized into 3 treatment and 1 control group of 12 animals each. At days 14, 18, and 21 post tumor inoculation the mice were treated with i.v. (tail vein) injections of Topotecan formulations at the per injection dose of 5 mg/kg body weight, or with equal volume of physiological saline. General health of the animals was monitored daily. Tumor sizes and body weights were monitored twice weekly for up to day 53 post tumor inoculation. The animals whose tumors reached 20% of the body weight, or those with progressive weight loss reaching 20% or more were euthanized.

Figure 11:
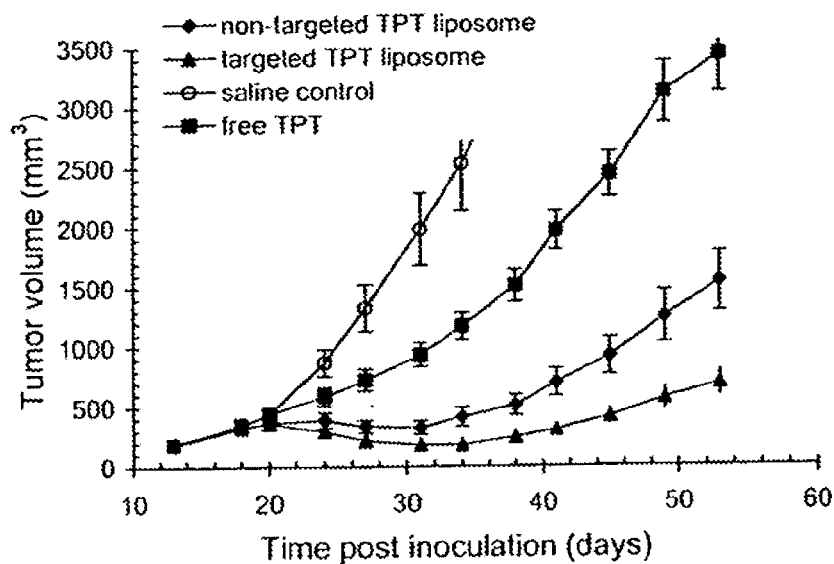
FIG. 11 shows antitumor efficacy of various Topotecan (TPT) formulations against BT-474 human breast cancer xenografts in nude mice. "Saline control" designates the mice treated with drug- and liposome-free vehicle only. (See Example 29).
Figure 12:
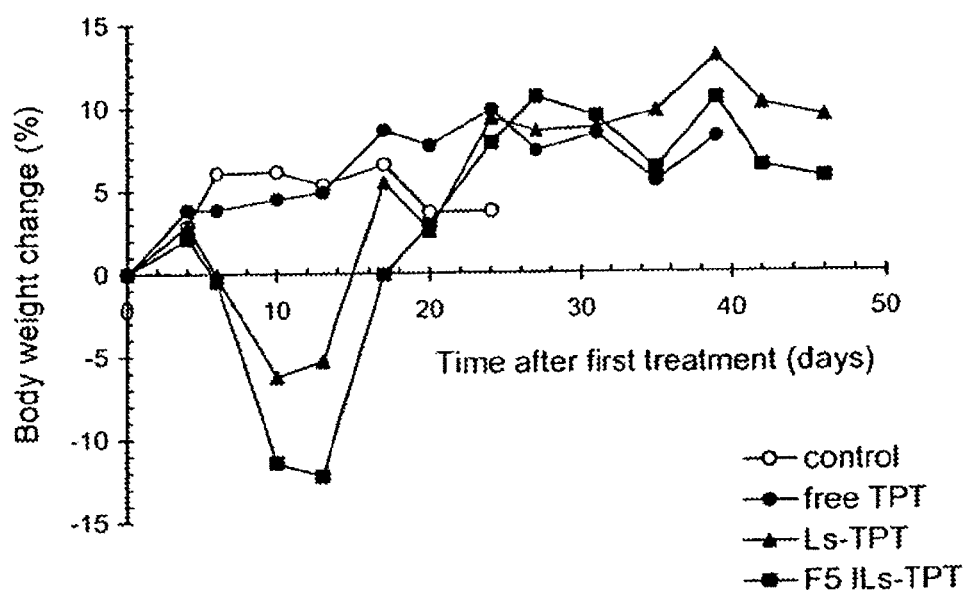
FIG. 12 shows the dynamics of the animals' body weights during the treatment of BT-474 tumor-bearing nude mice with free Topotecan (TPT), liposomal Topotecan (Ls-TPT), or anti-HER2 immunoliposomal Topotecan (F5 ILs-TPT). "Control" designates the mice treated with drug- and liposome-free vehicle only. (See Example 29).
Figure 13A:
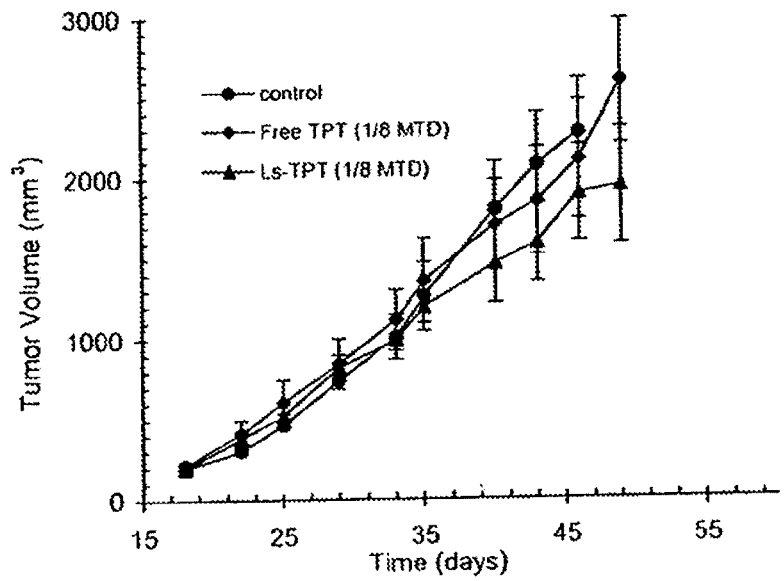
FIG. 13A shows antitumor efficacy of Topotecan formulations against BT-474 human breast cancer xenografts in nude mice. Free Topotecan (Free TPT) or liposomal Topotecan (Ls-TPT) were administered at one-eighth of their maximum tolerated doses. Error bars represent standard deviation of the data. "Control" designates the mice treated with drug- and liposome-free vehicle only. (See Example 31).
Figure 13B:
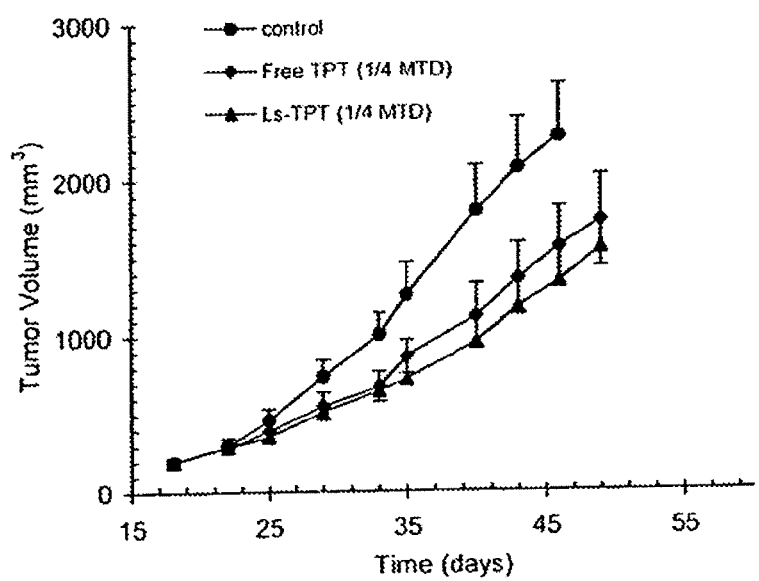
FIG. 13B shows antitumor efficacy of Topotecan formulations against BT-474 human breast cancer xenografts in nude mice. Free Topotecan (Free TPT) or liposomal Topotecan (Ls-TPT) were administered at one-fourth of their maximum tolerated doses. Error bars represent standard deviation of the data. "Control" designates the mice treated with drug- and liposome-free vehicle only. (See Example 31).
Figure 13C:
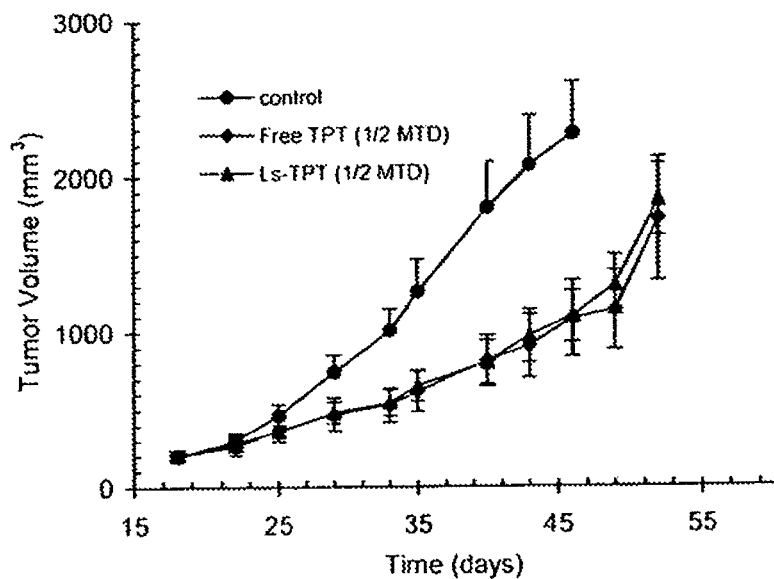
FIG. 13C shows antitumor efficacy of Topotecan formulations against BT-474 human breast cancer xenografts in nude mice. Free Topotecan (Free TPT) or liposomal Topotecan (Ls-TPT) were administered at one-half of their maximum tolerated doses. Error bars represent standard deviation of the data. "Control" designates the mice treated with drug- and liposome-free vehicle only. (See Example 31).
Figure 13D:
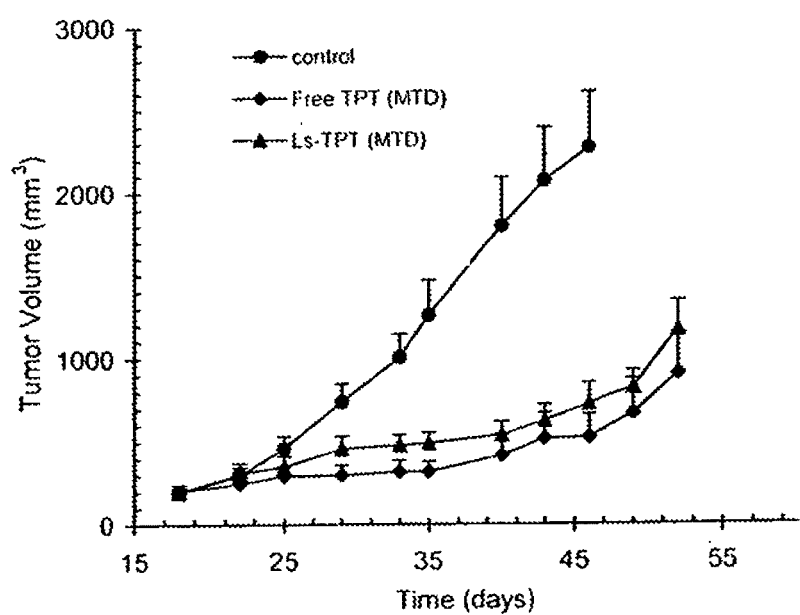
FIG. 13D shows antitumor efficacy of Topotecan formulations against BT-474 human breast cancer xenografts in nude mice. Free Topotecan (Free TPT) or liposomal Topotecan (Ls-TPT) were administered at their maximum tolerated doses. Error bars represent standard deviation of the data. "Control" designates the mice treated with drug- and liposome-free vehicle only. (See Example 31).

FIGS. 11 and 12 show the tumor growth and animal body weight data, respectively. Liposomal Topotecan formulations were more active in tumor growth suppression than the free drug, and F5-targeted liposomal formulation was more active than the non-targeted one. The average tumor sizes at the end of the observation period were significantly different among the treatment groups (p values by non-paired 2-tailed Student's t-test were $1.2 \times 10^{-6}$ for free v. immunoliposomal drug, 0.000114 for free v. liposomal drug, and 0.00718 for liposomal v. immunoliposomal drug). Thus, liposomally encapsulated Topotecan was more active than the free drug, and anti-HER2 immunoliposomal Topotecan was more active than non-targeted liposomal drug. In the liposomal and immunoliposomal group, after initial regression, tumor regrowth occurred within 10 days of the last treatment. There was no tumor regression in the free drug group. It was noticed that the liposomal formulations of Topotecan at a given dose were more toxic than the free drug. There was gastrointestinal toxicity. The animals receiving liposomal Topotecan developed diarrhea and suffered body weight loss averaging about 14% at its peak. While in the non-targeted liposomal group the animals recovered, except one (12.5%) that had persistent 15% weight loss at the end of study, in the F5-targeted group five animals (41.6%) developed terminal morbidity and expired; and two more (16.7%) had persistent weight loss of about 15%. In the control group and free drug group, there was no weight loss or treatment-related morbidity.

Example 30

Maximum Tolerated Dose (MTD) of Free and Liposomal Topotecan in Mice Given in 3 Weekly i.v. Injections This study used a liposome Topotecan formulation prepared as in to Example 29, except the triethylammonium polyphosphate solution was replaced with triethylammonium sucrose octasulfate solution having 0.65 M triethylammonium, pH 6.2; and for extrusion 80-nm polycarbonate membrane filters were used instead of 100-nm. Volume-weighted liposome size determined by quasi-elastic light scattering method in Gaussian approximation (QELS) was 95.1±19.6 nm (average±SD); drug/lipid ratio was 369.1±18.3 mg/mmol phospholipid. Five-six week old female Swiss-Webster mice (18-20 g) in the groups of two received three i.v. (tail vein) injections of free or liposomal Topotecan on a once-a-week schedule, starting from the dose of 2 mg/kg Topotecan base per injection and increasing to each subsequent group by the factor of 1.8 to the dose of 37.8 mg/kg. Immunoliposomal Topotecan was not included in this study. Animal body weight and general health was monitored daily. Progressive weight loss of more than 20% or natural death at any time in any of two animals in a group during the period of ten days since the beginning of treatment were considered indicative of the toxic dose. According to the animal mortality and weight data MTD was determined to fall within the range of 11.7-21 mg/kg for free Topotecan, and 2.0-3.6 mg/kg for liposomal (Prototype 2) Topotecan. In the second study, the mice received injections of the free, liposomal, or F5-immunoliposomal Topotecan (prepared from the liposomal Topotecan of this Example as described in Example 29) with the doses from 2.0 mg/kg (liposomal/immunoliposomal Topotecan) or 12 mg/kg (free Topotecan), and increased to each subsequent group by the factor of 1.15 until the dose next to the upper range of the established MTD interval was achieved. The highest dose that did not result in death or terminal morbidity in any of the animals was considered an MTD and was found to be 18.4 mg/kg for free Topotecan, 3.0 mg/kg for liposomal Topotecan, and 3.0 mg/kg for immunoliposomal Topotecan. Thus, liposomal Topotecan showed greater toxicity than the free drug.

Example 31

Figure 14:
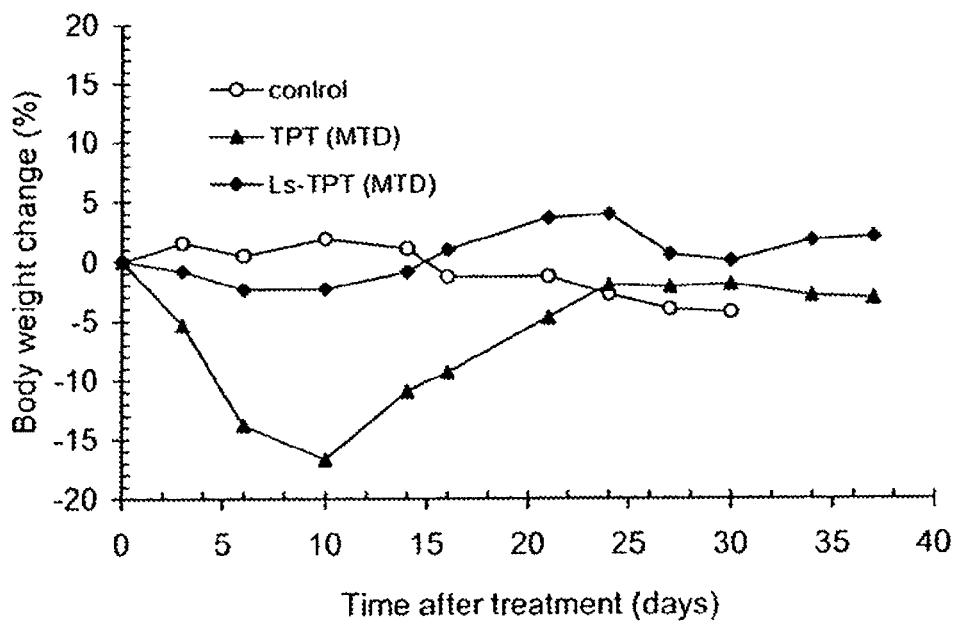
FIG. 14 shows the dynamics of the average body weights during the treatment of BT-474 tumor-bearing nude mice with free Topotecan (Free TPT) or liposomal Topotecan (Ls-TPT) administered at their maximum tolerated doses. "Control" designates the mice treated with drug- and liposome-free vehicle only. (See Example 31).

Antitumor Efficacy of Liposomal Topotecan in BT-474 Xenograft Model at the Range of 0.125-1.0×MTD The Topotecan liposomes and F5-immunoliposomes of Example 30 were used in this study. BT-474 subcutaneous xenografts were raised in nude mice as in Example 29. At day 18 after tumor cell inoculation the animals with tumors (105-345 cubic mm, average about 200 cubic mm) were randomized into treatment groups of 6 animals/group, and a control group of 8 animals/group. The animals received free or liposomal Topotecan at 1×MTD, 0.5×MTD, 0.25×MTD, or 0.125×MTD at three i.v. (tail vein) injections at day 19, 23, and 27 post tumor inoculation. The control group received injections of physiological saline. The tumor sizes and animal body weights were monitored as in Example 29. To obtain animal body weight measurements, the tumor weight (calculated from the tumor size assuming tumor density of 1.0) was subtracted from the total animal weight measurements. All drug formulations at MTD showed antitumor activity (FIGS. 13A-13D). There was no significant difference in efficacy between free and liposomal drug given at their respective MTD or at identical fractions (½, ¼, or ⅛) thereof. Thus, liposome encapsulation of the drug using TEA-SOS gradient resulted in about 6-fold increase in antitumor activity, but also in the similar increase in drug toxicity. Dynamics of animal body weights revealed that all treatments were non-toxic except the treatment with free Topotecan at MTD which showed transient decrease in body weight (about 15% of the pre-treatment value) that later resolved (FIG. 14).

Example 32

Preparation and Targeted In Vitro Cytotoxicity of Topotecan Liposomes Prepared Using Triethylammonium Sucrooctasulfate Entrapment Method Liposomal Topotecan was prepared generally following the procedure of Example 18, using the entrapped solution of TEA-SOS having 643 mM TEA, pH 5.7, osmolality 530 mmol/kg, and drug/phospholipid ratio of 170 mg/mmol. The liposomes had 155 mg drug/mmol phospholipid; 90% loading efficiency, and particle size 105 nm. These liposomes were incubated with the micellar solution of F5-PEG-DSPE conjugate at about 30 scFv per liposomes (15 mg antibody/mmol phospholipid) at 60° C. for 1 hour generally as described in Example 19. Antibody-conjugated liposomes were separated by SEC using Sepharose CL-4B and formulated into HBS-6.5 HEPES-buffered saline. There was no detectable change in drug/lipid ratio during the attachment of anti-HER2 scFv (F5).

The uptake of Topotecan formulations by cancer cells was determined as follows. HER2-overexpressing human breast adenocarcinoma cells (SK-Br-3, ATCC HTB-30) were plated into 24-well cell culture plates at 150,000 cells/well and acclimated overnight. The cells were incubated (in triplicate) with F5-targeted and non-targeted liposomal Topotecan in complete growth medium at liposome concentrations of 0.1 mM and 0.01 mM for 4 hours at 37° C. The cells were rinsed 4 times with Hanks' Balanced Salt Solution, solubilized in 0.1% Triton X-100-70% acidified isopropanol mixture 1:10, and the amount of cell-associated Topotecan per well was determined by fluorometry. The results (mean±standard error) are summarized in Table 22. The targeted liposomes delivered 100-300 times more drug into the targeted cells than nontargeted liposomes.

TABLE 22

Uptake of liposomal Topotecan by SK-Br-3 breast carcinoma cells.

| Formulation | Topotecan uptake at 0.1 mM phospholipid, ng/well | Topotecan uptake at 0.01 mM phospholipid, ng/well |
|---|---|---|
| Non-targeted liposome | 4.76 ± 0.24 | 0.607 ± 0.088 |
| HER2-targeted liposome | 533.8 ± 13.7 | 197.0 ± 4.6 |
| Ratio: Targeted/Non-targeted | 112.1 ± 8.6 | 324 ± 55 |

Figure 10:
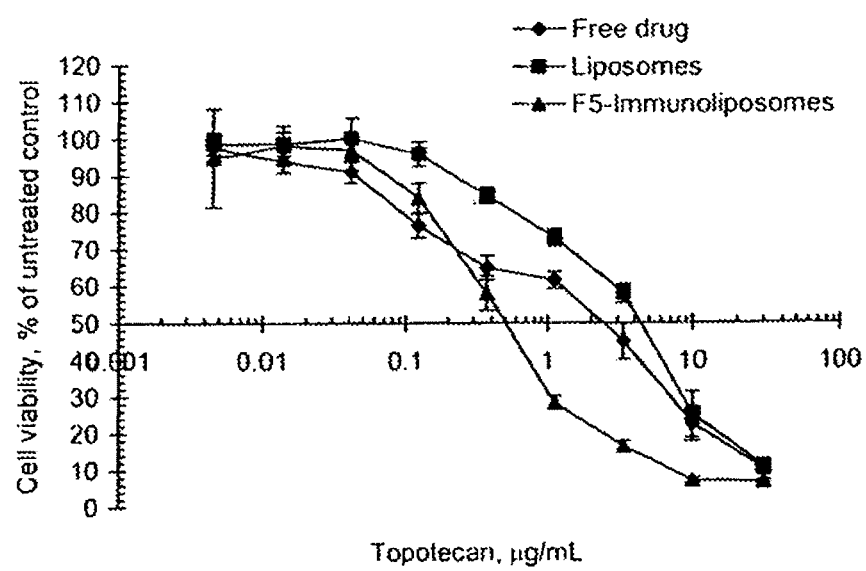
FIG. 10 shows the in vitro cytotoxicity of free, liposomal, or HER2-targeted immunoliposomal Topotecan (TEA-SOS method) against SKBr-3 breast carcinoma cells. (See Example 32).

Cytotoxicity of these Topotecan formulations against SKBr-3 breast cancer cells was determined as described in Example 27. SKBr-3 cells were inoculated into 96-well plates at 5,000 cells/well, acclimated overnight, and incubated with increasing concentrations (0.004-30 µg/mL) of free, liposomal, or F5-immunoliposomal Topotecan in cell growth medium for 4 hours at 37° C. The drug-containing media were removed and the cells were allowed to grow in the drug-free medium for 72 hours. The quantity of viable cells per well was determined using Thiazolyl Blue (MTT) tetrazolium assay and expressed as % of that of control (non-treated) cells. The results are presented on FIG. 10. Topotecan immunoliposomes were more cytotoxic ($IC_{50}$ 0.15-0.5 µg/mL) than non-targeted Topotecan liposomes ($IC_{50} \geq 3.1$ µg/mL) and free Topotecan ($IC_{50} \geq 2.3$ µg/mL)

Example 33

In Vivo Stability of Topotecan Liposomes of Different Size

The liposomes containing TEA-Pn were prepared as in Example 22 using extrusion 12 times through 100 nm pore size polycarbonate membranes or additionally 12 times through 50 nm pore size polycarbonate membranes. Topotecan (TPT) was added at a ratio of 150 phospholipid. The loading was completed at 58° C. for 45 min a hot water bath, followed by quenching on ice. The efficiency of loading for the 50-nm- and 100-nm-extruded liposome was 126.80±19.24 µg TPT/µmol PL (84.5±12.8%) and 148.48±10.26 µg TPT/µmol PL (99.0±6.8%), respectively. Female Swiss Webster mice in the groups of three were injected intravenously with one of the two formulations of Ls-TPT at a dose of 5 mg TPT/kg. The mice were sacrificed after 6 h and the blood was collected. Plasma was analyzed for TPT and liposome lipid as described in Example 22. The results are presented in Table 23.

TABLE 23

In vivo stability of Ls-TPT of different sizes loaded using TEA-Pn entrapment method.

| Liposome size, nm | Drug in plasma, % of injected dose | Liposome lipid in plasma, % of injected dose | Drug/lipid ratio, % of pre-injection value |
|---|---|---|---|
| 74.2 ± 21.6 | 32.93 ± 1.97 | 45.7 ± 2.2 | 72.06 ± 5.51 |
| 96.4 ± 29.3 | 33.26 ± 3.56 | 37.6 ± 5.3 | 88.41 ± 15.68 |

Example 34

Synthesis and Liposome Encapsulation of 6-(3-Aminopropyl) Ellipticine (6-APE)

6-(3-aminopropyl)ellipticine was prepared from ellipticine in a two-step method based on the procedure by Werbel et al., *J. Med. Chem.* 1986, v. 29, p. 1321-1322. 501.4 mg of ellipticine base (NSC 71795) (Aldrich Chemical Co.) was stirred with approximately 100 mg of sodium hydride (Sigma; washed with anhydrous petroleum ether) in 5 ml of dry dimethylformamide (DMF) at room temperature for 30 min. To this mixture, a solution of 678 mg of N-bromopropylphtalimide (Aldrich) in 2 mL of dry DMF was added dropwise. The purple-colored reaction mixture was stirred under argon overnight, treated with 1 mL of water, and poured into 60 ml of water. The mixture was extracted twice with 25 mL of methylene chloride, the extract was dried over anhydrous sodium sulfate, and passed through a layer of neutral alumina. The alumina layer was rinsed twice with 10 mL of methylene chloride and the combined filtrate and rinses were brought to dryness in vacuum. The product was stirred overnight with 20 ml of absolute ethanol and 2 ml of anhydrous hydrazine at room temperature. The obtained slurry was filtered under vacuum, a yellow filtrate was diluted with 50 mL of 0.2 N NaOH and extracted with two portions (75 ml and 50 ml) of chloroform. The chloroform extract was dried over $Na_2SO_4$ and brought to dryness in vacuum. Crude product (yield 408 mg) was chromatographed on silica 60 column eluted isocratically with chloroform-methanol mixture (7:3 by volume), saturated with dry trimethylamine. The fractions eluted in a second yellow-colored band, following un-reacted ellipticine, were shown to contain the desired compound in approximately 30% yield. The structure was confirmed by $^1$H-NMR. TLC: $R_f$ 0.29-0.31 (Silica 60; $CHCl_3$-MeOH 7:3 by volume, saturated with trimethylamine). Ellipticine, $R_f$ 0.81-0.83. The obtained compound was converted into dihydrochloride salt by dissolving in anhydrous ethanol and titration with 6 N HCl solution in dry isopropanol. The orange crystals of 6-APE dihydrochloride (NSC 176328) were filtered out, rinsed with ether, and dried in vacuum. Yield of dihydrochloride 86%.

The liposomes were prepared by hydration of the neat lipid film of DSPC, Cholesterol, and PEG(M.w. 2,000)-DSPE (3:2:0.015 molar ratio) in a solution of trimethylammonium polyphosphate (TMA-Pn) at 0.5 M TMA, pH 5.6, at 60° C., followed by six cycles of rapid freezing (−78° C.) and thawing (60° C.), and extrusion ten times through two stacked 50-nm pore size polycarbonate filters. Unencapsulated TMA-Pn was removed using a Sepharose CL-4B column eluted with HEPES-Dextrose (5 mM HEPES, 5% Dextrose, pH 5.5). The liposome size was 85.7±32.1 nm.

Concentrated 6-APE solution (10 mg/ml) was added to the TMA-Pn-containing liposomes at a drug-to-phospholipid ratio of 100 µg APE/µmol phospholipid, the mixture was incubated at 58° C. for 45 min, and quickly cooled down on ice for 15 min. Unencapsulated drug was removed by gel chromatography on a Sephadex G-75 column eluted with HEPES-Dextrose buffer (5 mM HEPES-Na, 5% dextrose, pH 6.5). Liposome-entrapped APE was then quantitated by spectrophotometry as in Example 71, and liposome phospholipid was determined using the extraction assay of Example 70. The drug encapsulation was practically quantitative.

Example 35

Figure 15:
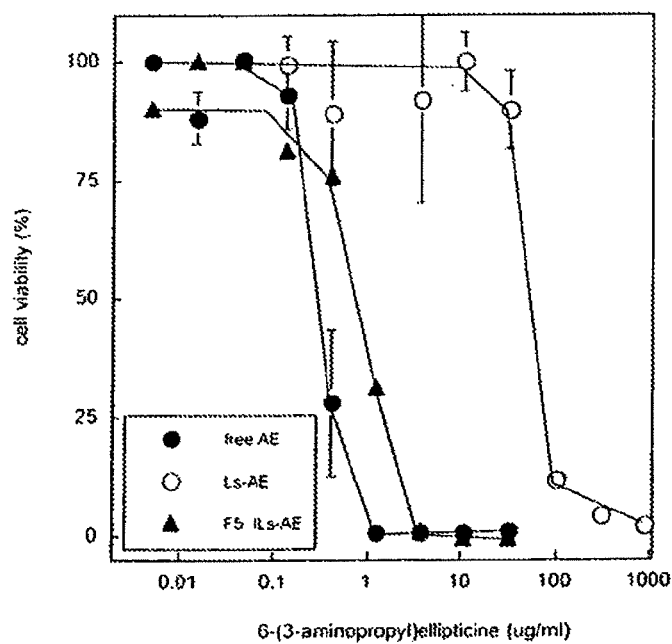
FIG. 15 shows the cytotoxicity of free 6-(3-aminopropyl)-ellipticine (Free AE), liposomal 6-(3-aminopropyl)-ellipticine (Ls-AE), or HER2-targeted immunoliposomal 6-(3-aminopropyl)-ellipticine (F5 ILs-AE) against BT-474 breast carcinoma cells in vitro. (See Example 35).

Preparation of HER2-Targeted Immunoliposomal 6-APE and Cytotoxicity of 6-APE Formulations Against HER2-Overexpressing BT-474 Breast Cancer Cells In Vitro Liposomes with encapsulated 6-APE (Ls-APE) were prepared as in Example 34 above. Anti-HER2 immunoliposomes with encapsulated 6-APE (F5-ILs-APE) were prepared from Ls-APE by the method of Example 19. An MTT-based cell viability assay of Example 27 was used to determine the cytotoxicity of 6-APE delivered as a solution, Ls-APE, or as HER2-targeted F5-ILs-APE against HER2-overexpressing human breast carcinoma cells (BT-474). The cells were exposed to drug-containing media for 6 hours, and post-incubated in drug-free medium for 3 days. The results are shown on FIG. 15. The $IC_{50}$ for free APE is 0.26 APE/ml, for F5-ILs-APE was 0.756 µg APE/ml, and for nontargeted Ls-APE was 51.0 APE/ml. There was a 67.5 fold difference in activity between targeted and nontargeted liposomal 6-APE, indicating a considerable targeted delivery effect.

Example 36

EGFR-Targeted Immunoliposomal Formulations of 6-APE and Cytotoxicity Against Cancer Cells In Vitro 6-APE-loaded liposomes were prepared as described in Example 34. EGFR-targeted immunoliposomes were prepared by attachment of EGFR-specific Fab' antibody fragments as follows. An EGFR-specific IgG MAb C225 (cetuximab, ERBITUX™, Imclone Systems) was digested with pepsin to produce (Fab')$_2$ fragments. Purified (Fab')$_2$ fragments were reduced by treatment with 10-20 mM 2-mercaptoethylamine for 15 min at 37° C., and Fab' fragments were purified by gel filtration using Sephadex G-25. The presence of reactive thiol groups was typically about 0.9 thiol groups per protein molecule (quantified using Ellmann's reagent). C225Fab' were covalently conjugated to an amphiphilic linker Mal-PEG-DSPE (Avanti Polar Lipids, AL) in aqueous solution at pH 6.2-6.5 and protein-linker molar ratio of 1:4 for 2-4 hours at room temperature, or overnight at 4-6° C., to produce C225Fab'-PEG-DSPE conjugate with the yield 30-50% of the protein. This micelle-forming conjugate was separated from non-reacted protein by size exclusion column chromatography on 3% agarose—4% polyacrylamide beaded gel (Ultrogel AcA34, obtained from Sigma Chemical Co.), eluted with HBS-6.5 buffer. The conjugate was recovered in void volume fractions. Immunoliposomal 6-APE was formed by incubating these liposomes with C225 Fab'-PEG-DSPE with drug-loaded liposomes at the ratio of 30 mg C225 protein/mmol liposome phospholipid for 30 min at 60° C., quenching on ice for 15 min, and purifying the immunoliposomes by gel chromatography on a Sepharose CL-4B column also eluted with HBS-6.5 buffer (the liposomes appear in or near the void volume of the column).

Figure 16:
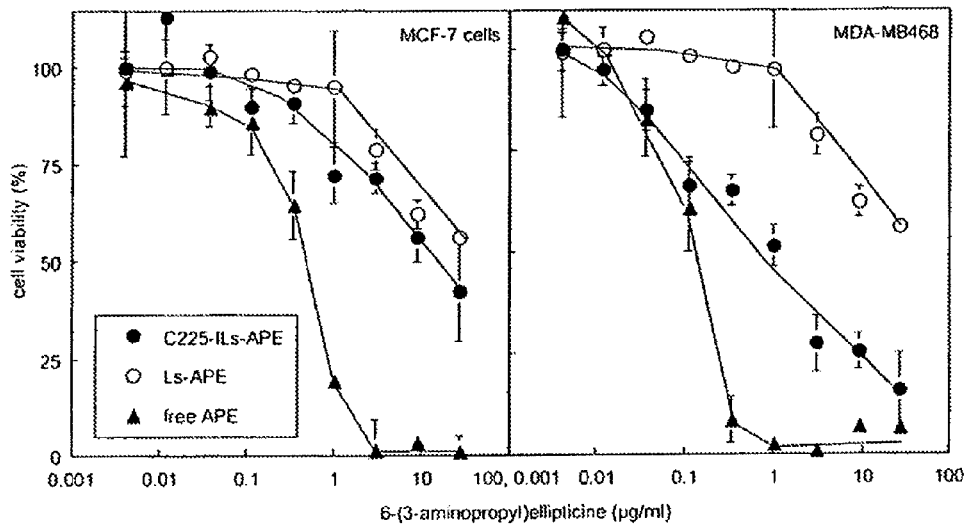
FIG. 16 shows the in vitro cytotoxicity of free 6-(3-aminopropyl)-ellipticine (Free APE), liposomal 6-(3-aminopropyl)-ellipticine (Ls-APE), or EGFR-targeted immunoliposomal 6-(3-aminopropyl)-ellipticine (C225-ILs-APE) against breast carcinoma cells with low (MCF-7) or high (MDA-MB468) expression of EGF receptor. (See Example 36).

MDA-MB-468 EGFR-overexpressing human breast cancer cells and MCF-7 human breast cancer cells with low EGFR expression (ATCC, Rockville, Md.) were cultured in their supplier-recommended growth media, and the cytotoxicity of free, liposomal, and anti-EGFR-immunoliposomal 6-APE against these cells was studied according to the method of Example 27 The cells were incubated with drug-containing media for 6 hours, followed by 3 days post-incubation in the drug-free medium. The results are shown in FIG. 16. In MDA-MB-468 cells $IC_{50}$ for the free 6-APE was about 0.1 µg/ml, and for C225-ILs-APE about 0.9 µg/ml. In MCF-7 cells $IC_{50}$ was about 0.1 for the free 6-APE was about 0.5 µg/ml, and for C225-ILs-APE about 14 µg/ml. $IC_{50}$ of Ls-APE in both cell lines was >30 µg/ml. Thus, EGFR-targeted G-APE-loaded immunoliposomes demonstrated antigen-specific cytotoxic activity in EGFR-overexpressing MDA-MB-468 breast cancer cells, but not in MCF-7 breast cancer cell that do not overexpress EGFR. In MCF-7 cells, the targeted and nontargeted 6-APE liposomes were equally active.

Example 37

Pharmacokinetics of Liposomal 6-APE in Rats

Liposomes with entrapped TEA-Pn solution (557 mM phosphate groups, 500 mM TEA, pH 5.8, osmolality 480 mmol/kg) and lipid composition of DSPC, cholesterol, and PEG-DSPE (molar ratio 3:2:0.015) were prepared as in Example 11 above. Ethanolic solution of the lipids was combined at 60° C. with 10 volumes of the aqueous TEA-Pn solution, and extruded ten times through two stacked 80 nm pore size polycarbonate membranes. Unencapsulated TEA-Pn was removed using a Sepharose CL-4B column eluted with MES-Dextrose (5 mM MES-Na, 5% Dextrose, pH 5.5). The liposome size was 92.3±23.3 nm by QELS. A non-exchangeable radioactive lipid label [$^3$H]-CHE was included in the lipid matrix at 0.5 mCi/mmol phospholipid. The liposomes were loaded with 6-APE as described in Example 34.

The pharmacokinetic study followed the protocol of Example 9. Female Sim Albino rats (9 weeks, 200 g) were injected i.v. at a dose of 10 mg 6-APE/kg. Blood was drawn at prescribed time points and the plasma was analyzed for 6-APE by fluorometry. Plasma aliquots (0.05-0.2 ml) were mixed with 1-2 mL of 90% aqueous isopropanol-0.1 N HCl, and the 6-APE was quantified by fluorescence as in Example 71. The lipid was quantified by [$^3$H]-CHE radioactivity scintillation counting.

Figure 17:
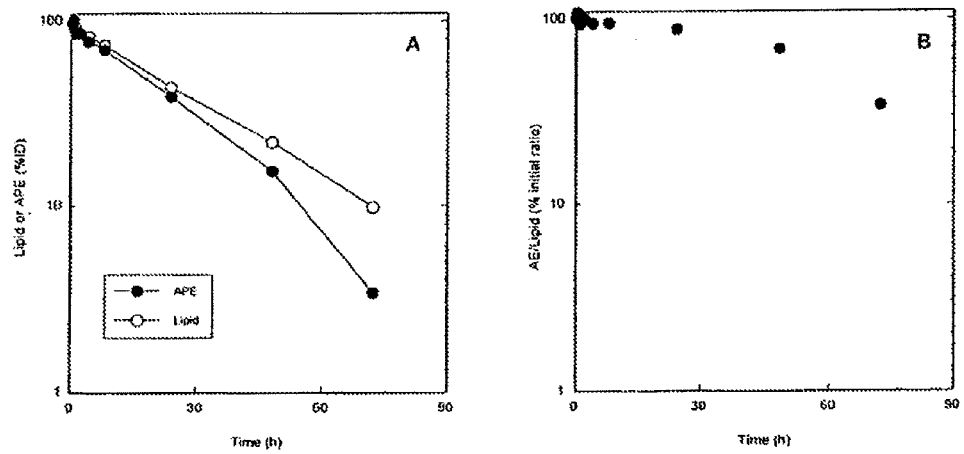
FIG. 17 shows blood pharmacokinetic attributes of the liposomally formulated 6-(3-aminopropyl)ellipticine (APE): blood pharmacokinetics of the liposome lipid (Panel A, open circles), the drug (Panel A, filled circles), and the dynamics of drug-to-liposome lipid ratio (Panel B) after i.v. bolus administration of APE liposomes to a rat. (See Example 37).

The results are shown in FIG. 17. The blood half-life ($t_{1/2}$) of the drug was 13.7 hours and of the liposome lipid 16.6 hours (panel A). The half-life of the drug release from liposomes was 77.9 hours, demonstrating remarkable encapsulation stability (panel B).

Example 38

Synthesis and Liposomal Encapsulation of 2-(2-(N,N-Diethylamino)Ethyl)Ellipticinium (2-DAE)

2-(2-(N,N-diethylamino)ethyl-ellipticinium chloride (NSC 359449) is an anti-cancer ellipticine derivative which is prepared by alkylation of ellipticine with 2-(N,N-diethylamino)ethylchloride in methanol in the presence of triethylamine (see Werbel, L. M., Angelo, M., Fry, D. M., and Worth, D. F. *J. Med. Chem*. 1986, 29:1321-1322). Liposomes containing entrapped TEA-Pn were prepared as described in Example 37. 2-DAE.2HCl was incubated with the TEA-Pn liposomes in 5 mM HEPES-Na, 5% Dextrose, pH 7.4, at a 2-DAE-to-phospholipid ratio of 100 µg/µmol. The amount of loaded drug was 88.2 µg APE/µmol PL (efficiency 88.2%).

Example 39

Pharmacokinetics of Liposomal 2-DAE in Rats

Blood pharmacokinetics of liposomal 2-DAE (Example 38) was studied in rats as in Example 37. The $t_{1/2}$ of 2-DAE was 17.8 h and of the liposome lipid matrix, 18.2 h (A). The half-life of the drug release from liposomes in the blood was $t_{1/2}$=677 h (B). Thus, these liposomes were extraordinarily stable against drug leakage in the bloodstream.

Example 40

Loading of Vinorelbine into Liposomes Using TEA-Pn Method. The Effect of pH

The liposomes were prepared by the ethanol injection method as in Example 11 using TEA-Pn solution of 0.608 M TEA, 0.65 M phosphate groups, pH 6.1, and osmolality 531 mmol/kg, and lipid suspension extrusion 15 times through two stacked 100 nm pore size polycarbonate membranes. The resulting liposome size was 108.3±17.1 nm by QELS Vinorelbine (VRB) in the form of stock solution of vinorelbine bitartrate 10 mg/mL USP was added to the liposomes in aqueous 5 mM HEPES-Na, 5% dextrose, pH 6.5, at a drug-to-phospholipid ratio of 350 μg/μmol, the pH was adjusted to the desired value using 1-5 N NaOH. and the mixture was incubated at 58±2° C. for 30 min. The mixture was then chilled on ice for 15 min, and unencapsulated drug was removed by Sephadex G-75 gel filtration chromatography, eluting with HBS-6.5 buffer (20 mM HEPES-Na, 135 mM NaCl, pH 6.5). Aliquots of purified liposomes were then solubilized in acid isopropanol and analyzed for vinorelbine using spectrophotometry at 270 nm. Liposome phospholipid was quantified using the phosphate assay of Bartlett (1959) after methanol-chloroform extraction.

The calculated drug-to-lipid ratios after loading were as shown in Table 24. Vinorelbine loading was quantitative (i.e. practically 100%) and independent of pH in the studied range.

TABLE 24

Vinorelbine loading into liposomes with entrapped TEA-Pn at various pH values of external buffer

| pH | Drug-to-phospholipid ratio (μg/μmol) | Loading efficiency (%) |
|---|---|---|
| 4.5 | 351.2 ± 52.88 | 100.4 ± 15.2 |
| 5.0 | 347.6 ± 6.35 | 99.3 ± 1.8 |
| 5.75 | 355.2 ± 11.2 | 101.5 ± 3.2 |
| 6.25 | 377.0 ± 21.5 | 107.7 ± 6.6 |
| 7.0 | 374.3 ± 29.58 | 106.9 ± 9.0 |

Example 41

Liposomal Vinorelbine Prepared by TEA-Pn Method at Various Drug/Lipid Ratios: Encapsulation Efficiency and In Vivo Stability in Mice Liposomes with entrapped TEA-Pn solution were prepared according to Example 40 except that [$^3$H]-CHE was included in the lipid matrix at 1.5 mCi/mmol phospholipid. The liposome size was 98.5±34.3 nm by QELS. The liposomes were mixed with vinorelbine bitartrate USP in aqueous buffer of 5 mM HEPES-Na, 5% dextrose, pH 6.5 at the drug-to-phospholipid ratio of 150-450 mg VRB/mmol, and incubated at 58±2° C. for 30 min. No pH adjustment was made following the addition of the drug. The vinorelbine-loaded liposomes (Ls-VRB) were isolated and analyzed for the drug and phospholipid as in Example 40.

Female five-six week old Swiss Webster mice (Harlan Bioresearch) in the groups of three were injected intravenously with Ls-VRB-Pn at a dose of 5 mg VRB/kg. The lipid dose varied according to the degree of loading and can be determined from the above calculated drug-to-lipid ratios. At 8 hours or 24 hours post injection, the animals were anesthetized, exsanguinated, and the blood was collected on ice into weighed tubes containing known amounts of PBS with 0.04% EDTA. The blood cells were separated by centrifugation, and the supernatants were analyzed for liposome lipid by [$^3$H]-CHE radioactivity scintillation counting and for vinorelbine using HPLC as follows. The samples were spiked with vinblastine (internal standard), extracted with diethyl ether, evaporated, and the residues were dissolved in the mobile phase consisting of aqueous 50 mM triethylammonium acetate (pH 5.5) and acetonitrile (58:42 by volume) The samples were loaded on a $C_{18}$ reverse phase silica column (Supelco C-18 column, 250 mm×4 mm i.d., particle size of 5 μm) preceded by a C-18 guard column. The column was eluted isocratically with the above mobile phase at a flow rate of 1.0 ml/min. VRB was detected using an absorbance detector at 280 nm. Typical retention times for VRB and vinblastine (internal standard) were 9.1 min and 7.8 min, respectively.

The results are shown in Table 25. The loading efficiency decreased with the increase in drug/lipid ratio, from practically 100% at 150 mg/mmol to about 66% at 450 mg/mmol. It was noted that the addition of vinorelbine bitartrate at the ratios of over 250 mg vinorelbine per mmol phospholipid caused substantial acidification of the liposome suspension (pH<4.0) that lead to reduced loading efficiency. Thus, the need for pH control during the drug loading step was established. The amounts of liposome matrix detected in the blood after 8 hours were in the range of 30.4±6.6% of injected dose (% id) to 38.6±5.2% id without apparent relation to the absolute amount of injected lipid. After 24 hours there was still from 6.4% ID to 14.8% ID of the lipid matrix detectable in the blood. The amount of drug that remained encapsulated after 8 hours varied from 37% to 63%. However, as 24 hours post injection the drug levels dropped below detection limit of the employed analytical method.

TABLE 25

Encapsulation efficiency and in vivo drug retention of liposomal vinorelbine prepared at different drug/lipid ratios using TEA-Pn method (without loading buffer pH adjustment). The drug retention data are mean ± SD (N = 3).

| Vinorelbine/phospholipid ratio | | | |
|---|---|---|---|
| Input, mg/mmol, calculated | Output, mg/mmol, calculated | Encapsulation efficiency, % | % drug remaining encapsulated at 8 hours post injection |
| 150 | 156 | 104.0 | 36.6 ± 4.2 |
| 250 | 238 | 95.2 | 53.3 ± 1.3 |
| 350 | 260 | 74.3 | 65.9 ± 2.3 |
| 450 | 299 | 66.4 | 63.0 ± 4.1 |

Example 42

Vinorelbine Loading into Liposomes Using TEA-SOS Method at Various Drug/Lipid Ratios TEA-SOS liposomes for drug loading were prepared as in Example 40 except that the TEA-SOS solution with 0.65 M TEA, pH 5.4, osmolality 521 mmol/kg was used instead of TEA-Pn solution, and the liposomes were extruded through 80 nm pore size polycarbonate membranes. The liposome size was 86.6±12.9 nm by QELS. VRB was added to the liposomes in aqueous 5 mM HEPES-Na, 5% Dextrose, pH 6.5, at various drug-to-phospholipid ratios, and the mixture was subsequently incubated at 60° C. for 30 min. The VRB-loaded liposomes were then isolated and analyzed as in Example 40.

The calculated drug-to-lipid ratios in the VRB liposomes are shown in Table 26. Remarkably, as opposed to polymeric anion assisted loading, vinorelbine loading in the liposomes with polyanionized sugar (sucrose octasulfate) was practically quantitative independently of the drug/lipid ratio for up to 450 mg VRB/mmol phospholipid, and only slightly less (88%) at 550 mg VRB/mmol phospholipid.

TABLE 26

Dependence of vinorelbine loading into liposomes on drug-to-lipid ratio

| Vinorelbine/phospholipid ratio, mg/mmol | | |
|---|---|---|
| Total | Encapsulated into liposomes | Loading efficiency (%) |
| 150 | 159.9 ± 11.5 | 106.6 ± 8.1 |
| 250 | 255. ± 12.4 | 102.2 ± 5.1 |
| 350 | 381.8 ± 16.3 | 109.1 ± 5.1 |
| 450 | 456.1 ± 29.5 | 101.4 ± 6.6 |
| 550 | 486.2 ± 26.0 | 88.4 ± 4.2 |

Example 43

Figure 18:
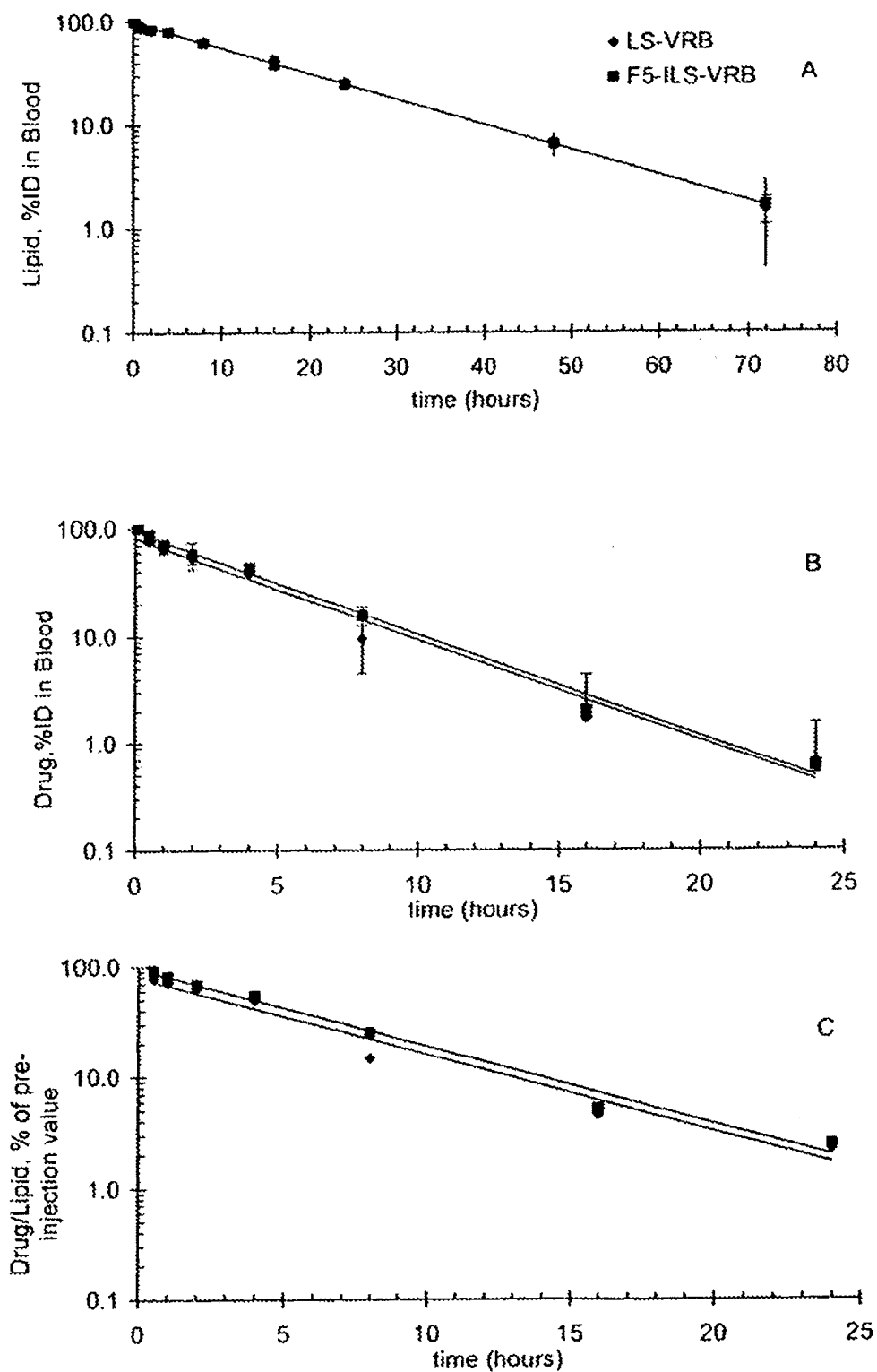
FIG. 18 shows blood pharmacokinetic attributes of vinorelbine formulated into liposomes (Ls-VRB), and anti-HER2 immunoliposomes (F5-ILs-VRB): blood pharmacokinetics of the liposome lipid (Panel A), the drug (Panel B), and the dynamics of drug-to-liposome lipid ratio (Panel C) after i.v. bolus administration of vinorelbine liposomes to a rat. (See Example 43).

Preparation of HER2-Targeted Immunoliposomes Loaded with Vinorelbine by TEA-Pn Method, and Comparative Blood Pharmacokinetics of HER2-Targeted and Nontargeted Vinorelbine Liposomes in Rats Anti-HER2 scFv F5-PEG-DSPE conjugate was prepared as in Example 19. HER2-targeted vinorelbine immunoliposomes were prepared by incubation of non-targeted vinorelbine liposomes (Example 41, loaded at drug/phospholipid ratio of 350 mg/mmol) with F5-PEG-DSPE conjugate (Example 19) in aqueous 20 mM HEPES-Na, 135 mM NaCl, pH 6.5 buffer at the protein/phospholipid ratio of 15 mg/mmol at 60° C. for 30 min. Unincorporated F5 conjugate was removed by gel chromatography on a Sepharose 4B column eluted with the same buffer. Non-targeted liposomes (Ls-Pn-VRB) and HER2-targeted ones (F5-ILs-Pn-VRB) were administered i.v. to female Albino rats (8-9 weeks old; 200 g) at a dose of 5 mg VRB/kg. At various time points, blood was collected as described in Example 9, and analyzed for VRB and the liposome lipid as in Example 41. Blood half-life of the liposome lipids and the 50% drug release time were calculated from the lipid concentration-time plots or by drug/lipid ratio-time plots, respectively, by finding best fit to monoexponential kinetics using the MICROSOFT EXCEL (Microsoft Corp.) spreadsheet TREND function. The results (FIG. 18) indicated that both targeted and non-targeted vinorelbine liposomes had identical drug and lipid pharmacokinetics with lipid half-life of about 12.1 hours and 50% drug release time of about 4.3 hours.

Example 44

Preparation and Comparative In Vivo Stability of Vinorelbine Liposomes Prepared Using Ammonium and Substituted Ammonium Salts Ammonium dextran sulfate (DS-A) solution with pH 5.8, 0.65 M $NH_4^+$, osmolality of 390 mmol/kg, and triethylammonium dextran sulfate solution (DS-TEA) with pH 6.0, 0.65 M $NH_4^+$, osmolality 465 mmol/kg, were prepared from Dextran sulfate with mol. weight 10,000 (Sigma Chemical Co.) according to the method of Example 4, using titration with 12.4 M aqueous ammonia or neat triethylamine, respectively. Ammonium sulfate (S-A) aqueous solution 325 mM, pH 5.1, osmolality 703 mmol/kg, was prepared from analytical grade ammonium sulfate. All three solutions contained less than 1% $Na^+$ of the total cation content. Liposomes entrapping these solutions were prepared using the ethanol mixing-extrusion method of Example 41 (DSPC/Cholesterol/PEG-DSPE 3:2:0.015 molar ratio). Radioactive lipid label [$^3$H]-CHE was included in the lipid matrix at 1.5 mCi/mmol phospholipid. Extrusion step consisted of 10 passages through two stacked 0.1 µm polycarbonate membranes. VRB was added to the liposomes in 5 mM HEPES-Na, 5% Dextrose, pH 6.5, at a drug-to-phospholipid ratio of 350 mg/mmol, the pH was adjusted to 6.5 using 1 N NaOH, and the mixture was incubated at 58-60° C. for 30 min. The reaction was then chilled on ice for 15 min, and unencapsulated drug was removed using Sephadex G-75 gel filtration chromatography, eluting with aqueous 20 mM HEPES-Na, 135 mM NaCl, pH 6.5. The purified, vinorelbine-loaded liposomes were analyzed for VRB spectrophotometrically and for phospholipid using the phosphate assay of Bartlett (1959) (see Examples 70, 71). Blood pharmacokinetics of the liposomal lipid and drug was studied in rats as in Example 43.

Figure 19:
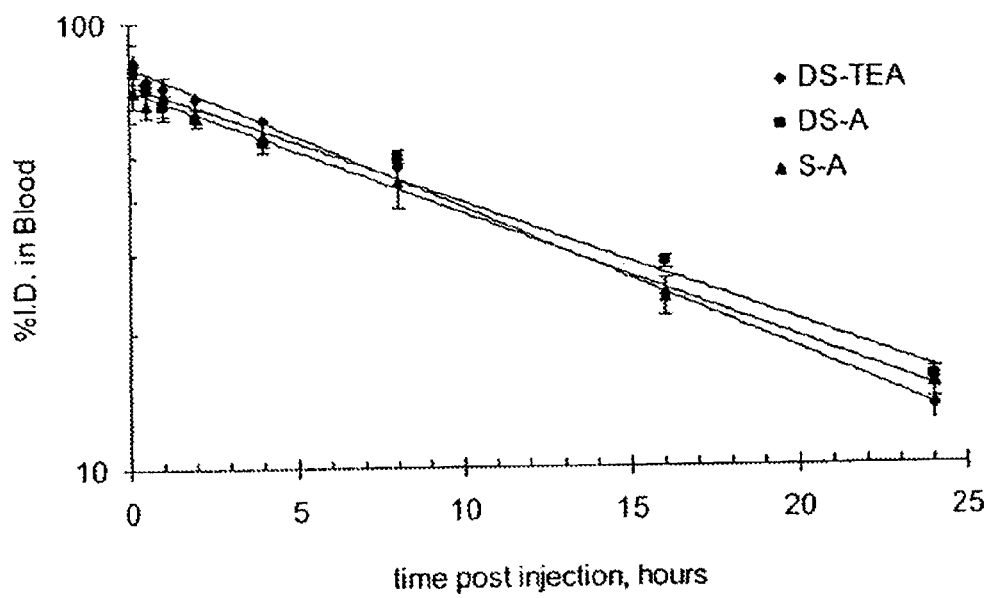
FIG. 19 shows blood pharmacokinetics of the liposome lipid after i.v. bolus administration of vinorelbine-loaded liposomes to a rat. The liposomes are loaded using pre-entrapped triethylammonium dextransulfate (DS-TEA), ammonium dextransulfate (DS-A), or ammonium sulfate (S-A). (See Example 44).
Figure 20:
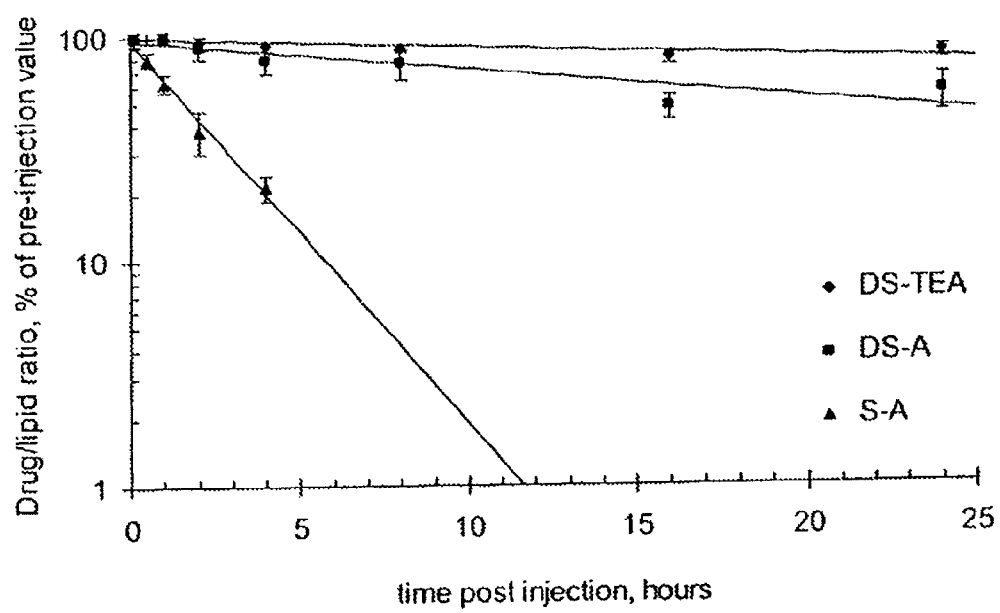
FIG. 20 shows the dynamics of drug-to-liposome lipid ratio in the blood of a rat in vivo following i.v. bolus administration of the liposomes loaded with vinorelbine using pre-entrapped triethylammonium dextransulfate (DS-TEA), ammonium dextransulfate (DS-A), or ammonium sulfate (S-A). (See Example 44).

The results are shown in FIGS. 19-20, and in Table 27. Liposomes loaded with triethylammonium dextransulfate were compared with those loaded using ammonium salt of dextran sulfate. Unexpectedly, those loaded using the triethylammonium salt were considerably more stable than those loaded using ammonium salt. The pharmacokinetics of the liposomal carrier itself was similar with the three different formulations and was thus primarily dependent on the lipid composition employed. Leakage of vinorelbine from Ls-VRB loaded using triethylammonium dextran sulfate was about three times slower than from those loaded using ammonium dextransulfate. The liposomes loaded using ammonium sulfate had the fastest drug leakage rate.

TABLE 27

Comparative in vivo stability of drug encapsulation into liposomes using entrapped ammonium and substituted ammonium salt.

| Formulation, liposome-entrapped salt | Liposome size, nm, mean ± SD (by QELS) | Blood half-life of the lipid matrix, hours | Time to 50% drug release in the blood, hours |
|---|---|---|---|
| DS-TEA | 120.8 ± 28.5 | 9.5 ± 3.3 | 66.3 ± 13.4 |
| DS-A | 107.8 ± 15.4 | 11.2 ± 0.6 | 22.9 ± 1.7 |
| S-A | 114.5. ± 15.6 | 10.7 ± 0.2 | 1.77 ± 0.16 |

Example 45

Preparation and In Vivo Stability of Vinorelbine Loaded Liposomes of Various Size

[$^3$H]-CHE-labeled liposomes (1.5 mCi/mmol phospholipid) with entrapped solution of triethylammonium sucrose octasulfate (0.65 M TEA, pH 6.4, osmolality 502 mmol/kg) were prepared by the ethanol mixing-extrusion method of Example 11. The extrusion step contained 15 passages through two stacked polycarbonate membranes with the pore size of 0.05, 0.08, or 0.1 µm. Vinorelbine loading, isolation of vinorelbine liposomes, and liposome characterization followed the method of Example 40. Female Albino rats (8-9 weeks old; 200 g) were used to study liposome in vivo stability. Liposome lipid and drug pharmacokinetics was studied in rats as in Example 43.

Figure 21:
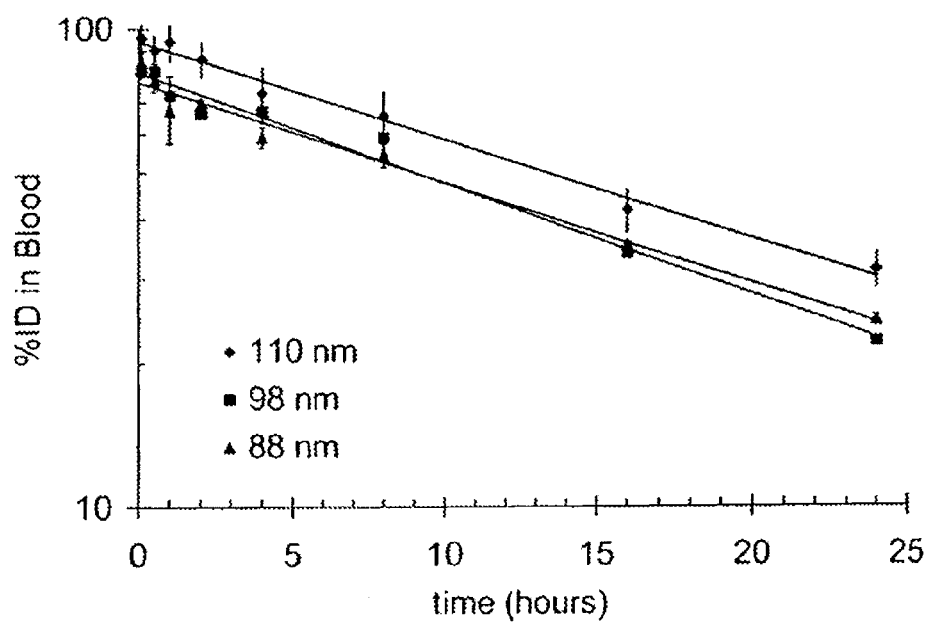
FIG. 21 shows blood pharmacokinetics of the liposome lipid after i.v. bolus administration of vinorelbine-loaded liposomes to a rat. The liposomes are loaded using pre-entrapped triethylammonium sucroseoctasulfate (TEA-SOS) and have the mean size as indicated at the on-panel caption. (See Example 45).
Figure 22:
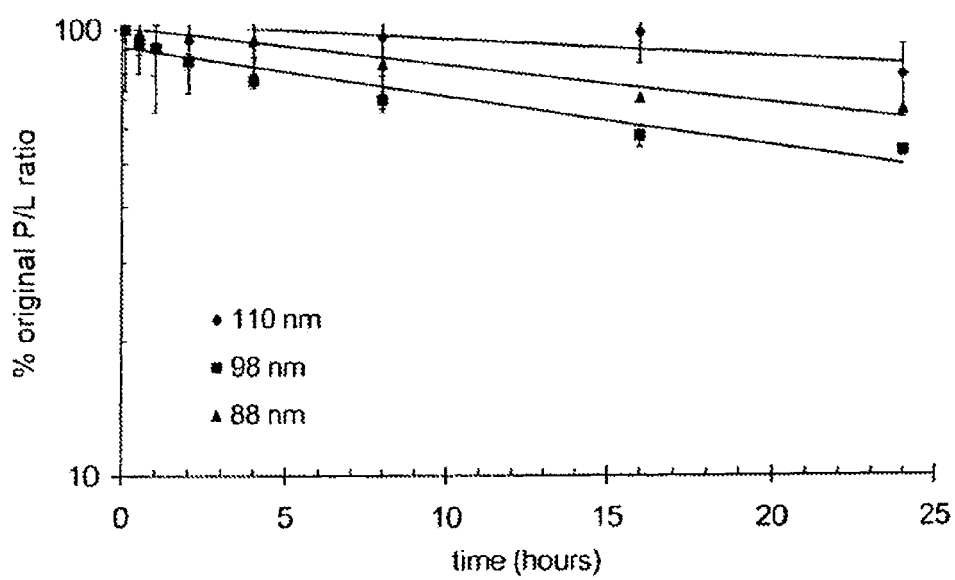
FIG. 22 shows the dynamics of drug-to-liposome lipid ratio in the blood of a rat in vivo following i.v. bolus administration of vinorelbine-loaded liposomes. The liposomes are loaded using pre-entrapped triethylammonium sucrooctasulfate (TEA-SOS) and have the mean size as indicated at the on-panel caption. (See Example 45).

The results are shown in FIGS. 21, 22, and in the Table 28 below. Liposomes extruded through 0.05, 0.08, and 0.1 μm polycarbonate filters were compared and shown to have similar drug and liposomal carrier pharmacokinetics, as well as a similar extent of contents leakage. The drug release from the liposomes in blood was characterized by the 50% release times in the range of approximately 40-80 hours, well above 24 hours.

TABLE 28

Characterization of vinorelbine liposomes.

| Liposome size, nm, mean ± SD (by QELS) | Drug load, mg/mmol phospholipid | Loading efficiency, % | Blood half-life of the lipid matrix, hours | Time to 50% drug release in the blood, hours |
|---|---|---|---|---|
| 87.6 ± 28.1 | 352.4 ± 13.9 | 100.7 ± 4.0 | 14.6 ± 0.7 | 39.7 ± 3.1 |
| 98.5 ± 15.1 | 322.6 ± 22.7 | 92.2 ± 6.5 | 13.0 ± 0.2 | 47.9 ± 3.8 |
| 109.6 ± 24.6 | 357.0 ± 10.5 | 102.0 ± 3.0 | 14.3 ± 0.3 | 78.0 ± 1.4 |

Example 46

Figure 23:
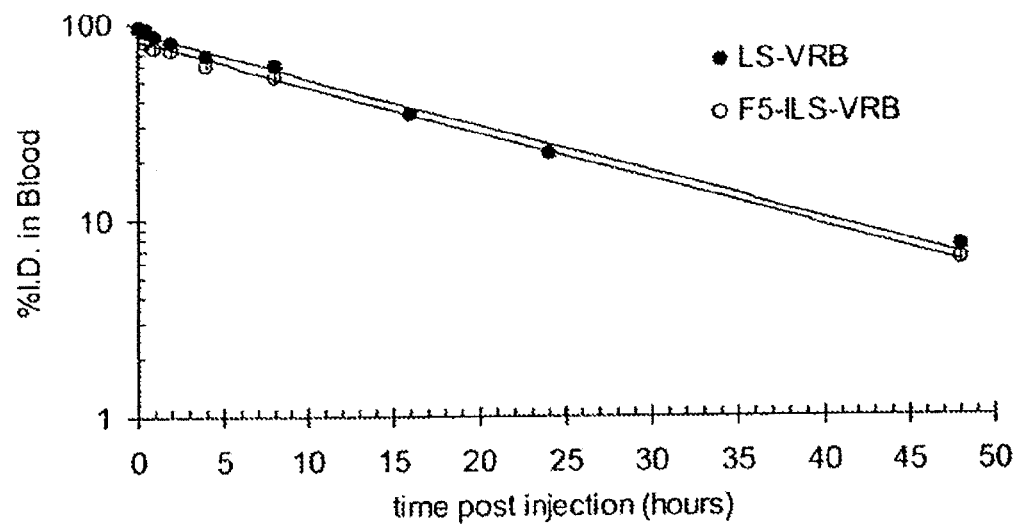
FIG. 23 shows blood pharmacokinetics of the liposome lipid in a rat after i.v. bolus administration of vinorelbine formulated into liposomes (Ls-VRB) or anti-HER2 immunoliposomes (F5-ILs-VRB) using TEA-SOS method. (See Example 46).
Figure 24:
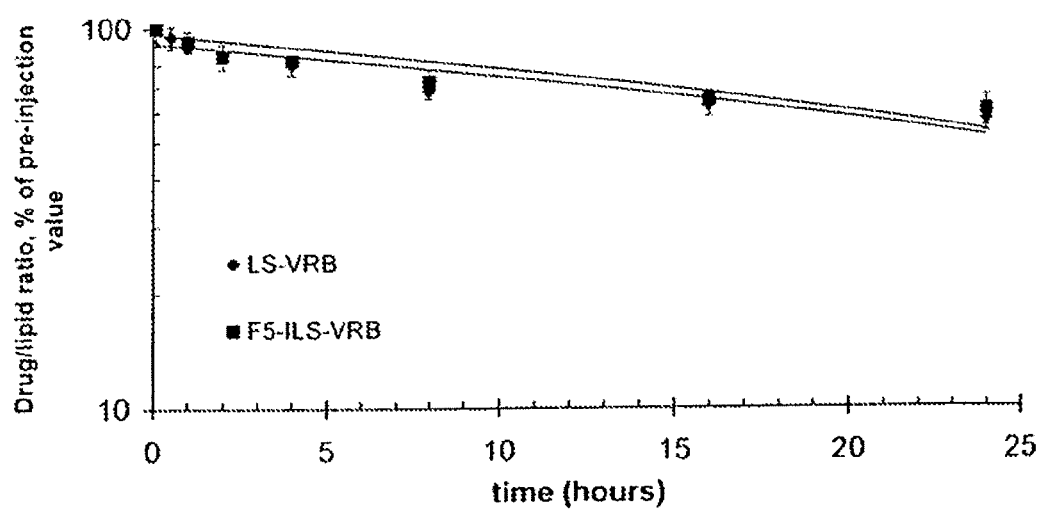
FIG. 24 shows the dynamics of drug-to-liposome lipid ratio in the blood of a rat in vivo following i.v. bolus administration of vinorelbine formulated into liposomes (Ls-VRB) or anti-HER2 immunoliposomes (F5-ILs-VRB) using TEA-SOS method. (See Example 46).

Preparation of HER2-Targeted Vinorelbine Liposomes Using TEA-SOS Entrapment Method, and Pharmacokinetics of HER2 scFv-Targeted and Non-Targeted Immunoliposomal Vinorelbine in Rats Liposomes were prepared, loaded with vinorelbine at the 350 mg/mmol drug-phospholipid ratio, and analyzed as described in Example 43, except that TEA-SOS solution of Example 45 was substituted for TEA-Pn solution. Extrusion step included 15 passages through 0.08 μm pore size polycarbonate filters. The liposome size was 95.0±26.0 nm by QELS. F5scFv-linked anti-HER2 vinorelbine immunoliposomes were prepared from these vinorelbine liposomes, and blood pharmacokinetics of the liposomal lipid and drug of HER2-targeted and nontargeted liposome vinorelbine was studied in rats as described in Example 43. Circulation half-life of the liposome lipid was 11.4 hours and 10.3 hours, and the 50% drug release time was 30.9 hours and 30.3 hours for F5-ILs-VRB and Ls-VRB, respectively. Thus, the lipid and drug pharmacokinetics of Ls-VRB and F5-ILs-VRB was very close, indicating that the introduction of the scFv-PEG-DSPE conjugate neither affected clearance of the carrier itself nor resulted in increased leakage of the drug from the carrier while in the circulation (FIGS. 23, 24).

Example 47

Preparation and Pharmacokinetic Properties of Vinorelbine Liposomes Comprising Non-Ionic Lipid Derivatives of Poly(Ethylene Glycol)

Methoxy-PEG (Mol. weight 2,000)-derivative of synthetic $C_{20}$-ceramide (PEG-ceramide) was obtained from Northern Lipids, Inc., Canada. Methoxy-PEG(Mol. weight 2,000)-distearoylglycerol (PEG-DSG) (SUNBRIGHT GS20) was from NOF Corp., Japan.

Liposomes having the lipid composition of DSPC, cholesterol, and PEG-lipid (PEG-ceramide or PEG-DSG) in the molar ratio of 3:2:0.3 and entrapped TEA-SOS solution (0.65 M TEA, pH 6.4, osmolality 502 mmol/kg) were prepared by the ethanol mixing/extrusion method of Example 11. The extrusion step included two passages through two stacked polycarbonate membrane filters 2 times using pore size 0.2 μm and 10 times using 0.08 μm pore size. The liposomes were loaded with vinorelbine at the drug/phospholipid ratio of 350 mg/mmol, characterized by size, drug, and lipid concentration, and their pharmacokinetics was studied in rats as in Example 46. Both formulations showed prolonged circulation time of the lipid matrix and slow release of the drug in vivo, with at least 50% of the drug remaining encapsulated after 24 hour in the blood in vivo, as shown in the Table 29 below.

TABLE 29

Characterization of vinorelbine liposomes with various PEG-lipids.

| PEG-lipid | Liposome size, nm, mean ± SD (by QELS) | Drug load, mg/mmol phospholipid | Loading efficiency % | Blood half-life of the lipid matrix, hours | Time to 50% drug release in the blood, hours |
|---|---|---|---|---|---|
| PEG-ceramide | 103.3 ± 30.9 | 291.4 ± 18.0 | 83.26 ± 5.14 | 14.0 | 102.7 |
| PEG-DSG | 101.3 ± 20.1 | 359.3 ± 7.2 | 102.7 ± 2.1 | 15.1 | 24.6 |

Remarkably, the increased PEGylation of these liposomes (PEG lipid content about 5.7 mol. % of the total lipid) had practically no effect on the liposome blood circulation longevity compared to the similar, size-matched liposomes having low PEGylation of about 0.3 mol. % of total lipid (Example 45, 109.6 nm, $t_{1/2}$=14.3 hours; 98.5 nm, $t_{1/2}$=13.0 hours).

Example 48

Preparation of HER2-Targeted Liposomal Vinorelbine and Cytotoxicity of Free, HER2-Targeted, and Non-Targeted Liposomal Vinorelbine Against MDA-MB-453 Cells In Vitro Vinorelbine-loaded liposomes (Ls-VRB) were prepared as in Example 42 (without [$^3$H]-CHE) using drug loading at pH 6.0 and 350 μg vinorelbine/μmol phospholipid. Anti-HER2 immunoliposomal vinorelbine (F5-ILs-VRB) was formed by incubating these liposomes with F5-PEG-DSPE conjugate as described in Example 19 and 42 above, except that [$^3$H]-CHE was not added. "Free" vinorelbine was prepared by dilution of vinorelbine bitartrate 10 mg/ml solution USP into the cell culture medium.

Figure 25:
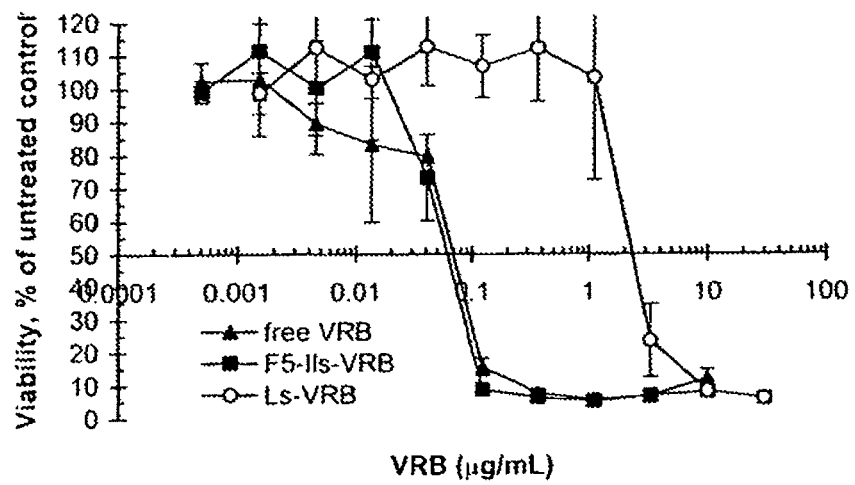
FIG. 25 shows the in vitro cytotoxicity of free vinorelbine (free VRB), liposomal vinorelbine (Ls-VRB), or HER2-targeted immunoliposomal vinorelbine (F5-Ils-VRB) against HER2-overexpressing human breast cancer cells MDA-MB-453. (See Example 48).

MDA-MB-453 are human breast adenocarcinoma cells (American Type Culture Collection, Rockville, Md.) that moderately overexpresses HER2 receptor (about $3 \times 10^4$ to $1 \times 10^5$ copies/cell). Cytotoxicity of VRB delivered as the free drug, as nontargeted liposomal vinorelbine, or as HER2-targeted (F5)-immunoliposomal vinorelbine against MDA-MB-453 cells was determined as described in Example 27, except that the cells were plated in 96 well microtiter plates under the supplier-recommended growth conditions (Leibowitz L-15 with 10% fetal calf serum, no $CO_2$ supplementation) at a density of 10,000 cells/well, and the drug formulations were added in a series of 1:3 stepwise dilutions starting with 0.03-0.1 mg/ml. The cell viability data were plotted against drug concentration (FIG. 25) and drug concentrations required to reduce the cell viability to 50% ($IC_{50}$) were estimated from the graphs. $IC_{50}$ of F5-targeted vinorelbine liposome 0.06 µg/ml) was close to that of the free drug (0.07 µg/ml) and substantially lower than that of non-targeted liposomes (2.2 µg/ml). This represents a 37-fold enhancement in activity as a result of cancer cell-specific targeted delivery of the drug.

Example 49

Figure 26:
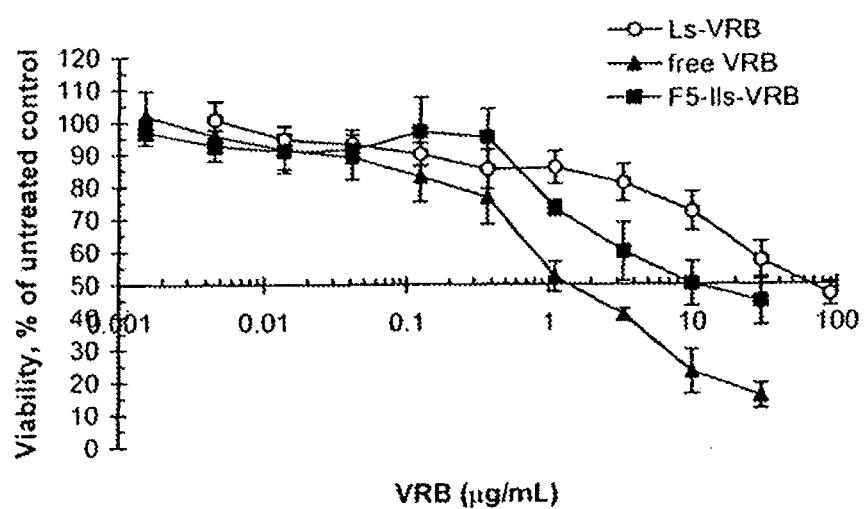
FIG. 26 shows the in vitro cytotoxicity of free vinorelbine (free VRB), liposomal vinorelbine (Ls-VRB), or HER2-targeted immunoliposomal vinorelbine (F5-Ils-VRB) against HER2-overexpressing CaLu-3 human non-small cell lung cancer cells. (See Example 49).

Cytotoxicity of Free, HER2-Targeted, and Non-Targeted Liposomal Vinorelbine Against CaLu-3 Cells In Vitro The liposomes and methods of the previous example (Example 48) were used to study cytotoxicity of free vinorelbine, Ls-VRB, and F5-ILs-VRB in HER2-overexpressing human non-small cell lung carcinoma cells CaLu-3 (American Type Culture Collection, Rockville, Md.). The cells were grown in RPMI-1460 medium with 10% fetal calf serum in the presence of 5% $CO_2$. The results are shown in FIG. 26. The $IC_{50}$ for free VRB was 1.2 µg/ml, 10 µg/ml for F5-ILs-VRB, and 50 µg/ml for nontargeted Ls-VRB. This represents a 5-fold enhancement in liposome-encapsulated drug activity as a function of targeted delivery to the cells.

Example 50

Cytotoxicity of Free, HER2-Targeted, and Non-Targeted Liposomal Vinorelbine Against SKBr-3 Cells In Vitro The liposomes and methods of Example 48 and the were used to study cytotoxicity of free vinorelbine, Ls-VRB, and F5-ILs-VRB in HER2-overexpressing human breast carcinoma cells SKBr-3 (American Type Culture Collection, Rockville, Md.), except that the cells were grown in the modified McCoy 5A medium with 10% fetal calf serum in the presence of 5% $CO_2$, plated at a density of 5,000 cells/well, and the drug was incubated with the cells for 6 h.

Figure 27:
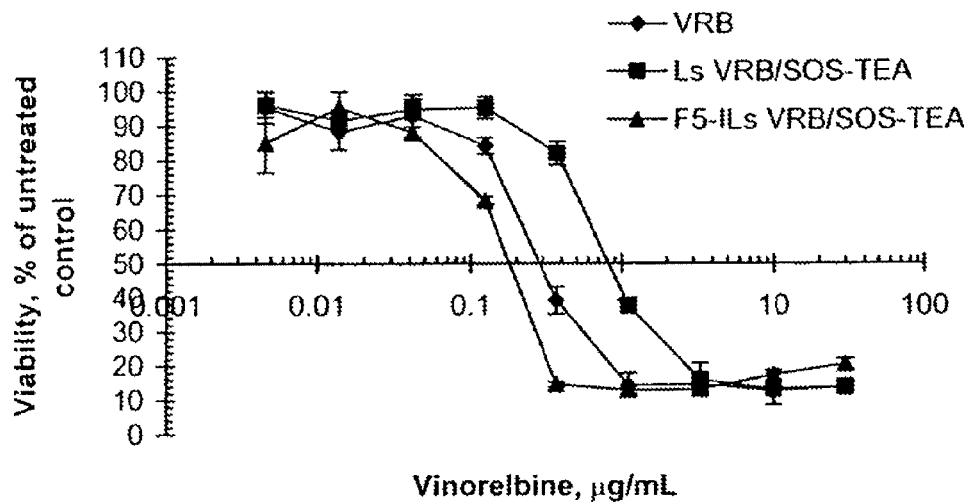
FIG. 27 shows the in vitro cytotoxicity of free vinorelbine (free VRB), liposomal vinorelbine (Ls VRB/SOS-TEA), or HER2-targeted immunoliposomal vinorelbine (F5-ILs VRB/SOS-TEA) against HER2-overexpressing human breast cancer cells SKBr-3. (See Example 50).

The results are shown in FIG. 27. The $IC_{50}$ for free VRB was 0.28 µg/ml, 0.17 µg/ml for F5-ILs-VRB, and 0.8 µg/ml for nontargeted Ls-VRB. This represents a 4.7-fold enhancement in drug activity as a function of targeted delivery.

Example 51

In Vivo Antitumor Efficacy of Liposomal Vinorelbine in HT29 Human Colon Cancer Xenografts in Mice Small unilamellar vesicle liposomes (93.2±26.4 nm by QELS) were prepared from distearoylphosphatidylcholine, cholesterol, and PEG-DSPE (3:2:0.045 molar ratio) by hydration from a concentrated ethanolic solution in an aqueous solution of triethylammonium sucroseoctasulfate (0.6 M triethylammonium, pH 5.7-6.2), followed by repeated extrusion through polycarbonate membranes (100 nm pore size), removal of extraliposomal polyanionic salt, and loading with vinorelbine by incubation with the liposomes in isoosmotic buffer pH 6.5, drug/lipid ratio of 325 mg VRB/mmol phospholipid, at 60° C. as described in Example 42.

Figure 28:
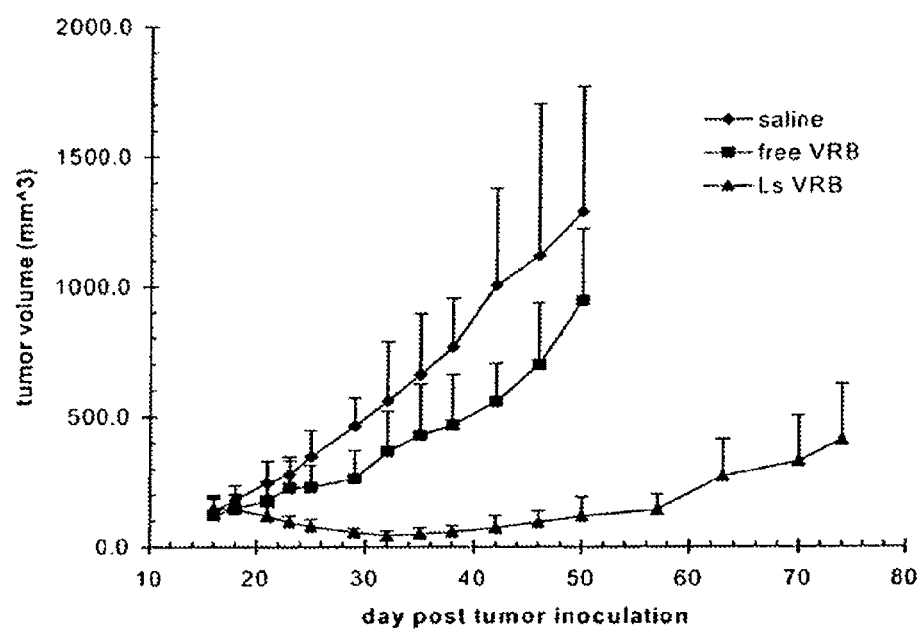
FIG. 28 shows antitumor efficacy of the free vinorelbine (free VRB) or liposomal vinorelbine (Ls VRB) against HT-29 human colon cancer xenografts in nude mice. "Saline" designates the mice treated with drug- and liposome-free vehicle only. Error bars represent standard deviation of the data. (See Example 51).
Figure 29:
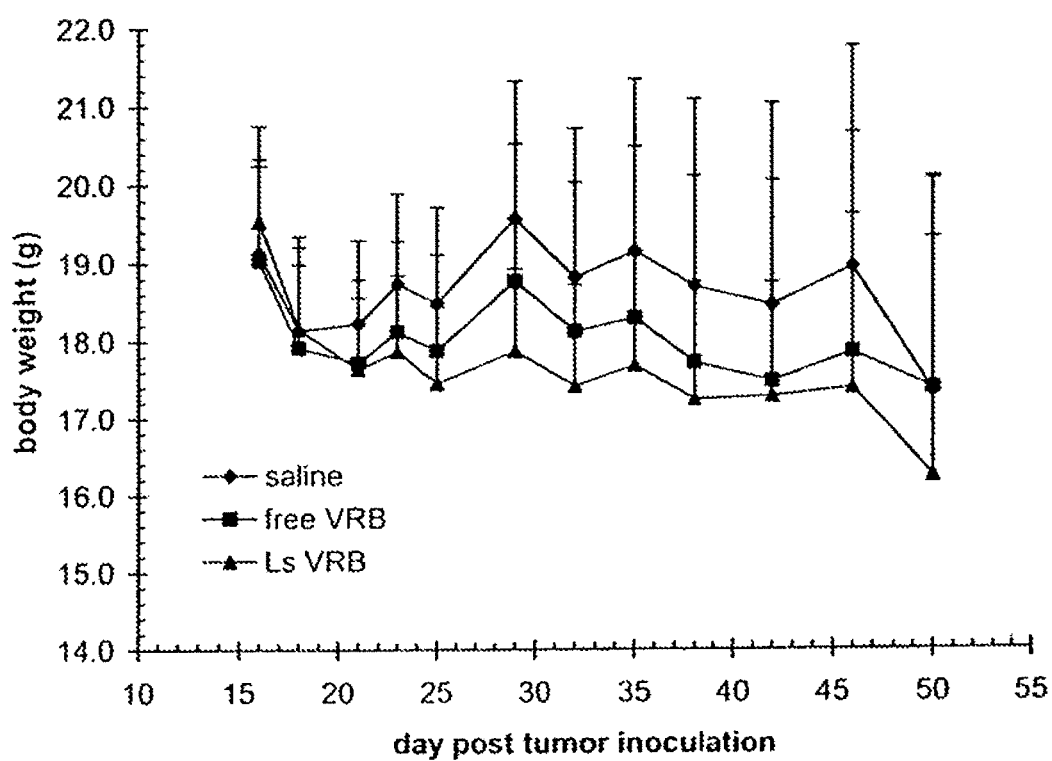
FIG. 29 shows the dynamics of the average body weights during the treatment of HT-29 tumor-bearing nude mice with free vinorelbine (free VRB), liposomal vinorelbine (Ls VRB), or vehicle only (saline). Error bars represent standard deviation of the data. (See Example 51).

Female BALB/c homozygous nude mice (6-8 weeks, weighing 17-20 g) were injected subcutaneously in the flank area with $1\times10^6$ of HT-29 human colon carcinoma cells (American Type Culture Collection, Rockville, Md.). Starting with day 16 post-tumor inoculation, when the mean tumor diameter reached 5-8 mm, the mice were randomly divided into three groups of six animals each and treated with free or liposomal vinorelbine at a dose of 5 mg/kg through the tail-vein every three days for a total of four injections. For the control group, mice were treated with an equal volume of saline. The tumor size of each mice was measured using a caliper and the tumor volume was calculated using the formula: (tumor length)×(tumor width)$^2$/2. To assess treatment-related toxicity, the animals were also weighed twice weekly. Liposomal vinorelbine was shown to be considerably more efficacious in suppressing the growth of HT-29 tumors that free vinorelbine, causing tumors to regress, while in the free drug group the tumors always continued to grow (FIG. 28). There was little change in animals' body weight during the course of treatment indicating that the treatment was well tolerated, and that liposomalization did not increase the drug toxicity (FIG. 29).

Example 52

Figure 30:
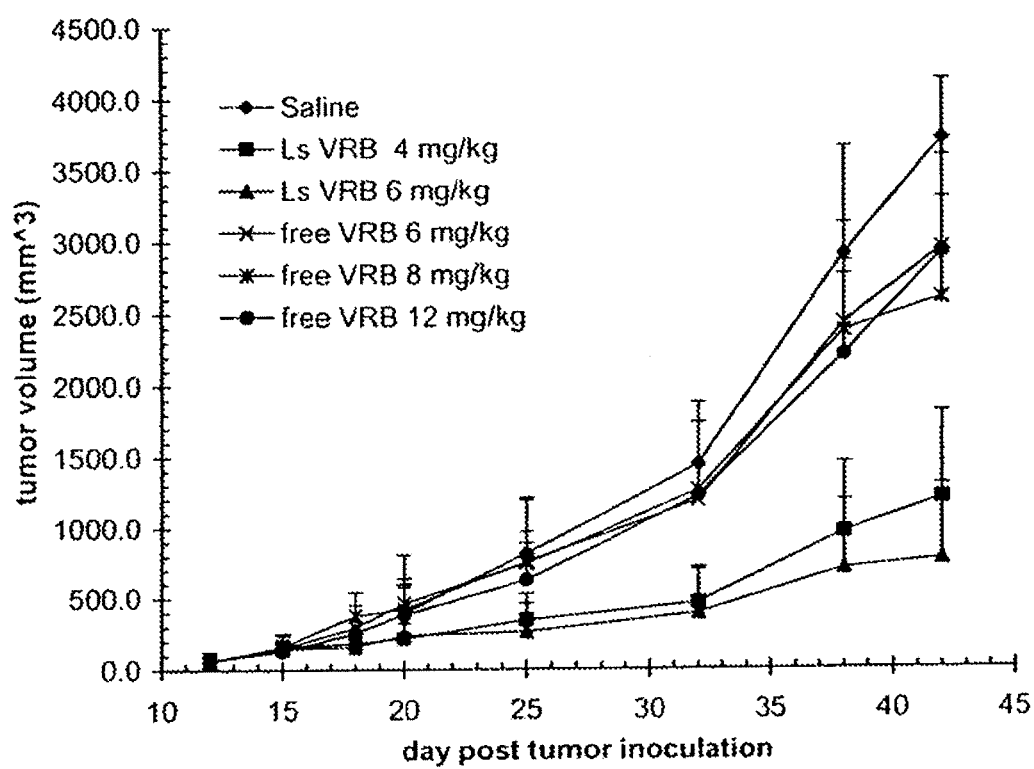
FIG. 30 shows antitumor efficacy of the free vinorelbine (free VRB) or liposomal vinorelbine (Ls VRB) in a syngeneic C-26 murine colon carcinoma model. The dose of the drug per injection was as indicated on the on-panel caption. Error bars represent standard deviation of the data. "Saline" designates the mice treated with drug- and liposome-free vehicle only. (See Example 52).
Figure 31:
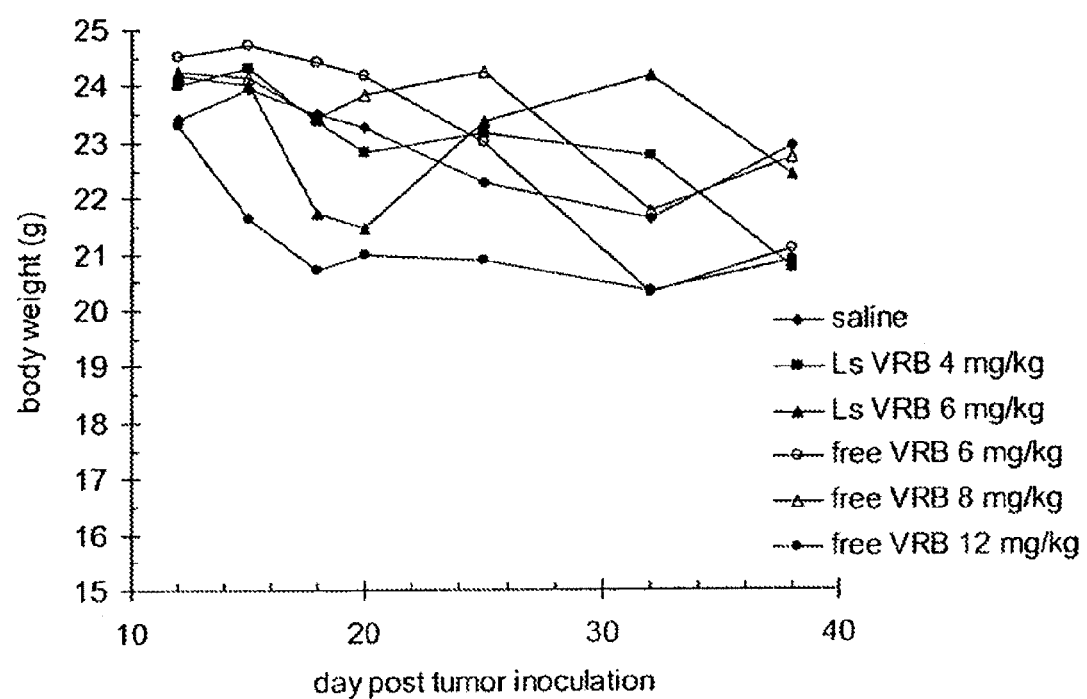
FIG. 31 shows the dynamics of the average body weights during the treatment of mice bearing syngeneic C-26 murine colon carcinoma tumors with various doses of free vinorelbine (free VRB), liposomal vinorelbine (Ls VRB), or with vehicle only (saline). The dose of the drug per injection was as indicated on the on-panel caption. (See Example 52).

In Vivo Antitumor Efficacy of Liposomal Vinorelbine Against C-26 Syngeneic Murine Colon Cancer Tumors Liposomal vinorelbine and free vinorelbine were prepared as in Example 48. Male BALB/c mice (6-8 weeks, weighing 17-20 g) were inoculated subcutaneously with $2\times10^5$ of C-26 murine colon carcinoma cells. At day 17 post-inoculation, when the mean tumor diameter reached 5-8 mm, mice were randomly divided into six treatment groups of five animals/group. The tumor bearing mice were injected through the tail-vein with free vinorelbine at 6 mg/kg, 8 mg/kg, or 12 mg/kg, and with liposomal vinorelbine at 4 mg/kg or 6 mg/kg every three days for a total of four injections. For the control group, mice were injected with equal volume of normal saline. Tumor sizes and animals body weights were followed as in Example 51. Liposomal vinorelbine even at 4 mg/kg, was considerably more efficacious in reducing the tumor growth than free drug at 12 mg/kg (FIG. 30), The animal body weights in the course of treatment showed little change (<10% decrease) indicating that the toxicity of liposomal vinorelbine was not increased compared to that of free drug (FIG. 31).

Example 53

Figure 32:
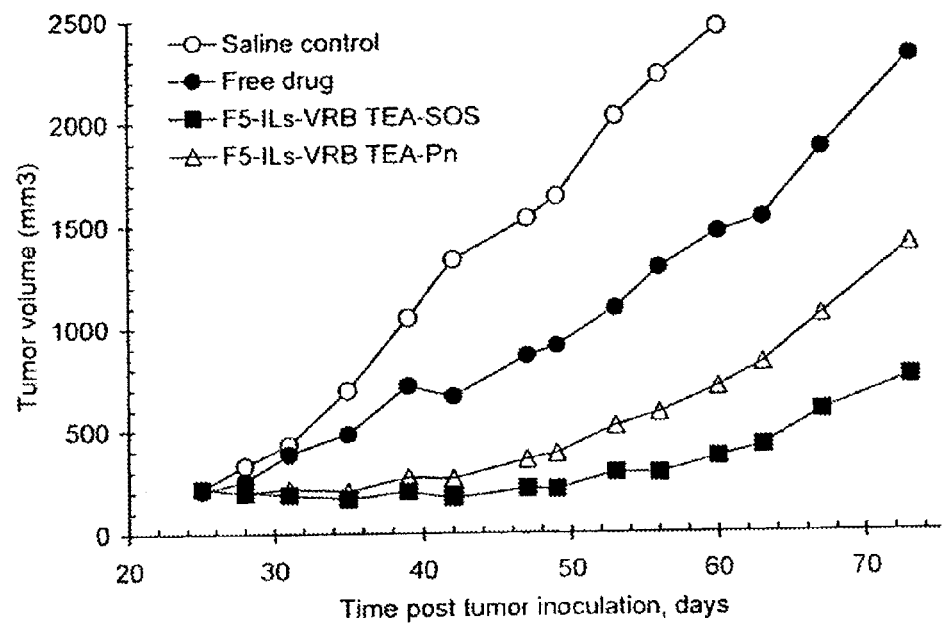
FIG. 32 shows antitumor efficacy of the free vinorelbine (Free drug) or scFv F5-conjugated, anti-HER2 immunoliposomal vinorelbine prepared by a TEA-SOS method (F5-ILs-VRB TEA-SOS), anti-HER2 immunoliposomal vinorelbine prepared y a TEA-Pn method (F5-ILs-VRB TEA-Pn) against HER2-overexpressing human breast carcinoma (BT-474) xenografts in nude mice. "Saline control" designates the mice treated with drug- and liposome-free vehicle only. (See Example 53).
Figure 33:
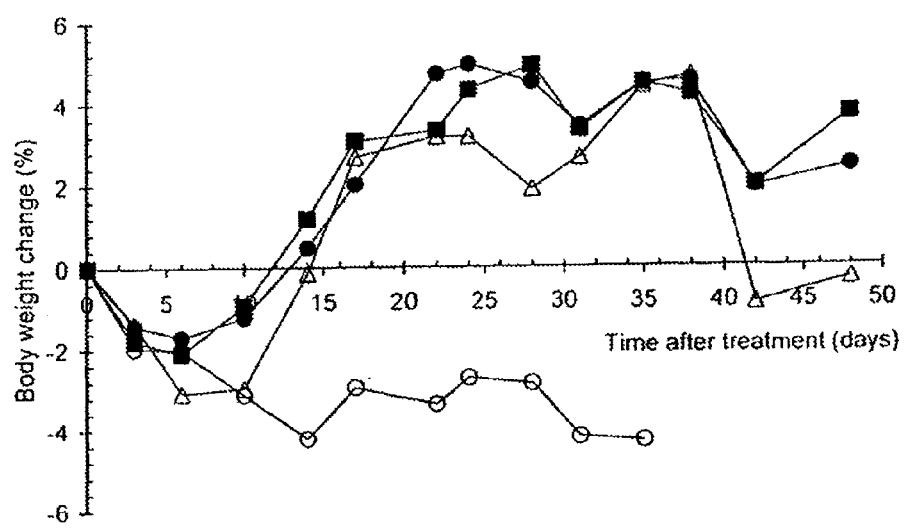
FIG. 33 shows the dynamics of the average body weights during the treatment of mice bearing HER2-overexpressing human breast carcinoma (BT-474) xenografts with free vinorelbine, scFv F5-conjugated, anti-HER2 immunoliposomal vinorelbine prepared using a TEA-SOS method, anti-HER2 immunoliposomal vinorelbine prepared by a TEA-Pn method, or with vehicle only. For explanation of the symbols, see the caption to FIG. 32. (See also Example 53).

In Vivo Antitumor Efficacy of HER2-Targeted Liposomal Vinorelbine Against BT-474 Human Breast Cancer Xenograft Tumors in Mice: Effect of Loading Counter-Ion VRB-loaded liposomes 99.5±10.2 nm in size were prepared by the TEA-Pn method of Example 41 and TEA-SOS method of Example 42, respectively, except that [$^3$H]-CHE was not added. VRB was loaded at the drug/phospholipid ratio of 350 mg/mmol. HER2-targeted liposomal vinorelbine was formed by incubating these liposomes with F5-PEG-DSPE conjugate (see Example 19) as described in Example 43. BT-474 HER2-overexpressing human breast carcinoma xenografts were raised in homozygous nude mice as in Example 10. At day 25 post tumor cell inoculation, when the tumors reached about 200 mm³ in size (range 144-309 mm³), the mice were randomized into four groups of eight animals/group, and treated i.v. with 5 mg/kg of free VRB, F5-ILs-VRB with Pn as a counter-ion, or F5-ILs-VRB with SOS as a counter-ion, at a dose of 5 mg/kg weekly for a total of three injections. The control group received equal volume of normal saline. The tumors and animal body weights were monitored as in Example 10. HER2-targeted liposomal vinorelbine loaded using sucrose octasulfate was noticeably more efficacious in reducing tumor growth than the same targeted construct loaded using poly(phosphate), and both immunoliposomal preparations were considerably more efficacious than free vinorelbine when administered at a dose of 5 mg VRB/kg (FIG. 32). The drug-treated mice demonstrated little change in weight indicating that the treatment was well tolerated (FIG. 33).

Example 54

Figure 34:
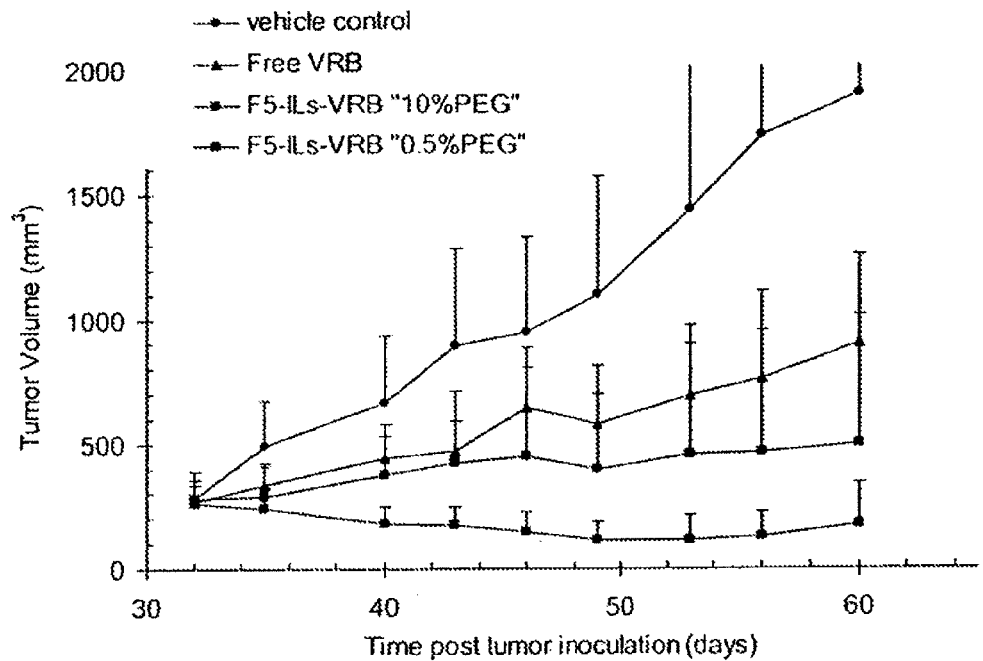
FIG. 34 shows antitumor efficacy of the free vinorelbine (Free drug) or scFv F5-conjugated, anti-HER2 immunoliposomal vinorelbine prepared using various amounts of PEG-lipid against HER2-overexpressing human breast carcinoma (BT-474) xenografts in nude mice. The error bars are standard deviation of the data. "Vehicle control" designates the mice treated with drug- and liposome-free vehicle only. (See Example 54).

In Vivo Antitumor Efficacy of HER2-Targeted Liposomal Vinorelbine Against BT-474 Human Breast Cancer Xenograft Tumors in Mice: Effect of PEGylation The liposomes of DSPC and cholesterol in the molar ratio 3:2 were prepared according to Example 48 by hydration of the lipid matrix of DSPC, cholesterol, and PEG-distearoyl-glycerol with PEG mol. weight 2,000 (GS-20, NOF Corp., Japan) at a molar ratio 3:2:0.015 ("0.5% PEG") or 3:2:0.3 ("10% PEG") via ethanolic solution method in an aqueous triethylammonium sucroseoctasulfate, followed by membrane extrusion according to Example 48. VRB was loaded into the liposomes at the drug/phospholipid ratio of 350 mg/mmol. F5 immunoliposomal vinorelbine was formed by incubating these liposomes with F5-PEG-DSPE conjugate (Example 19) as described in Example 43. Nude mice with BT-474 xenografts were raised and treated i.v. with free VRB, F5-ILs-VRB-"0.5% PEG", or F5-ILs-VRB-"10% PEG" at 5 mg/kg as in Example 53. As shown in FIG. 34, F5-ILs-VRB with higher PEGylation provided with a non-ionic PEG lipid derivative PEG-DSG was noticeably more efficacious in reducing tumor growth than F5-ILs-VRB with lower amount of PEG-DSG, while both preparations were more active than the free drug.

Example 55

In Vivo Antitumor Efficacy of EGFR-Targeted Liposomal Vinorelbine Against U87 Human Brain Cancer Xenograft Tumors in Mice The liposomes (86.6±12.9 nm in size by QELS) with encapsulated 0.65 M TEA-SOS solution were prepared and loaded with VRB according to Example 42. Anti-EGFR-immunoliposomal VRB (C225Fab'-ILs-VRB) was prepared by incubation of VRB liposomes with the PEG-DSPE conjugate of an anti-EGFR antibody Fab' fragments as described in Example 36.

Figure 35:
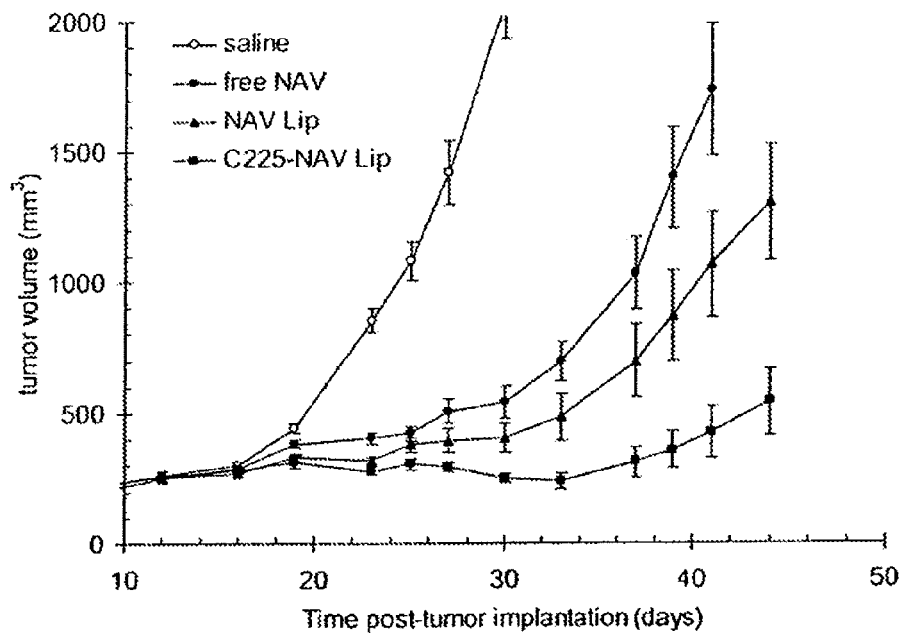
FIG. 35 shows antitumor efficacy of the free vinorelbine (free NAV), liposomal vinorelbine (NAV Lip), or FC225Fab'-conjugated, anti-EGFR-immunoliposomal vinorelbine (C225-NAV Lip) against EGFR-overexpressing human glioblastoma (U87) xenografts in nude mice. "Saline" designates the mice treated with drug- and liposome-free vehicle only. (See Example 55).

Male NCR nu/nu mice (5-6 weeks, weighing 17-20 g) were injected subcutaneously in the flank area with 1×10⁷ of U87 human glioblastoma cells (ATCC) suspended in the growth medium in a total volume of 150 μl. When the tumor reached an average size of 250 mm³, mice were randomly divided into four groups of 10-12 animals. The mice were treated with three weekly i.v. injections of "free" VRB, nontargeted Ls-VRB, or C225Fab'-ILs-VRB at a dose of 5 mg VRB/kg. The control group received an equal volume of saline. The tumor sizes and animal body weights were monitored as in Example 10. C225-Fab'-ILs-VRB was noticeably more efficacious in suppressing the growth of EGFR-overexpressing human brain cancer xenograft tumors than either non-targeted liposomal vinorelbine or free vinorelbine at an equal dose (FIG. 35).

Example 56

Preparation and Pharmacokinetics of Doxorubicin Encapsulated in the Liposomes Using Triethylammonium Sulfate Method Liposomes with various lipid matrix composition (as indicated in the table below) were formed as described in Example 2. N-Glutaryl-DSPE (Glu-DSPE) was from Avanti Polar Lipids, AL, USA. A neat lipid film was formed from the lipid solution in chloroform using rotary evaporation, trace volatiles were removed under vacuum (90 μm Hg, 2 hours), the lipid film was hydrated in a triethylammonium sulfate (TEA-SO₄) solution (0.65 N TEA), subjected to six cycles of rapid freeze and thaw, and extruded through two stacked 0.1 μm pore size polycarbonate filters ten times and through two stacked 0.05 μm pore size polycarbonate filters ten times. For lipid matrix quantification in the blood samples, [³H]-CHE was included in the lipid matrix at 0.5-1.5 mCi/mmol phospholipid. The liposomes with entrapped TEA-SO₄ solution were loaded with doxorubicin according to Example 2. The liposomes in HEPES-buffered saline (20 mM HEPES-Na, 135 mM NaCl, pH 6.5) were incubated with doxorubicin hydrochloride (drug/phospholipid ratios of 140-170 mg/mmol) at 60° C. for 45 min followed by quenching on ice and removal of unencapsulated doxorubicin by gel chromatography. Doxorubicin was assayed by spectrophotometry (Example 71), and phospholipid was assayed by Bartlett method (Example 70). The properties of resulting liposomes are summarized in Table 30 below.

TABLE 30

Properties of liposomal doxorubicin at various lipid compositions.

| Lipid composition (molar ratio) | Liposome size, nm (mean ± SD by QELS) | drug/phospholipid (mg/mmol) |
| --- | --- | --- |
| DSPC/Chol/PEG-DSPE (3:2:0.015) | 81.8 ± 27.3 | 163.6 ± 4.4 |
| DSPC/Chol (3:2) | 79.1 ± 27.9 | 137.0 ± 17.5 |
| DSPC/Chol/Glu-DSPE (2.85:2:0.15) | 83.6 ± 27.2 | 141.7 ± 10.4 |
| DSPC/Chol/PEG-DSPE (2.7:2:0.3) | 83.7 ± 23.1 | 175.0 ± 6.8 |

Figure 36:
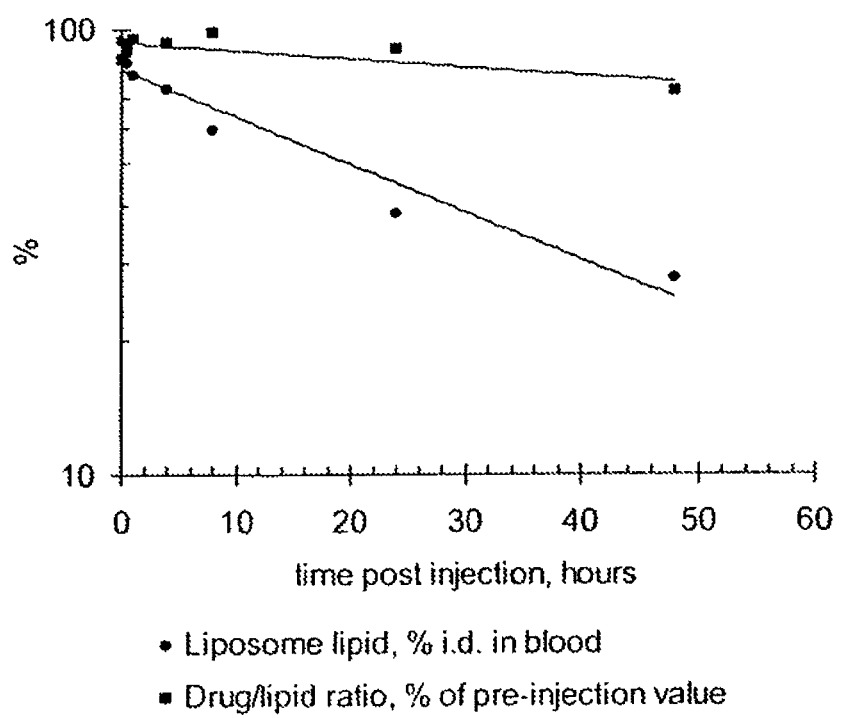
FIG. 36 shows blood pharmacokinetics of the liposome lipid and the dynamics of the drug/liposome lipid ratio in the blood of a rat after i.v. bolus administration of doxorubicin formulated into liposomes using triethylammonium sulfate method. (See Example 56).

Blood pharmacokinetics of these doxorubicin-containing liposomes having lipid composition of DSPC/Chol/PEG-DSPE 2.7:2:0.3 was studied in rats at a single i.v. dose of 5 mg doxorubicin/kg as described in Example 9. The liposomes were long circulating (half-life of about 28 hours) (FIG. 36). The stable doxorubicin-to-phospholipid ratio indicated that the formulation was remarkably stable against the drug leakage in the circulation, losing less than 25% of the drug over a 48-hour time period.

Example 57

Figure 37:
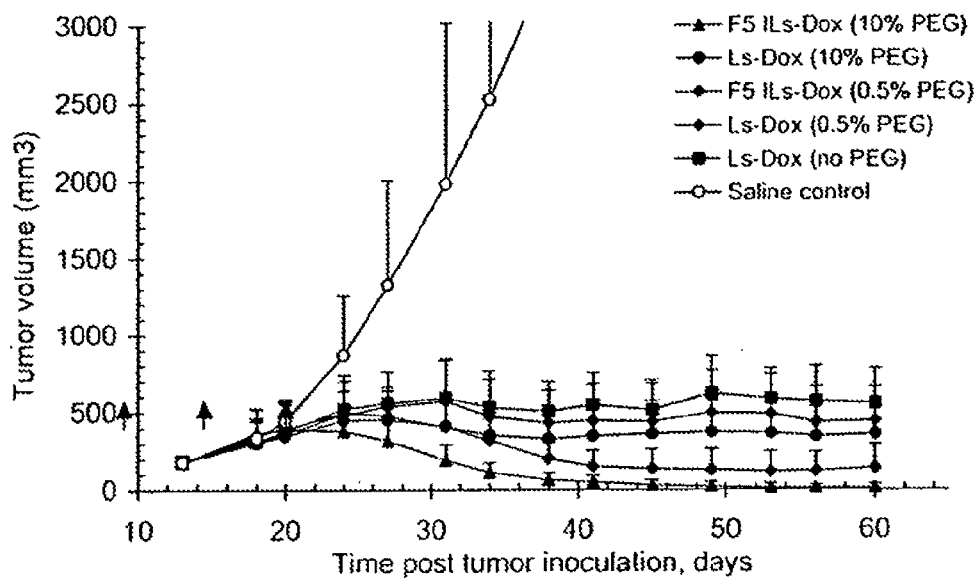
FIG. 37 shows antitumor efficacy of the liposomal doxorubicin (Ls-Dox), or scFv F5-conjugated, anti-HER2 immunoliposomal doxorubicin (F5 ILs-Dox) prepared using various amounts of PEG-lipid against HER2-overexpressing human breast carcinoma (BT-474) xenografts in nude mice. The on-panel caption shows the amount of PEG-lipid expressed in mol. % of liposome phospholipids. "Saline control" designates the mice treated with drug- and liposome-free vehicle only. (See Example 57).

Doxorubicin-Loaded Liposomes and Anti-HER2 Immunoliposomes Prepared by TEA-Sulfate Method: Preparation and In Vivo Antitumor Efficacy Against HER2-Overexpressing Human Breast Cancer Xenografts Doxorubicin-loaded liposomes having various lipid compositions and properties (listed in the table below) were prepared as described in Example 56. Doxorubicin-loaded anti-HER2 immunoliposomes were prepared from doxorubicin-loaded liposomes by co-incubation with anti-HER2 scFv F5-PEG-DSPE conjugate (approx. 30 scFv/liposome) as described in Example 19. NCR nu/nu mice bearing the subcutaneous human breast tumor xenograft (BT-474) were raised, treated (in groups of 10-12 animals) with liposomal or anti-HER2 immunoliposomal doxorubicin at a dose of 5 mg/kg once weekly for a total of three weeks once the tumors reached an average size of 200 mm$^3$, and the tumor progression and animal body weights were monitored as described in Example 29. For non-targeted doxorubicin liposome formulations, the lipid compositions containing no PEG-DSPE, 0.5 mol. % PEG-DSPE, or 10 mol. % PEG-DSPE, were studied; for F5-immunoliposomal doxorubicin, the formulations with 0.5 mol. % PEG-DSPE and 10 mol. % PEG-DSPE were studied (here the quantity of PEG-DSPE is expressed as mol. % of liposome phospholipid). The results (FIG. 37, Table 31) demonstrated that all doxorubicin treatments were effective in retarding the tumor growth. On the basis of tumor sizes at day 53 post inoculation, the differences in tumor growth inhibition among all three non-targeted liposome groups did not raise to statistical significance (ANOVA p=0.081), but the immunoliposome doxorubicin was significantly more efficacious than non-targeted liposomal doxorubicin)(ANOVAp=5.5×10$^{-10}$, the "10% PEG-DSPE" formulation being more efficacious than "0.5% PEG-DSPE" (Student's t-test, p=0.027). In the "10% PEG-DSPE" F5-ILs group, the tumors regressed to 1 mm$^3$ or less in 67% of animals, while in "0.5% PEG-DSPE" F5-ILs group only in 9%. In the control group (saline treatment) the tumors exceeded the acceptable size limit of 15% body weight at day 38-43.

TABLE 31

Liposomal doxorubicin in vivo antitumor efficacy study: liposome characteristics and treatment outcomes.

| Lipid composition | Liposome size, nm (mean ± SD) | drug/ phospholipid ratio, mg/mmol (mean ± SD) | Average tumor size at day 58, mm$^3$ (mean ± SEM) |
|---|---|---|---|
| DSPC/Chol/PEG-DSPE (3:2:0.015) | 83.4 ± 23.3 | 136.7 ± 6.7 | 490 ± 74 |
| DSPC/Chol (3:2) | 80.5 ± 26.6 | 151.2 ± 1.9 | 587 ± 61 |
| DSPC/Chol/PEG-DSPE (2.7:2:0.3) | 81.0 ± 24.7 | 140.1 ± 4.2 | 365 ± 60 |
| DSPC/Chol/PEG-DSPE (3:2:0.015) + F5 scFv-PEG-DSPE | not measured | 140.7 ± 2.8 | 119 ± 39 |
| DSPC/Chol/PEG-DSPE (2.7:2:0.3) + F5 scFv-PEG-DSPE | not measured | 132.9 ± 2.2 | 15.5 ± 7.6 |

Example 58

Preparation of Liposomal Vinblastine and Blood Pharmacokinetics of Liposomal Vinblastine in Rats Liposomes with entrapped aqueous TEA-SOS solution (0.65 M TEA, pH 6.4, osmolality 502 mmol/kg) and size 99.5±10.2 nm (mean±SD by QELS) were prepared by the method of Example 11 using extrusion 2 times through two stacked 0.2 μm polycarbonate membranes and ten times through two stacked 0.08 μm polycarbonate membranes. Vinblastine (VBL) in the form of vinblastine sulfate USP was added at a drug-to-phospholipid ratio of 150 mg/mmol. The pH of the drug-liposome mixture was adjusted to 6.5 using 1 N NaOH, and the mixture was subsequently incubated at 60° C. for 30 min. The reaction was then cooled on ice for 15 min and unencapsulated drug removed using Sephadex G-75 gel filtration chromatography, eluting with 5 mM HEPES-Na, 135 mM NaCl, pH 6.5. The purified liposomes were then analyzed for VBL spectrophotometrically and for phospholipid by Bartlett method as in Examples 70 and 71. [$^3$H]-CHE was included in the formulation at a ratio of 1.5 mCi/mmol phospholipid. The liposomal vinblastine had 152.4±12.0 mg VBL/mmol phospholipid (quantitative encapsulation).

Figure 38:
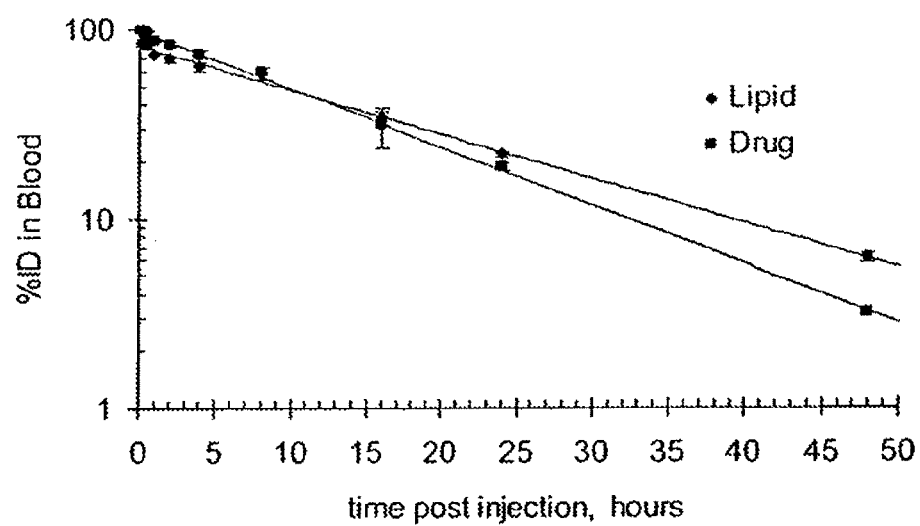
FIG. 38 shows blood pharmacokinetics of liposomal vinblastine in a rat. (See Example 58).
Figure 39:
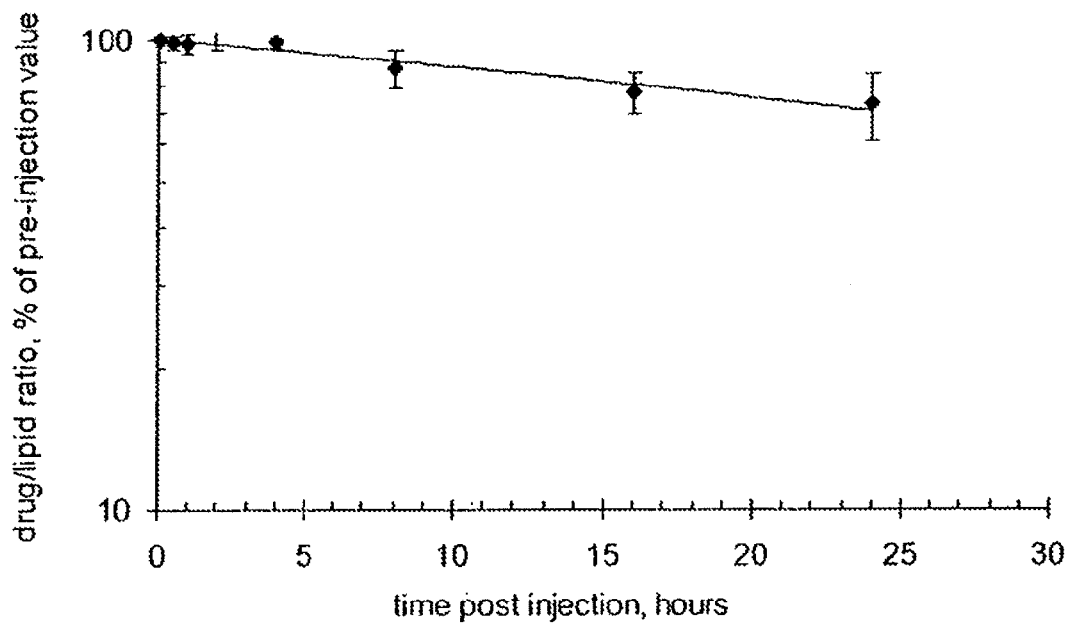
FIG. 39 shows the dynamics of the drug/liposome lipid ratio in the blood of a rat after i.v. bolus administration of liposomal vinblastine. (See Example 58).

Blood pharmacokinetics of the liposomal vinblastine in female Albino rats (8-9 weeks old; 200 g) at a dose of 5 mg VBL/kg was studied as described in Example 9. Vinblastine was quantified in blood plasma samples as described in Example 41 (using vinorelbine as internal standard). Vinblastine liposomes showed good circulation longevity (plasma half-life of the lipid component 12.8±0.04 hours) (FIG. 38) and very good stability against drug leakage from the liposomes with greater than 70% of the initial vinblastine load remaining encapsulated after 24 h (FIG. 39). The post-injection time to achieve release of 50% of the encapsulated drug was found to be 40.6±1.2 hours.

Example 59

Preparing Liposomes Loaded with Vincristine Using TEA-SOS Method and the Effect of pH on the Loading Efficiency Liposomes with the size of 86.6±12.9 nm (by QELS), lipid composition of DSPC/Chol/PEG-DSPE in the molar ratio of 3:2:0.015 and entrapped aqueous TEA-SOS solution (0.65 M TEA, pH 5.4, osmolality 521 mmol/kg) were prepared by the method of Example 11 using extrusion step of 15 passages through two stacked 0.08 μm pore size polycarbonate membranes. Vincristine (VCR) was added to the liposomes in 5 mM HEPES-Na, 5% dextrose aqueous buffer, pH 6.5, as vincristine sulfate at a drug-to-phospholipid ratio of 350 μg vincristine/mol phospholipid, the pH was adjusted to the indicated ratio using 1 N NaOH, the mixture was incubated at 60° C. for 30 min, chilled on ice for 15 min, and the liposomes were separated from unencapsulated drug using Sephadex G-75 gel filtration chromatography, eluting with HBS-6.5 (20 mM HEPES, 135 mM NaCl, pH 6.5). The purified liposomes were then analyzed for vincristine by spectrophotometry using absorbance at 265 nm after solubilization in acid isopropanol, and for the phospholipid content using the phosphate assay of Bartlett (1959).

The results are shown below in Table 32. The drug loading was in excess of 90% in the range of pH 4.5-7.5, and practically quantitative at pH 5.0-7.5. At pH 3.5, which is the pH observed in the liposome mixture after addition of the drug, but without pH adjustment, the loading was considerably lower.

TABLE 32 pH-Dependence of vincristine loading into liposomes with entrapped TEA-SOS.

| pH | Drug/phospholipid ratio, µg/µmol | Loading efficiency (%) |
|---|---|---|
| 3.5 | 39.7 ± 4.9 | 11.3 ± 0.2 |
| 4.5 | 327.2 ± 20.6 | 93.5 ± 5.4 |
| 5.0 | 360.6 ± 5.8 | 103.0 ± 1.7 |
| 5.5 | 371.2 ± 30.2 | 106.1 ± 9.1 |
| 6.0 | 347.7 ± 20.4 | 99.3 ± 5.8 |
| 6.5 | 347.7 ± 20.9 | 99.4 ± 5.9 |
| 7.0 | 377.3 ± 22.2 | 107.8 ± 6.8 |
| 7.5 | 371.5 ± 24.9 | 106.1 ± 7.6 |

Example 60

Preparing Liposomes Loaded with Vincristine Using TEA-SOS Method: Effect of the Drug/Lipid Ratio on the Loading Efficiency SOS-TEA-containing liposomes were prepared as in Example 59 and loaded with vincristine sulfate at a drug-to-phospholipid ratio of 150-550 µg vincristine/µmol phospholipid at pH 6.5 according to the procedure of Example 59. The liposomes purified from unencapsulated drug were then analyzed for VCR by spectrophotometry and for the liposome phospholipid using the assay of Bartlett (1959). The drug loading efficiency was in excess of 90% over the whole studied range of drug/lipid ratios, and was practically quantitative between 150-450 µg vincristine/µmol phospholipid (Table 33).

TABLE 33

Vincristine loading into liposomes containing TEA-SOS at different drug-to-lipid ratios.

| Input drug-to-phospholipid (µg/µmol) | Encapsulated drug-to-phospholipid (µg/µmol) | Loading efficiency (%) |
|---|---|---|
| 150 | 163.6 ± 6.6 | 109.0 ± 4.8 |
| 250 | 251.1 ± 17.0 | 100.5 ± 6.8 |
| 350 | 347.7 ± 20.9 | 99.4 ± 5.9 |
| 450 | 452.0 ± 18.8 | 100.4 ± 4.2 |
| 550 | 521.6 ± 24.9 | 94.8 ± 4.3 |

Example 61

Figure 40:
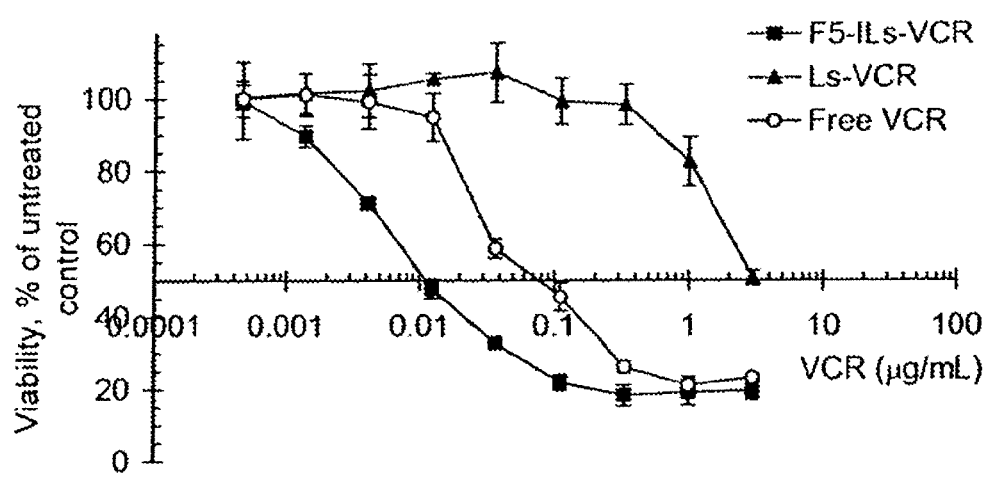
FIG. 40 shows the in vitro cytotoxicity of free vincristine (Free VCR), liposomal vincristine (Ls-VCR), or HER2-targeted immunoliposomal vincristine (F5-ILs-VCR) against HER2-overexpressing human breast cancer cells SKBr-3. (See Example 61).

Preparing Immunoliposomal Vincristine and Cytotoxicity of Liposomal and Immunoliposomal Vincristine Against Cancer Cells In Vitro Liposomal vincristine (Ls-VCR) was prepared as described in Example 59 using the drug/phospholipid ratio of 350 mg/mmol. HER2-specific F5-immunoliposomal vincristine (F5-ILs-VCR) was prepared from the liposomal vincristine by co-incubation with anti-HER2 scFv F5-PEG-DSPE conjugate as described in Example 19. "Free" vincristine (VCR) solution was prepared by dilution of vincristine sulfate USP in water, followed by sterile filtration. Cytotoxicity of VCR, Ls-VCR, and F5-ILs-VCR against HER2-overexpressing human breast carcinoma cells SKBr-3 (ATCC) was determined by MTT-based cell viability assay using the procedure of Example 27, wherein the cells were inoculated into 96-well microtiter plates at 5,000 cells/well, acclimated overnight, and incubated with the drug-containing media for 4 hours, followed by post-incubation in a drug-free medium for 3 days. The results are shown on FIG. 40. The $IC_{50}$ was 75 ng/ml for free VCR, 11 ng/ml for F5-ILs-VCR, and 3 µg/ml for Ls-VCR. The targeted liposomal vincristine prepared according to the invention was 6.8 times more active than the free drug, and 273 times more active than non-targeted liposomal drug, showing substantial enhancement in anticancer activity as a function of cell-specific drug delivery.

Example 62

Blood Pharmacokinetics of Ls-VCR in Rats

Figure 41:
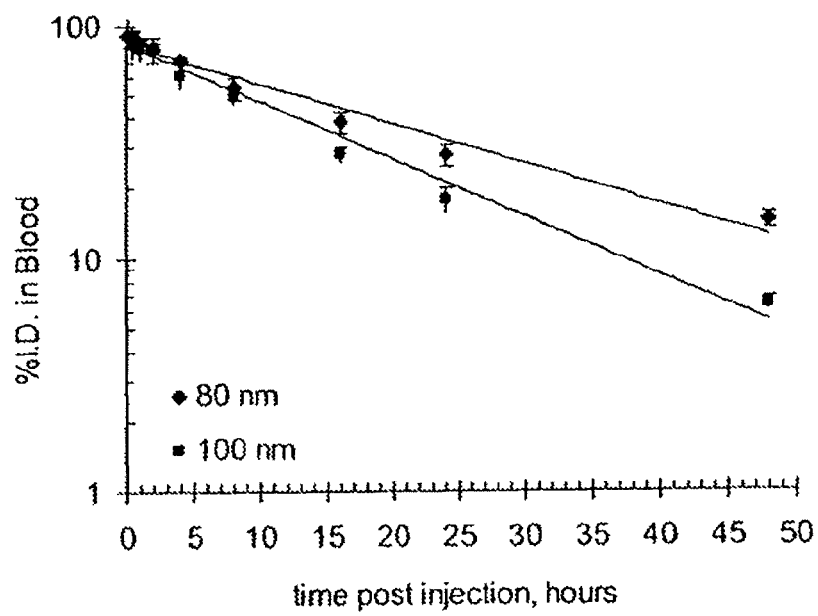
FIG. 41 shows blood pharmacokinetics of the liposome lipid in a rat after i.v. bolus administration of vincristine formulated into liposomes of different average size (indicated on the on-panel caption). (See Example 62).
Figure 42:
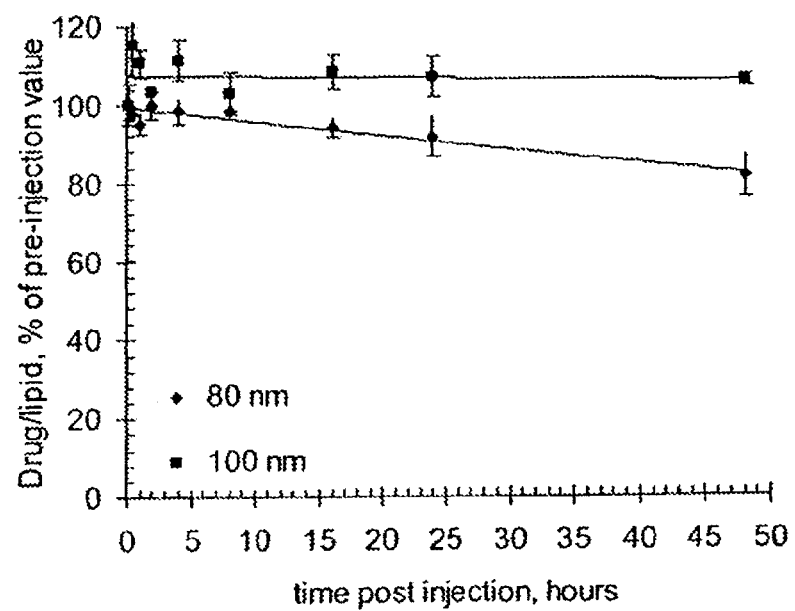
FIG. 42 shows the dynamics of the drug/liposome lipid ratio in the blood of a rat after i.v. bolus administration of vincristine formulated into liposomes of different average size (indicated on the on-panel caption). (See Example 62).

Liposomes with entrapped SOS-TEA solution (0.65 M TEA, pH 5.8, osmolality 530 mmol/kg), and lipid composition of DSPC/Chol/PEG-DSPE (molar ratio 3:2:0.015), also containing [$^3$H]-CHE at 1.5 mCi/mmol phospholipid, were prepared by the method of Example 11 using extrusion step of 10 passages through two stacked polycarbonate membranes with the pore size of 80 nm or 100 nm. The liposomes were loaded with VCR at pH 6.5, drug/phospholipid ratio of 350 mg/mmol, as described in Example 59. The VCR-loaded liposomes were administered i.v. to female albino rats (180-220 g) at a dose of 5 mg VCR/kg, and the blood pharmacokinetics of the drug and the liposome lipid was studied as described in Example 9. The amount of VCR in the blood samples was quantified by HPLC as described in Example 41, except that the volume ratio of aqueous triethylammonium acetate (pH 5.5) and acetonitrile in the mobile phase was 65:35. The typical retention time for VCR was 8.8 min. The results are shown in FIG. 41 and Table 34. Both preparations had extensive circulation longevity (blood half-lives of 12-17 hours). Liposomal vincristine was remarkably stable against drug leakage in both preparations (half-release time over 120 hours) (FIG. 42).

TABLE 34

Characteristics of liposomes loaded with vincristine at 350 mg/mmol phospholipid using TEA-SOS method.

| Extrusion pore size, nm | Liposome size, nm (mean ± SD) | Drug load, mg/mmol phospholipid | $t_{1/2\beta}$ lipid, hours | $t_{1/2\beta}$ VCR, hours | $t_{1/2}$ VCR release, hours |
|---|---|---|---|---|---|
| 80 | 101.2 ± 20.2 | 347.7 ± 20.93 | 17.5 ± 1.5 | 16.0 ± 2.0 | >120 |
| 100 | 125.6 ± 32.0 | 366.8 ± 18.11 | 12.1 ± 0.7 | 12.0 ± 0.8 | Not detectable |

Example 63

Blood Pharmacokinetics of Ls-VCR in Rats at Various Drug/Lipid Ratios

Liposomes with entrapped SOS-TEA solution (0.65 M TEA, pH 6.4, osmolality 485 mmol/kg), and lipid composition of DSPC/Chol/PEG-DSPE (molar ratio 3:2:0.015) also containing [$^3$H]-CHE at 1.5 mCi/mmol phospholipid were prepared by the method of Example 11 using extrusion step of 10 passages through two stacked polycarbonate membranes with the pore size of 50 nm or 80 nm. The liposomes were loaded with VCR at pH 6.5 as described in Example 59 by adding a stock 20 mg/mL aqueous VCR sulfate solution at the calculated drug/lipid ratios of 100, 200, or 350 mg/mmol phospholipid. The efficiency of drug loading was over 96% for all preparations. The VCR-loaded liposomes were administered i.v. to female albino rats (8-9 week old, 190-220 g) at a dose of 5 mg VCR/kg, and the blood pharmacokinetics of the drug and the liposome lipid was studied as described in Example 62. The results are shown in Table 35. Liposomal vincristine had good circulation longevity (blood half-life of the drug about 20-30 hours) and was exceptionally stable at all studied sizes and drug-to-lipid ratios (half-life of drug release over 93 hours).

TABLE 35

Characteristics of liposomes loaded with vincristine using TEA-SOS method at various drug/lipid ratios.

| Extrusion pore size, nm | Liposome size, nm (mean ± SD) | VCR, mg/mmol phospholipid added | VCR, mg/mmol phospholipid encapsulated | $t_{1/2}$ lipid, hours | $t_{1/2}$ VCR, hours | $t_{1/2}$ drug release, hours |
|---|---|---|---|---|---|---|
| 50 | 76.8 ± 27.2 | 100 | 96.1 ± 3.0 | 35.6 ± 2.7 | 30.3 ± 4.0 | 227 ± 96 |
|  |  | 200 | 193.3 ± 3.9 | 20.8 ± 2.2 | 18.4 ± 0.7 | 244 ± 130 |
|  |  | 350 | 375.2 ± 10.0 | 24.8 ± 0.9 | 19.6 ± 0.9 | 93.2 ± 6.7 |
| 80 | 101.6 ± 25.3 | 100 | 104.5 ± 2.1 | 33.0 ± 7.6 | 26.8 ± 4.8 | 153 ± 10 |

Example 64

Figure 43:
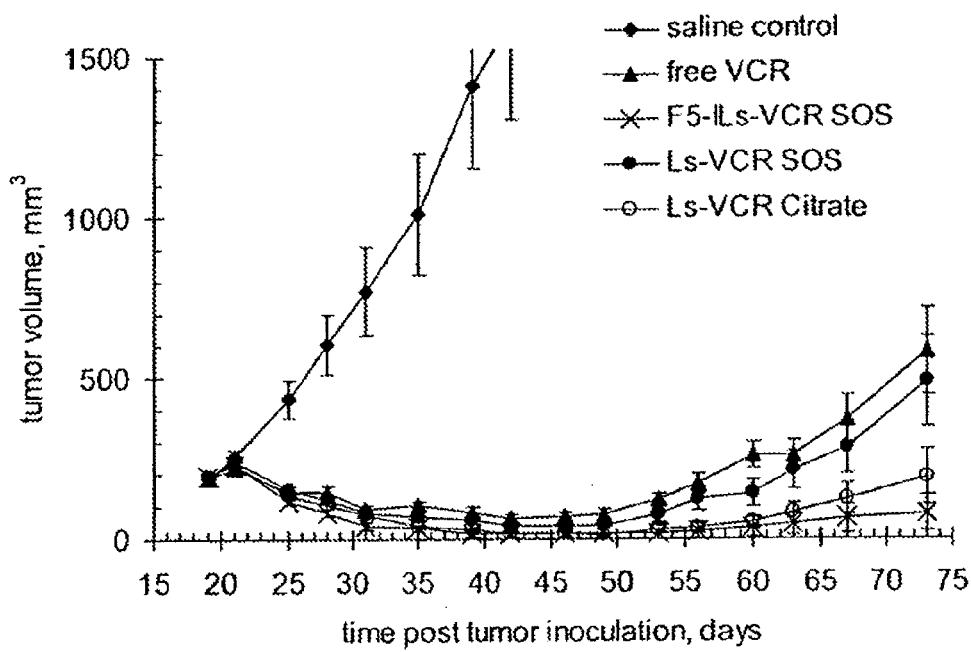
FIG. 43 shows antitumor efficacy of the free vincristine (free VCR), liposomal vincristine prepared by triethylammonium citrate method (Ls-VCR Citrate), liposomal vincristine prepared by triethylammonium sucrooctasulfate method (Ls-VCR SOS), or scFv F5-conjugated, anti-HER2 immunoliposomal vincristine prepared by triethylammonium sucrooctasulfate method (F5 ILs-VCR SOS) against HER2-overexpressing human breast carcinoma (BT-474) xenografts in nude mice. "Saline control" designates the mice treated with drug- and liposome-free vehicle only. (See Example 64).
Figure 44:
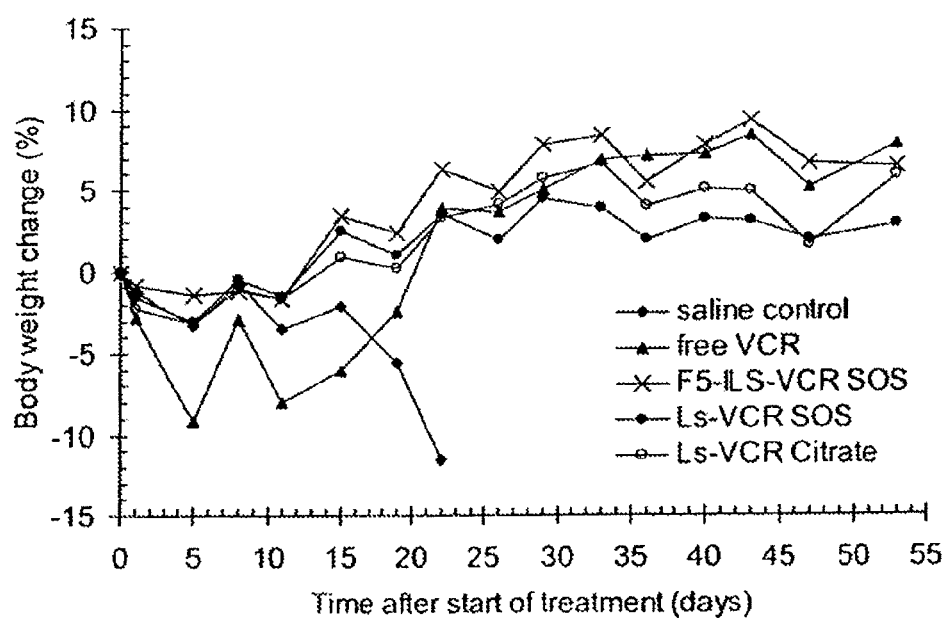
FIG. 44 shows the dynamics of the average body weights during the treatment of mice bearing HER2-overexpressing human breast carcinoma (BT-474) xenografts with free vincristine (free VCR), liposomal vincristine prepared by triethylammonium citrate method (Ls-VCR Citrate), liposomal vincristine prepared by triethylammonium sucrooctasulfate method (Ls-VCR SOS), scFv F5-conjugated, anti-HER2 immunoliposomal vincristine prepared by triethylammonium sucrooctasulfate method (F5 ILs-VCR SOS), or with vehicle only (saline control). (See Example 64).

Preparation of HER2-Targeted Liposomal Vincristine and Antitumor Efficacy of Non-Targeted and HER2-Targeted Liposomal Vincristine Against HER2-Overexpressing Human Breast Cancer Xenografts in Mice Vincristine-loaded liposomes (Ls-VCR-SOS) using TEA-SOS method were prepared according to Example 63 (with omission of [$^3$H]-CHE component) using 50 nm pore size membrane extrusion and drug loading at drug/phospholipid ratio of 100 mg/mmol. F5 immunoliposomal vincristine (F5-ILs-VCR) was formed by incubating Ls-VCR-SOS with anti-HER2 scFv F5-PEG-DSPE conjugate (Example 19) as described in Example 43. Vincristine-loaded liposomes using TEA-citrate (Ls-VCR-Cit) were prepared similarly to Ls-VCR-SOS liposomes, except that triethylammonium citrate solution (prepared by titrating aqueous citric acid with neat triethylamine to pH 5.1 and adjusting the concentration to 0.65 M triethylamine) was substituted for TEA-SOS solution. The treatment study design followed the method of Example 10. Subcutaneous xenograft tumors of BT-474 human breast carcinoma were raised in nude mice, and when the tumors reached the size of 250 mm$^3$ (range 144-309 mm$^3$) the mice in the groups of eight to nine, were treated with free VCR, Ls-VCR, or F5-ILs-VCR at a weekly i.v. dose of 2 mg VCR/kg for a total of three weeks, starting at day 19 post tumor inoculation. The tumor sizes and animal body weights were monitored as described in Example 10. For the control group, mice were treated with an equal volume of saline. The differences in tumor sizes between the treatment groups were statistically assessed at day 63 post tumor inoculation using Mann-Whitney test. The dynamics of average tumor size in the groups is shown in FIG. 43. F5-ILs-VCR demonstrated maximum efficacy when compared to either Ls-VCR or free VCR, causing at day 63 complete tumor regressions in six out of eight animals (75%). Ls-VCR-Cit was also effective, causing complete tumor regressions still observed at day 63 in two out of nine animals (22%), however, it was less effective than F5-ILs-VCR (p<0.005). Ls-VCR-SOS and free VCR were equally effective (p>0.2) and less effective than either F5-ILs-VCR or Ls-VCR-Cit. Thus, surprisingly, with cell-targeted delivery, a liposomal drug encapsulated using a polyvalent anion of the present invention proved more efficacious than the drug liposomally encapsulated via non-binding anion. Animal body weight dynamics showed that all liposomal VCR preparations were less toxic than free VCR, causing less body weight loss during treatment (FIG. 44).

Example 65

Preparation of EGFR-Targeted Liposomal Vincristine and Antitumor Efficacy of Non-Targeted and EGFR-Targeted Liposomal Vincristine Against EGFR-Overexpressing Human Brain Cancer Xenografts in Mice Vincristine-loaded liposomes (Ls-VCR) were prepared using TEA-SOS method as in Example 64. EGFR-targeted immunoliposomal vincristine was prepared by co-incubation of the liposomes with anti-HER2 Fab' C225Fab-PEG-DSPE conjugate as described in Example 36.

Figure 45:
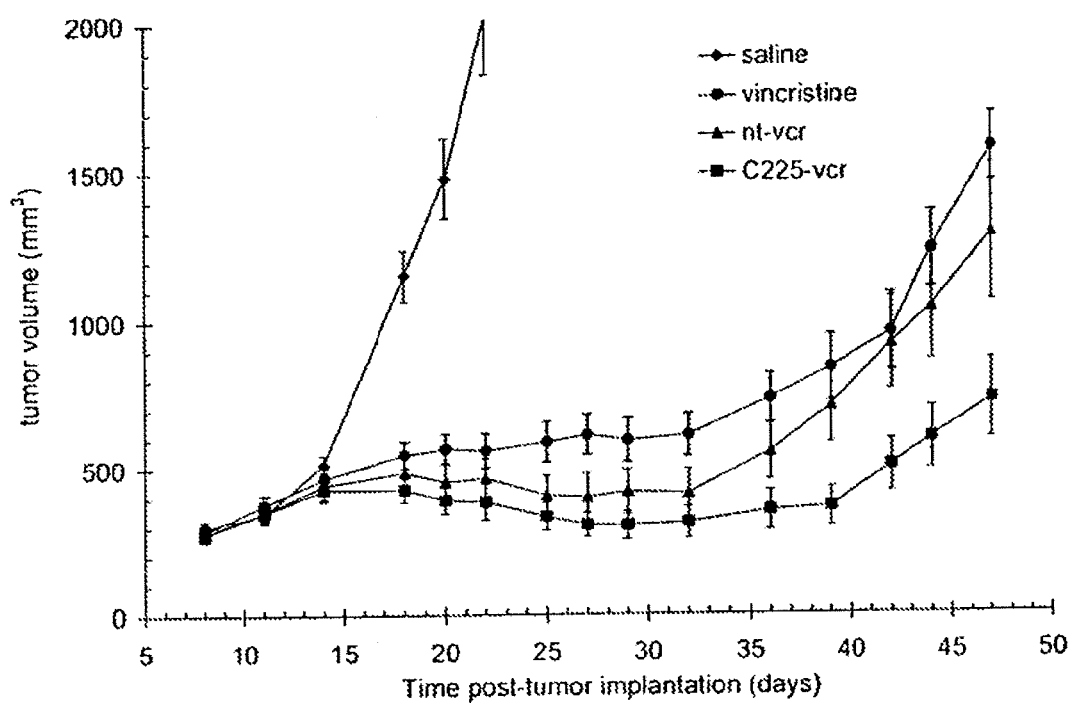
FIG. 45 shows antitumor efficacy of the free vincristine (vincristine), liposomal vincristine (nt-vcr), or C225 Fab'-conjugated, anti-EGFR immunoliposomal vincristine (C225-vcr) against EGFRvIII-overexpressing human brain cancer (U87) xenografts in nude mice. "Saline" designates the mice treated with drug- and liposome-free vehicle only. (See Example 65).

Male NCR nu/nu mice (5-6 week old, weighing 17-20 g) were injected subcutaneously in the flank area with 0.15 ml of the cell growth medium containing 1×10$^7$ U87 human glioblastoma cells stably expressing epidermal growth factor receptor (HER1) mutant EGFRvIII. At day 11 when the mean tumor size reached 300-400 mm$^3$, the mice were randomly divided into four groups of 10-12 animals/group. Treatments with free VCR (vincristine sulfate 1 mg/mL in saline), Ls-VCR, or C225Fab-ILs-VCR at i.v. dose of 1.5 mg/kg were administered on days 11, 18, and 25 post tumor inoculation. Mice in the control group were similarly injected with an equal volume of normal saline. The tumor sizes and mouse body weights were monitored as in Example 10. The results are shown in FIG. 45. All animals treated with VCR formulations showed retardation of tumor growth compared to control animals. There was no significant difference between the groups treated with free VCR and Ls-VCR. EGFR-targeted C225Fab-ILs-VCR was more efficacious than free or non-targeted liposomal VCR.

Example 66

Preparation of Liposomes with Entrapped Triethylammonium Inositol Hexaphosphate (TEA-IHP) Solution A polyanionized polyol, inositol hexaphosphate (IHP) dodecasodium salt, was obtained from Sigma (St. Louis, Mo.). Aqueous solution containing 0.65 M triethylammonium and 0.681 M of phosphate groups, pH 6.5, and osmolality of 718 mmol/kg, was prepared by ion-exchange on the Dowex 50W×8-200 cross-linked sulfonated polystyrene resin followed by titration with neat TEA and dilution with water according to the procedure of Example 4. The residual sodium content was less than 1% of the sum of cations. Dry lipids (150 μmol DSPC, 100 μmol Chol, 0.75 μmol PEG-DSPE) were dissolved in 0.5 ml of 100% ethanol USP at 60° C. and mixed with 4.5 ml of triethylammonium inositol hexaphosphate solution pre-heated to the same temperature. The ethanol was partially removed by rotary evaporation at 30-40 mm Hg and 40-45° C. until the mixture showed no bubbling. The lipid suspension was then extruded at 60-65° C. 15 times through two stacked 0.1 μm pore size polycarbonate membranes. The resulting liposomes were 104.3±39.0 nm in size by QELS. The unencapsulated triethylammonium IHP was removed by gel chromatography on a Sepharose 4B column, eluted with 5 mM HEPES-Na, 5% dextrose, pH 6.5 buffer, and the liposomes were quantified by phospholipid concentration using Bartlett's method with extraction according to Example 70.

Example 67

Loading of Drugs into Liposomes with Entrapped TEA-IHP Solution

The liposomes of Example 67 were loaded with CPT11 or vinorelbine Vinorelbine was loaded at a drug-to-phospholipid ratio of 175 or 350 g/mol, and CPT11 at a ratio of 250 or 500 g/mol. The drugs were added to the liposomes in the HEPES-dextrose buffer (Example 67) at the input drug/phospholipid ratios, indicated below (see Table 36). If necessary, the pH was adjusted to 6.5-6.8 using 1 N NaOH. The mixtures were incubated at 60° C. for 30 min, cooled down on ice for 15 min, and chromatographed on a Sephadex G-25 gel filtration column, eluted with 5 mM HEPES-Na, 145 mM NaCl, pH 6.5. Aliquots of the purified liposomes were solubilized in acidified methanol and analyzed by spectrophotometry (Example 71). Phospholipid was quantified by the method of Bartlett (1959) with extraction (Example 70). Both drugs loaded quantitatively (i.e., practically 100%) into the liposomes, as shown below in Table 36.

TABLE 36

Properties of drugs loaded into liposomes with entrapped inositol hexaphosphate.

| Drug | Input drug/lipid ratio, g/mol phospholipid | Encapsulated drug/lipid ratio, g/mol phospholipid | Loading efficiency, % |
|---|---|---|---|
| Vinorelbine | 175 | 175.3 ± 8.0 | 100.2 ± 4.5 |
| Vinorelbine | 350 | 352.3 ± 11.8 | 100.6 ± 3.3 |
| CPT-11 | 250 | 265.1 ± 11.2 | 106.1 ± 4.7 |
| CPT-11 | 500 | 518.7 ± 27.8 | 103.7 ± 5.8 |

Example 68

Chemical Stability of Free or Liposomal CPT-11 in the Presence of Mouse Plasma In Vitro In the body, CPT-11, which is a pro-drug, undergoes chemical transformation to form an active drug metabolite known as SN-38. Both SN-38 and CPT-11 are also converted from their active lactone forms into an inactive products known as a SN-38 or CPT-11 carboxylates. In this Example the effect of liposomalization of CPT-11 in accordance with the present invention on the CPT-11 chemical conversion into these products in the presence of blood plasma was studied. Liposomes with entrapped triethylammonium sucroseoctasulfate (0.65 M TEA, pH 6.4, osmolality 485 mmol/kg) and lipid composition of DSPC, Cholesterol, and PEG-DSPE in a molar ratio of 3:2:0.015 were prepared according to Example 11, using extrusion ten times through two stacked 0.08 μm polycarbonate filters. The liposomes were 87.4±19.2 nm in size by QELS. CPT-11 was loaded at approximately 500 mg of CPT-11 base/mmol liposome phospholipid by incubation in an aqueous 5 mM HEPES-Na, 5% dextrose, pH 6.5, at 60° C. for 30 min., followed by quenching on ice for 15 min. The CPT-11-loaded liposomes were then purified on a Sephadex G-75 column eluted with HEPES buffered saline (5 mM HEPES, 145 mM NaCl, pH 6.5). The resulting CPT-11 liposomes had 536.5±20.1 mg CPT-11/mmol of phospholipid. Free CPT-11 solution was prepared by freshly dissolving Irinotecan Hydrochloride USP at 1 mg/ml in 144 mM aqueous NaCl, acidified to pH 3 with diluted HCl. Ten-μl aliquots of free or liposomal CPT-11 or free CPT-11 were mixed with 90 μl of heparin-stabilized mouse plasma (Harlan Bioproducts, USA) and incubated at 37° C. in a shaking water bath. At a given time point liposome samples, in triplicate, were chromatographed on Sepharose CL-4B size exclusion columns (2 ml bed volume) eluted with HBS-6.5, and the drug-containing fractions were detected by fluorescence. The first (void volume) and second (trailing) drug-containing peaks were collected and considered as the liposomally encapsulated and released drug fractions. The samples were extracted with 400 of ice-cold methanol by vortexing for 10 s followed by centrifugation at 14,100×g for 5 min. The supernatants were analyzed for CPT-11 and its conversion products by HPLC using modification of a method by Warner and Burke, *J Chromatogr., Ser. B Biomed. Sci. Appl.* 1997, vol. 691, p. 161-71. The mobile phase consisted of 3% triethylammonium acetate pH 5.5 (solution A) and acetonitrile (solution B) delivered at 1.0 ml/min in a linear gradient of 20 vol % B to 50 vol. % B in 14 min. The eluted products were detected by fluorescence with an excitation at 375 nm and emission at 500 nm. The retention times were 5.3 min (CPT-11 carboxylate), 6.8 min (SN-38 carboxylate), 9.3 min (CPT-11) and 11.0 min (SN-38). The results (Table 37) indicated that while free CPT-11 and CPT-11 released from the liposomes underwent conversion, intraliposomal CPT-11 was quite stable.

TABLE 37

Conversion of free and liposomal CPT-11 into SN-38 and carboxylate forms in mouse plasma in vitro.

| | | CPT-11, % | | SN-38, % | |
|---|---|---|---|---|---|
| Sample | Time, hours | lactone | carboxylate | lactone | carboxylate |
| Free CPT-11 | 2 | 1.9 ± 0.4 | 35.2 ± 1.9 | 4.4 ± 0.1 | 58.4 ± 2.1 |
| | 12 | <0.1 | 11.5 ± 0.9 | 9.9 ± 0.8 | 78.6 ± 1.3 |
| | 24 | <0.1 | <0.1 | 22.5 ± 9.8 | 77.5 ± 9.8 |
| Ls-CPT-11 (encapsulated) | 12 | 97.7 ± 0.1 | <0.1 | 2.3 ± 0.1 | <0.1 |
| | 24 | 97.7 ± 0.1 | <0.1 | 2.3 ± 0.1 | <0.1 |
| Ls-CPT-11 (released) | 12 | 60.5 ± 10.4 | 25.0 ± 7.1 | 5.0 ± 0.3 | 9.5 ± 3.0 |
| | 24 | 78.3 ± 6.7 | 14.0 ± 5.2 | 6.5 ± 0.5 | 1.2 ± 1.7 |

Example 69

In Vivo Chemical Stability of Free or Liposomal CPT-11 in Rats

Figure 46:
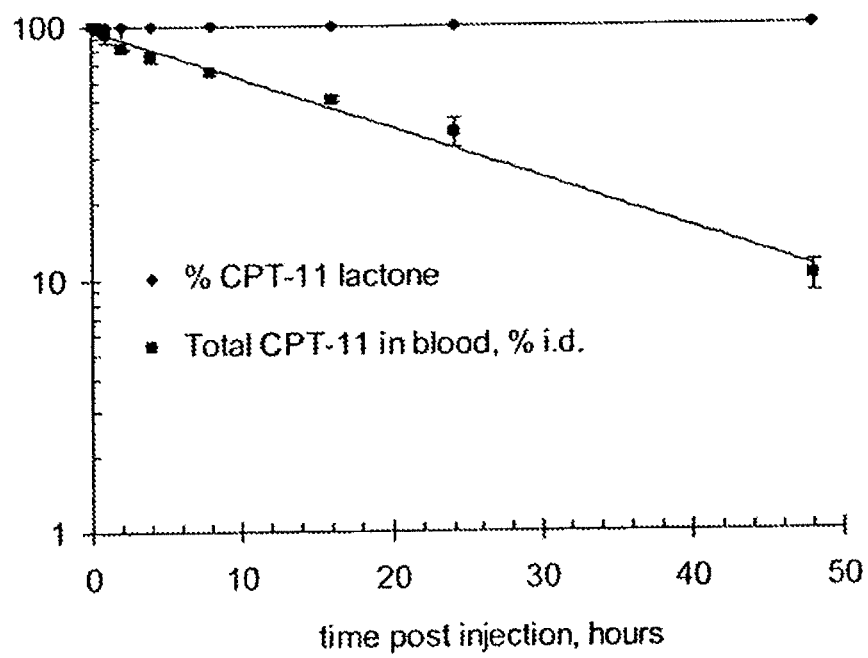
FIG. 46 shows blood pharmacokinetics of CPT-11 and the dynamics of the percentage of CPT-11 present in the active (lactone) form in the blood of a rat after i.v. bolus administration of liposomal CPT-11. (See Example 69).
Figure 47:
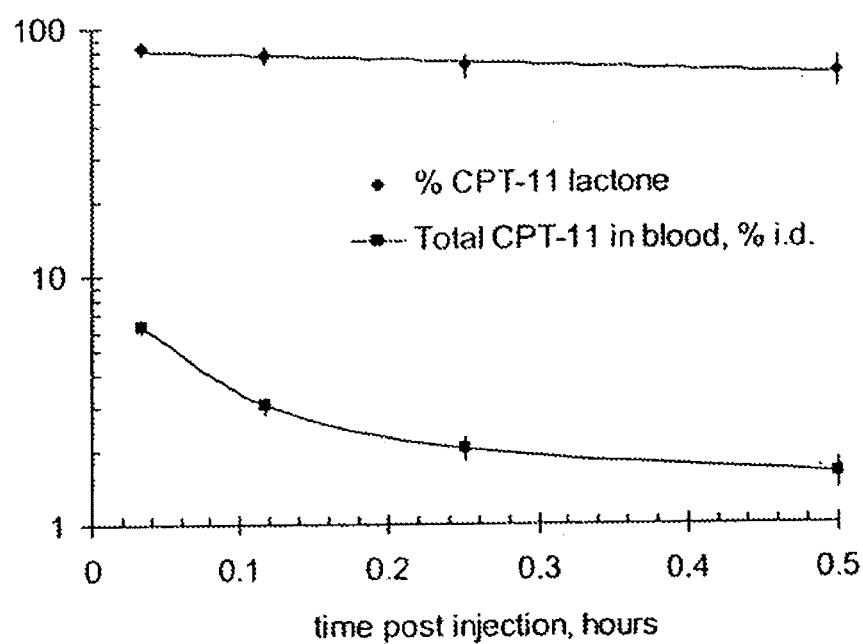
FIG. 47 shows blood pharmacokinetics of CPT-11 and the dynamics of the percentage of CPT-11 present in the active (lactone) form in the blood of a rat after i.v. bolus administration of CPT-11 solution (free CPT-11). (See Example 69).

Liposomal CPT-11 was prepared as in Example 68 using triethylammonium sucroseoctasulfate having 0.65 M TEA, pH 6.4, and osmolality 502 mmol/kg. The liposome size was 98.5±18.4 nm, and CPT-11 encapsulation was 510.1±16.5 mg CPT-11/mmol phospholipid. The liposomal and free CPT-11 was administered intravenously at the dose of 25 mg/kg into female Albino rats (180-220 g) with indwelling central venous catheters, and the blood samples were withdrawn at intervals over the period of 48 hours. The blood samples were mixed with ice-cold PBS containing 0.04% EDTA and quickly centrifuged to remove blood cells. Aliquots of the supernatant fluids were assayed for CPT-11, SN-38, and their carboxylate forms by HPLC as in Example 68 above. The results are shown in FIGS. 46 and 47. Whereas the free CPT-11 was cleared very rapidly, being undetectable after 30 min, the liposomal CPT-11 was persistent in the circulation ($t_{1/2}$ 15.2 hours) with 37.8% of the drug in the blood at 24 h, and approximately 10% of the drug still in the circulation after 48 h. There was no detectable conversion of the liposomal form of CPT-11 to either SN-38 or the carboxylate form of CPT-11. Free CPT-11, i.e. administered as a solution, cleared from the circulation quite fast (half-life of about 16 min), and there was appreciable conversion to the carboxylate form of the drug.

Example 70

Quantification of the Liposome Phospholipid

Modified acid digestion—blue phosphomolybdate method I. This method is modified after Bartlett (1959). 10-20 ml aliquots of liposomes are placed into heat-resistant glass tubes, digested by heating with 0.5 ml of 10 N sulfuric acid for 2 hours at 110-130° C., mineralized by addition of 50 ml of 9% hydrogen peroxide, and heated for additional 30 min. until no hydrogen peroxide is detected by an indicator paper strip. The digested samples at ambient temperature are diluted with 1 ml of 0.2% aqueous ammonium molydbate, mixed with 0.1 ml of 5% aqueous ascorbic acid, and incubated on a boiling water bath for 10 min. The absorbance of reduced phosphomolybdate complex is measured at 800 nm and compared to a standard curve concurrently produced using inorganic phosphate standard solutions.

Modified acid digestion—blue phosphomolybdate method II. This method is a modification of the method by Morrison (1964). 5 µl aliquots of liposomes having 1-10 mM phospholipid are mixed with 60 µl of concentrated sulfuric acid and 10 µl of 30% hydrogen peroxide in heat-resistant glass tubes. The mixtures are heated at 200-220° C. for 10 min., diluted with 0.7 µl of deionized water, mixed with 10 µl of 10% aqueous sodium sulfite, incubated on a boiling water bath for 5 min, and chilled down to ambient temperature. 200 µl of 2% aqueous ammonium molybdate and 10 µl of 10% aqueous ascorbic acid are added, and the samples are incubated on a boiling water bath for 10 min. Samples are quickly chilled to ambient temperature, and the absorbance of reduced phosphomolybdate complex is determined at 825 nm against the blank sample. The amount of phospholipid is determined from the standard curve obtained in the same run using standard solutions having 2, 4, 6, 8, and 10 mM potassium dihydrogen phosphate.

Extraction Method. 25-100 µl aliquots of liposomes are extracted 3 times with 200 µl portions of methanol-chloroform mixture (1:2 by volume). The organic phases are combined in a heat-resistant glass tube, and the solvents are removed in vacuum. The residues are treated with 10N sulfuric acid and further assayed for phosphorus according to the method I above.

Unless indicated otherwise, the analytical data are presented as the mean±standard error of triplicate runs.

Example 71

Quantification of Drugs in the Liposomes

Spectrophotometric quantification. Aliquots of liposomes (10-50 µl) are mixed with 1 mL of 70 vol. % aqueous isopropanol containing 0.075-0.1 N HCl, and the absorbance against the blank sample is measured at the following wavelengths: doxorubicin, 485 nm; CPT-11 and topotecan, 372 nm; ellipticines, 306 nm, vinorelbine, 270 nm; vincristine and vinblastine, 265 nm. The amount of drug is determined by comparison to a concurrently run standard curve.

Fluorometric quantification. Aliquots of liposome-containing samples (e.g., blood plasma) are diluted with acidified isopropanol (0.02-0.1 ml aliquots: 1 mL of 70% isopropanol-0.075 N HCl; >0.1 ml aliquots: 90% isopropanol-0.1 N HCl to 1 mL). If protein precipitation occurs, the samples are incubated on ice 1-2 hours and clarified by centrifugation 10 min at 12,100×g. The fluorescence of the supernatants is measured at the following wavelengths: CPT-11, excitation 370 nm, emission 423-425 nm; Topotecan, excitation 380-385 nm, excitation 520-525 nm; ellipticines, excitation 306 nm, emission 520 nm. The amount of drug is calculated from concurrently run standard curves after subtraction of the blank fluorescence.

Example 72

Effect of Lipopolymers on the Loading Efficiency of Vinorelbine into Liposomes Liposomes composed of DSPC 200 molar parts, cholesterol 133 molar parts, and poly(ethylene glycol)(mol. weight 2,000)-derivatized lipids PEG-DSPE (1-20 molar parts) or PEG-DSG (20 molar parts), and containing encapsulated 0.65 M TEA-SOS solution were prepared according to the method of Example 11, using 80 nm pore size membrane for extrusion step. The liposomes were loaded with vinorelbine at the drug/phospholipid ratio of 350 mg/mmol and purified from unencapsulated drug according to the method of Example 40. The liposomes were assayed for drug and lipid content as described in Examples 70, 71, and for the liposome size by QELS using volume-weighted Gaussian approximation. The results (Table 38) indicated that while anionic PEG derivative, PEG-DSPE, at the amount of more than 1 mole % of the liposome phospholipid (0.3 mole % of the total lipid), had negative effect on the drug loading efficiency, the neutral derivative, PEG-DSG, surprisingly, did not affect the loading efficiency even at 9.1 mole % of the liposome phospholipid (5.7 mole % of total lipid).

TABLE 38

Properties of vinorelbine liposomes prepared by TEA-SOS method at various amounts of PEG-lipid derivatives.

| PEG-lipid | PEG-lipid amount, mol. % of total lipid | Liposome size, nm (mean SD) | Drug load, mg/mmol phospholipid | Loading efficiency, % encapsulation |
|---|---|---|---|---|
| PEG-DSPE | 0.3 | 108 ± 32 | 359.5 ± 17.8 | 102.7 ± 5.2 |
| PEG-DSPE | 0.6 | 110 ± 18 | 346.6 ± 14.5 | 99.0 ± 4.1 |
| PEG-DSPE | 1.8 | 104 ± 35 | 332.0 ± 14.0 | 94.9 ± 3.8 |
| PEG-DSPE | 2.9 | 94 ± 33 | 259.8 ± 9.5 | 74.2 ± 2.0 |
| PEG-DSPE | 4.0 | 100 ± 36 | 155.4 ± 7.0 | 44.4 ± 0.9 |
| PEG-DSPE | 5.7 | 103 ± 31 | 61.2 ± 5.2 | 17.5 ± 0.3 |
| PEG-DSG | 5.7 | 97 ± 36 | 362.7 ± 14.2 | 103.6 ± 4.2 |

Example 73

Effect of Intraliposomal Drug-Trapping Agent on the Blood Longevity of CPT-11 in Mice Liposomes with entrapped 0.65 N solutions of triethylammonium (TEA) or triethanolammonium (TEOA) salts of inositol hexaphosphate (IHP, phytic acid) or sucrose octasulfate were prepared and loaded with CPT-11 at 500 g/mol phospholipid following general procedure of Example 66. The liposomes were administered intravenously to Swiss-Webster mice in the dose of 5 mg CPT-11/kg body weight. Twenty four hours later, the mice were anesthetized, and exsanguinated via open heart puncture. The blood was collected, analysed for CPT-11 content in the blood plasma by HPLC as described in Example 68, and the drug amount was expressed as % of injected dose remaining in the blood (% ID). TEOA-IHP was less effective in improving the blood longevity of the drug than TEA-IHP, TEOA-SOAS, and TEA-SOS (Table 39).

TABLE 39

CPT-11 remanence in the blood 24 hours following intravenous administration of CPT-11 liposomes in mice.

| Intraliposomal drug-trapping agent | % ID remaining in the blood |
|---|---|
| TEOA-IHP | 2.74 ± 0.54 |
| TEA-IHP | 5.86 ± 0.20 |
| TEOA-SOS | 7.03 ± 0.17 |
| TEA-SOS | 11.32 ± 0.46 |

Example 74

Drug Loading into Liposomes Containing 1.05 N Diethylammonium Sucrose Octasulfate Aqueous solution of 1.05 N diethylammonium sucrose octasulfate (DEA-SOS) pH 6.0, osmolarity 727 mmol/kg, was prepared using ion-exchange/titration method of Example 6 using neat diethylamine (99.5% purity). The lipid matrix of 3 molar parts DSPC, 2 molar parts Cholesterol, and 0.015 molar parts PEG2000-DSPE, was formulated into liposomes (volume-weighted average size 92.4 nm) in the presence of DEA-SOS solution, and CPT-11 was loaded in the liposomes as various drug/lipid input ratios using the method of Example 11. Non-encapsulated drug was removed by gel-chromatography, and the amount of encapsulated drug per unit lipid (drug/lipid output ratio) was determined. Encapsulation efficiency was calculated as % of drug/lipid output ratio relative to input ratio. The results are shown in Table 40. The loading achieved it's maximum level of about 1.76 mol drug per mol phospholipid (1.67-1.70 mol drug/g total lipid), which is in good agreement with the amount (1.78 mol diethylammonium/mol phospholipid) based on the diethyammonium content of the liposomes, assuming stiochiometric exchange of intraliposomal diethylammonium ions for the drug molecules and estimated intraliposomal entrapped volume of approximately 1.7 l/mol phospholipid.

TABLE 40

Loading of CPT-11 in DSPC/Chol/PEG-DSPE liposomes containing 1.05N DEA-SOS.

| Drug/lipid input ratio, mol/g | Drug/lipid output ratio, mol/g | Encapsulation efficiency, % |
|---|---|---|
| 1.25 | 1.247 ± 0.038 | 99.8 ± 3.0 |
| 1.50 | 1.534 ± 0.052 | 102.3 ± 3.5 |
| 1.80 | 1.669 ± 0.043 | 92.7 ± 2.4 |
| 2.06 | 1.690 ± 0.054 | 82.0 ± 2.6 |
| 2.20 | 1.704 ± 0.062 | 77.5 ± 2.8 |
| 2.42 | 1.685 ± 0.103 | 69.6 ± 4.3 |

Unless indicated otherwise, the analytical data are presented as the mean±standard error of triplicate runs. The rat plasma pharmacokinetic data are the mean±standard error of duplicate runs.

Although the invention has been described with reference to the presently preferred embodiment, it should be understood that various modifications can be made without departing from the spirit of the invention. Accordingly, the scope of the invention should be determined with reference to the appended claims, along with the full scope of equivalents to which such claims are entitled. The disclosures of all cited articles and references, including patent applications and publications, are incorporated herein by reference for all purposes.

The invention claimed is:

1. An irinotecan liposome composition comprising irinotecan sucrose octasulfate encapsulated in lipid vesicles comprising one or more phospholipids, encapsulating a total of 150-550 mg irinotecan base per mmol total vesicle phospholipids.

2. The irinotecan liposome composition of claim 1, containing a total of 500 mg irinotecan base per mmol total vesicle phospholipids.

3. The irinotecan liposome composition of claim 1, wherein the lipid vesicles consist of a lecithin, cholesterol, and an amphipathic polymer.

4. The irinotecan liposome composition of claim 3, wherein the lecithin is a diacylphosphatidylcholine.

5. The irinotecan liposome composition of claim 3, wherein the amphipathic polymer is a polyethylene glycol-lipid derivative.

6. The irinotecan liposome composition of claim 3, wherein the amphipathic polymer comprises a polyethylene glycol-lipid derivative having a poly(ethylene glycol) portion with a molecular weight from about 250 to about 20,000.

7. The irinotecan liposome composition of claim 3, wherein the amphipathic polymer is selected from the group consisting of a polyethylene glycol phosphatidylethanolamine, a polyethylene glycol-diacylglycerol, and a polyethyleneglycol-ceramide derivative.

8. The irinotecan liposome composition of claim 3, wherein a. the lecithin is DSPC and
b. the amphipathic polymer is a polyethylene glycol-lipid derivative having a poly(ethylene glycol) portion with a molecular weight from about 250 to about 20,000.

9. The irinotecan liposome composition of claim 1, wherein the lipid vesicles comprise an uncharged lipid component and a neutral phospholipid.

10. The irinotecan liposome composition of claim 9, wherein the lipid vesicles comprise one or more uncharged lipid component(s) selected from the group consisting of: cholesterol, ceramide, diacylglycerol, an acyl(poly ether) and an alkylpoly(ether).

11. The irinotecan liposome composition of claim 9, wherein the lipid vesicles comprise a neutral phospholipid selected from the group consisting of: a diacylphosphatidylcholine, a sphingomyelin, and a diacylphosphatidylethanolamine.

12. The irinotecan liposome composition of claim 11, wherein the lipid vesicles comprise a neutral phospholipid selected from the group consisting of: a diacylphosphatidylcholine, a sphingomyelin, and a diacylphosphatidylethanolamine.

13. An irinotecan liposome dispersion comprising irinotecan liposomes encapsulating irinotecan sucrose octasulfate in unilamellar lipid bilayer vesicles having a size of about 110 nm and comprising one or more phospholipids, the irinotecan liposomes encapsulating a total of 150-500 mg irinotecan free base per mmol total vesicle phospholipids.

14. The irinotecan liposome dispersion of claim 13, wherein the vesicles comprise a lecithin, cholesterol and a polyethylene glycol-lipid derivative.

15. The irinotecan liposome dispersion of claim 14, wherein the vesicles consist of a lecithin, cholesterol and a polyethylene glycol-lipid derivative.

16. The irinotecan liposome dispersion of claim 14, wherein the vesicles consist of DSPC, cholesterol and a polyethylene glycol-lipid derivative.

17. The irinotecan liposome dispersion of claim 14, wherein the vesicles consist of DSPC, cholesterol and N-(methoxy-poly(ethylene glycol)-oxycarbonyl)-distearoylphosphatidylethanolamine (PEG-DSPE).

18. The irinotecan liposome dispersion of claim 14, wherein the irinotecan liposomes encapsulate a total of 500 mg irinotecan free base as irinotecan sucrose octasulfate.

19. The irinotecan liposome dispersion of claim 18, having a total irinotecan free base concentration of 3.44 to 4.62 mg/mL of the irinotecan liposome dispersion.

20. An irinotecan liposome dispersion comprising irinotecan liposomes encapsulating irinotecan sucrose octasulfate in unilamellar lipid bilayer vesicles having a size of about 110 nm and consisting of DSPC, cholesterol and a polyethylene glycol-lipid derivative, the irinotecan liposomes encapsulating a total of 150-500 mg irinotecan free base as irinotecan octasulfate per mmol total vesicle phospholipids, and up to 5 mg irinotecan free base per mL of the liposome dispersion.

\* \* \* \* \*